(12) United States Patent
Sun et al.

(10) Patent No.: US 9,943,592 B2
(45) Date of Patent: Apr. 17, 2018

(54) VACCINE ADJUVANTS FROM SELF-ASSEMBLING PEPTIDES

(75) Inventors: Xiuzhi Susan Sun, Manhattan, KS (US); Jishu Shi, Manhattan, KS (US)

(73) Assignee: KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 183 days.

(21) Appl. No.: 14/118,700

(22) PCT Filed: May 25, 2012

(86) PCT No.: PCT/US2012/039642
§ 371 (c)(1),
(2), (4) Date: Nov. 19, 2013

(87) PCT Pub. No.: WO2012/162637
PCT Pub. Date: Nov. 29, 2012

(65) Prior Publication Data
US 2014/0086952 A1 Mar. 27, 2014

Related U.S. Application Data

(60) Provisional application No. 61/490,438, filed on May 26, 2011.

(51) Int. Cl.
*A61K 39/39* (2006.01)
*A61K 39/12* (2006.01)
(Continued)

(52) U.S. Cl.
CPC .............. *A61K 39/39* (2013.01); *A61K 39/12* (2013.01); *A61K 39/145* (2013.01);
(Continued)

(58) Field of Classification Search
None
See application file for complete search history.

(56) References Cited

U.S. PATENT DOCUMENTS 6,916,488 B1 7/2005 Meier et al.
7,008,635 B1 3/2006 Coury et al.
(Continued)

FOREIGN PATENT DOCUMENTS

WO 0117574 3/2001
WO 02062969 8/2002
(Continued)

OTHER PUBLICATIONS

Cunningham et al., "Optimizing synthesis and expression of transmembrane peptides and proteins," Methods 41: 370-380 (2007).*
(Continued)

*Primary Examiner* — Janet L Andres
*Assistant Examiner* — M Franco G Salvoza
(74) *Attorney, Agent, or Firm* — Hovey Williams LLP

(57) ABSTRACT

Pharmaceutical or veterinary compositions, vaccine systems, methods, and kits for treating or protecting a subject from a condition using peptide-based adjuvants are provided. The peptide adjuvants comprise a peptide having a hydrophobic region, a turning region, and a hydrophilic region. The turning region comprises amino acid residues GSII (SEQ ID NO: 10). The peptide adjuvants can be used to immunopotentiate active agents by improving the immune response to the active agent.

20 Claims, 42 Drawing Sheets

```
G P G G X G P G G X ----------Elastic region of spider silk
| | | | | | | |          SEQ ID NO: 19

G X G X D X U X -----------Calcium binding domain
| | | | | | | |          SEQ ID NO: 20

G P G G D G P G G D---------eD₂
Calcium binding site         SEQ ID NO: 5
```

(51) Int. Cl.
A61K 39/145 (2006.01)
A61K 39/00 (2006.01)

(52) U.S. Cl.
CPC .......... A61K 2039/5252 (2013.01); A61K 2039/55516 (2013.01); A61K 2039/55555 (2013.01); A61K 2039/55566 (2013.01); C12N 2760/16134 (2013.01); C12N 2770/10034 (2013.01)

(56) References Cited

U.S. PATENT DOCUMENTS

| | | | |
|---|---|---|---|
| 7,745,570 B2 | 6/2010 | Tomich et al. | |
| 8,734,812 B1* | 5/2014 | Galeotti et al. | 424/250.1 |
| 2002/0151650 A1 | 10/2002 | Pathak et al. | |
| 2004/0171545 A1 | 9/2004 | Chaikof et al. | |
| 2007/0031449 A1* | 2/2007 | Bos | A61K 35/74 424/203.1 |
| 2009/0291095 A1* | 11/2009 | Baker et al. | 424/184.1 |
| 2010/0310593 A1* | 12/2010 | Brazer | A61K 39/118 424/190.1 |
| 2013/0018004 A1* | 1/2013 | Sun | A61L 27/22 514/21.4 |

FOREIGN PATENT DOCUMENTS

| | | | | |
|---|---|---|---|---|
| WO | WO 03068942 A2 * | 8/2003 | | |
| WO | 2006127048 | 11/2006 | | |
| WO | WO 2006127048 A2 * | 11/2006 | | |
| WO | WO 2007022557 A1 * | 3/2007 | .......... | C07K 14/001 |
| WO | 2008039483 | 4/2008 | | |
| WO | 2009012449 | 1/2009 | | |
| WO | 2010/111652 | 9/2010 | | |
| WO | 2011002249 | 1/2011 | | |
| WO | 2011112856 | 9/2011 | | |
| WO | 2012074588 | 6/2012 | | |
| WO | 2014089472 | 6/2014 | | |

OTHER PUBLICATIONS

Grove et al., "Design of a functional calcium channel protein: Inferences about an ion channel-forming motif derived from the primary structure of voltage-gated calcium channels," Protein Science 2: 1918-1930 (1993).*

Starr et al., "Primary structure of a calcium channel that is highly expressed in the rat cerebellum," PNAS vol. 88: 5621-5625 (1991).*

Olszewska et al., "Antipeptide Antibody Responses following Intranasal Immunization: Effectiveness of Mucosal Adjuvants," Infect. Immun. 68(9): 4923-4929 (2000).*

Kovac et al., "Functional and molecular analysis of L-type calcium channels in human esophagus and lower esophageal sphincter smooth muscle," Am J Physiol Gasterointest Liver Physiol 289(6): G998-1006 (2005).*

The International Search Report and Written Opinion dated Dec. 20, 2012 in the corresponding PCT/US2012/039642 application filed on May 25, 2012.

Huang, Hongzhou, "Design of a Sheer-Thinning Recoverable Peptide Hydrogel from native Sequences and Application for Influenza H1N1 Vaccine Adjuvant," The Royal Society of Chemistry 2011, Soft Matter, Jun. 2011, 8905-8912, vol. 7.

Gungormus, Mustafa, "Self Assembled Bi-Functional Peptide Hydrogels with Biomineralization-Directing Peptides," Biomaterials, Jun. 29, 2010, vol. 31, 7266-7274.

Li, Xiangdong, "Peptide Nanofiber Hydrogen Adjuvated Live Virus Vaccine Enhances Cross-Protective Immunity to Porcine Reproductive and Respiratory Syndrome Virus," Vaccine, Aug. 9, 2013, vol. 31, 4508-4515.

The International Preliminary Report on Patentability dated Sep. 11, 2012, in the PCT/US2011/027972 filed Mar. 10, 2011.

The Office Action dated Sep. 24, 2014, in the U.S. Appl. No. 14/118,700, filed Nov. 19, 2013.

Cunnongham, Fiona "Optimizing Synthesis and Expression of Transmembrane Peptides and Proteins" Science Direct, Jul. 16, 2006, pp. 370-380; vol. 41.

Starr, Terry V. B. "Primary Structure of a Calcium Channel that is Highly Expressed in the Rat Cerebellum" Proc. Natl. Acad. Sci. Jul. 1991, pp. 5621-5625; vol. 88.

Grove, Anne "Design of a Functional Calcium Channel Protein: Inferences about an Ion Channel-Forming Motif Derived from the Primary Structure of Voltage-gated Calcium Channels" Protein Science, Jul. 59, 1993, pp. 1918-1930, vol. 2.

Rapaport, Hanna "Hydrogel Scaffolds of Amphiphilic and Acidic Beta-Sheet Peptides," Advance Functional Materials, Sep. 22, 2008, 2889-2896, vol. 18, Published online Sep. 22, 2008.

Petka, Wendy A., "Reversible Hydrogels from Self-Assembling Artificial Proteins," www.sciencemag.org, Jul. 17, 1998, vol. 281.

Teesch, Lynn M., "Intrinsic Interactions between Alkaline-Earth Metal Ions and Peptides: A Gas-Phase Study," J. Am. Chem. Soc. 1990, 112, 4110-4120.

Yang, Wang-Jih., "Second Derivative and Fourier Self-Deconvolution approaches to Resolution Enhancement of Fourier Transform Infrared (FTIR) Spectra," 1981 International Conference on Fourier Transform Infrared Spectroscopy, 263-264, vol. 289, Bellingham, Wash.

Pistorius, Arthur, "Deconvolution as a Tool to Remove Fringes from an FT-IR Spectrum," Vibrational Spectroscopy 36, May 25, 2004, 89-95.

Saiani, A., "Self-Assembly and Gelation Properties of Alpha-Helix Versus Beta-Sheet Forming Peptides," Soft Matter—The Royal Society of Chemistry, 2009, 193-202, 5.

Caplan, Michael, "Self-Assembly of a Beta-Sheet Protein Governed by Relief of Electrostatic Repulsion Relative to van der Waals Attraction," Biomacromolecules, Jul. 19, 2000, 627-631, 1.

Aulisa, Ilorenzo, "Self-Assembly of Multidomain Peptides: Sequence Variation Allows Control over Cross-Linking and Viscoelasticity," Biomacromolecules, Jul. 23, 2009, 2694-2698, 10.

Kisiday, J., "self-Assembling Peptide Hydrogel Fosters Chondrocyte Extracellular Matrix Production and Cell Division: Implications for Cartilage Tissue Repair," Proceedings of the National Academy of Sciences of the USA, Jul. 23, 2002, 9996-100001, vol. 99.

Pochan, Darrin, "Thermally Reversible Hydrogels via Intramolecular Folding and Consequent Self-Assembly of a de Novo Designated Peptide," J. Am. Chem. Soc. Mar. 25, 2003, 11802-11803, 125.

Anderson, Daniel, "Smart Biomaterials," www.sciencemag.org, vol. 305, Sep. 24, 2004.

Skountzou, Ioanna, "Transcutaneous Immunization with Inactivated Influenza Virus Induces Protective Immune Responses," Vaccine 24, www.sciencedirect.com May 26, 2006, 6110-6119.

Shera, Jeanne, "Effects of Peptide Sequence on Surface Properties and Self-Assembly of an Amphiphilic pH-Responsive Peptide," Biomacromolecules, Jul. 30, 2009, 2446-2450, 10(9).

Scotter, Andrew, "Metal Ion-Dependent, Reversible, Protein Filament Formation by Designated Beta-Roll Polypeptides," BMC Structural Biology, www.biomedcentral.com, Oct. 11, 2007.

Hardy, John, "Polymeric Materials Based on Silk Proteins," www.elsevier.com/locate/polymer Aug. 9, 2008.

Banwell, Eleanor, "Rational Design and Application of Responsive Alpha-Helical Peptide Hydrogels," Nature Materials, Jun. 22, 2009, vol. 8.

Koutsonanos, Dimitrious, "Transdermal Influenza Immunization with Vaccine Coated Microneedle Arrays," PLOS One Journal, www.plosone.org, Mar. 2009, vol. 4, issue 3.

Lee, Kuen Young, "Hydrogels for Tissue Engineering," Chemical Reviews, American Chemical Society, Jul. 2001, vol. 101, No. 7.

Zhang, Shuguang, "Hydrogels wet or let die," Nature Materials, Jan. 2004, vol. 3.

(56) References Cited

OTHER PUBLICATIONS

Skountzou, Ioanna, "Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles," Journal of Virology, Feb. 2007, 1083-1094, vol. 81, No. 3.
Reed, Steven, "New Horizons in Adjuvants for Vaccine Development," Trends in Immunology, vol. 30, No. 1, Dec. 6, 2008.
Kazzaz, J., "Novel Anionic Microparticles Are a Potent Adjuvant for the Induction of Cytotoxic T Lymphocytes against recombinant p55 gag from HIV-1," Journal of Controlled Release 67, 2000, 347-356.
Nowak, Andrew, "Rapidly Recovering Hydrogel Scaffolds From Self-Assembling Diblock Copolypeptide Amphiphiles," Nature Journal, May 23, 2002, vol. 417.
Huang, Hongzhou, "Rational Design of Responsive Self-Assembling Peptides from Native Protein Sequences," Biomacromolecules, 3390-3394, vol. 11, Nov. 16, 2010.
Schneider, Joel, "Responsive Hydrogels from the Intramolecular Folding and Self-Assembly of a Designed Peptide," JACS Articles, Nov. 23, 2002.
Zawaneh, Peter, "Design of an Injectable Synthetic and Biodegradable Surgical Biomaterial," www.pnas.org, Apr. 6, 2010.
Salick, Daphne, "Design pf a Injectable β—Hairpin Peptide Hydrogel That Kills Methicillin-Resistant *Staphylococcus Aureus*," Advance Materials, 2009, 4120-4123, vol. 21.
Langer, Robert, "Designing Materials for Biology and Medicine," Nature, Apr. 1, 2004, vol. 428.
Nemirovskiy, Olga, "Determination of Calcium Binding Sites in Gas-Phase Small Peptides bu Tandem Mass Spectrometry," J. Am. Soc. Mass Spectrom May 11, 1998, 1020-1028, vol. 9.
Zhang, Shuguang, "Fabrication of Novel Biomaterials Through Molecular Self-Assembly," Nature Biotechnology, Oct. 2003, vol. 21, No. 10.
Branco, Monica, "Fast Dynamics of Semiflexible Chain Networks of Self-Assembled Peptides," Biomolecules, 2009, 1374-1380, vol. 10.
Cushing, Melinda, "Hydrogel Cell Cultures," Science Magazine, May 25, 2007, vol. 316.
Zhang, Shuming, "A Self-Assembly Pathway to Aligned Monodomain Gels," Nature Materials Jun. 13, 2010.
Cavalli, Silvia, "Amphiphilic Peptides and Their Cross-Disciplinary Role as Building Blocks for Nanoscience," Chemical Society Reviews, 2010, 214-263, vol. 39.
Jeong, Byeongmoon, "Biodegradable Block Copolymers as Injectable Drug-Delivery System," Nature, Aug. 28, 1997, vol. 388.
Koutsopoulos, Sotirios, "Controlled Release of Functional Proteins Through Designed self-Assembling Peptide Nanofiber Hydrogel Scaffold," www.pnas.org Mar. 24, 2009, 4623-4628, vol. 106, No. 12.
Mo, Xiaoqun, "Design of 11-Residue Peptides with Unusual Biophysical Properties: Induced Secondary Structure in the Absence of Water," Biophysical Journal, Mar. 1, 2008, 1807-1817, vol. 94, No. 5.
International Search Report and Written Opinion of the International Searching Authority dated Nov. 25, 2011 in corresponding PCT/US2011/027972 application.
The International Search Report and Written Opinion dated Mar. 4, 2014, in PCT/US2013/073645 filed Dec. 6, 2013.
Monera, Oscar "Relationship of Sidechain Hydrophobicity and Alpha-Helical Propemsity on the Stability of the Single-stranded Amphipathic Alpha-Helix" Journal of Peptide Science, 1995, pp. 319-329, vol. 1.
Rudinger, J. "Charactericstics of the Amino Acids as Components of a Peptide Hormone Sequence," Peptide Hormones, Jun. 1976, University Park Press.
"Designing Custom Peptides," Custom Peptide Synthesis, Sigma Genosys, www.sigma-senosys,com/peptide_design.asp."
Berendsen, Herman J.C. "A Glimpse of the Holy Grail?" Science, Oct. 23, 1998, pp. 642, vol. 282.
Voet, Donald Biochemistry, 1995 pp. 235-241, John Wiley & Sons, Inc.
Ngo, Thomas J. "Computational Complexity, Protein Structure Prediction, and the Levinthal Paradox" 1994, pp. 491-494.
Bradley, Christina Marchetti "Limits of Cooperativity in a Structurally Modular Protein: Response of the Notch Ankyrin Doman to Analogous Alanine Substitutions in Each Repeat," J. Mol. Biol., 2002, pp. 373-386, V. 324.
Branco, Monica C. "Macromolecular Diffusion and Release from Self-Assembled Beta-Hairpin Peptide Hydrogels" Biomaterials, Mar. 2009, pp. 1139-1347, V. 30(7).
The Office Action dated Oct. 10, 2013, in U.S. Appl. No. 13/583,528, filed Sep. 7, 2012.
The Office Action dated Mar. 4, 2013, in U.S. Appl. No. 13/583,528, filed Sep. 7, 2012.
The Office Action dated Jan. 1, 2014, in U.S. Appl. No. 14/118,700, filed Nov. 19, 2013.

* cited by examiner

G P G G X G P G G X ———— Elastic region of spider silk
| | | | | | | | SEQ ID NO: 19

G X G X D X U X ———— Calcium binding domain
| | | | | | | | SEQ ID NO: 20

G P G G D G P G G D ———— eD₂
Calcium binding site    SEQ ID NO: 5

| Precursor | [M+H+Ca]³⁺ (m/z 469.891) | | [M +2Ca-H]³⁺ (m/z 482.54) | | [M+Ca]²⁺ (m/z 704.33) | |
|---|---|---|---|---|---|---|
| Fragments | N-terminal | C-terminal | N-terminal | C-terminal | N-terminal | C-terminal |
| 1  F |  |  |  |  |  |  |
| 2  L | $a_2$; $b_2$ [a] | $[y_{14}\text{-H+Ca}]^{2+}$ | $a_2$; $b_2$ | $[y_{14}\text{-3H+2Ca}]^{2+}$ | $a_2$ |  |
| 3  I | $b_3$ | $[y_{13}\text{-H+Ca}]^{2+}$ |  | $[y_{13}\text{-3H+2Ca}]^{2+}$ $[y_{13}\text{-3H+2Ca-H2O}]^{2+}$ | $b_3$ |  |
| 4  V |  | $[y_{12}\text{-H+Ca}]^{2+}$ |  | $[y_{12}\text{-3H+2Ca}]^{2+}$ | $a_4$; $b_4$ | $[y_{12}\text{-H}_2\text{O-2H+Ca}]^+$ |
| 5  I |  |  |  |  |  | $[y_{11}\text{-H}_2\text{O-2H+Ca}]^+$ |
| 6  G |  | $[y_{10}\text{-H+Ca}]^{2+}$ |  |  |  | $[y_{10}\text{-2H+Ca}]^+$ $[y_{10}\text{-H}_2\text{O-2H+Ca}]^+$ |
| 7  P |  |  |  |  |  | $[y_9\text{-H}_2\text{O-2H+Ca}]^+$ |
| 8  G |  |  |  |  | $[b_8\text{-2H+Ca}]^+$ |  |
| 9  G |  |  | $[c_9\text{-H+Ca}]^{2+}$ |  | $[c_9\text{-H+Ca}]^{2+}$ $[c_9\text{-2H+Ca}]^+$ |  |
| 10  D |  |  |  |  | $[b_{10}\text{-H+Ca}]^{2+}$ $[a_{10}\text{-H+Ca}]^{2+}$ $[b_{10}\text{-2H+Ca}]^+$ $[c_{10}\text{-2H+Ca}]^+$ |  |
| 11  G |  |  |  |  | $[b_{11}\text{-2H+Ca}]^+$ | $y_5$ $[y_5\text{-H+Ca}]^+$ |
| 12  P |  |  |  |  | $[b_{12}\text{-H+Ca}]^{2+}$ | $y_4$ |
| 13  G | $[b_{13}\text{-H+Ca}]^{2+}$ |  |  |  | $[b_{13}\text{-H+Ca}]^{2+}$ |  |
| 14  G | $[b_{14}\text{-H+Ca}]^{2+}$ |  |  |  | $[b_{14}\text{-H+Ca}]^{2+}$ $[a_{14}\text{-H+Ca}]^{2+}$ |  |
| 15  D |  |  |  |  |  |  | a) Abundant fragments are shown in bold.

Fig. 11

| Precursor | | $[M+2Ca-H]^{3+}$ (m/z 605.948) | | $[M+H+Ca]^{3+}$ (m/z 593.299) | | $[M+Ca]^{2+}$ (m/z 889.444) | | $[M+2Ca]^{4+}$ (m/z 454.713) | |
|---|---|---|---|---|---|---|---|---|---|
| Fragments | | N-terminal | C-terminal | N-terminal | C-terminal | N-terminal | C-terminal | N-terminal | C-terminal |
| 1 | F | | | | | | | | |
| 2 | L | $a_2$; $b_2$ | $[y_{18}+2Ca-3H]^{2+}$ | $a_2$; $b_2$ | $[y_{18}+Ca-H]2+$ | | | $a_2$ | |
| 3 | I | $b_3$ | $[y_{17}+2Ca-3H]^{2+}$ | $b_3$ | $[y_{17}+Ca-H]2+$ $[z_{17}+Ca-2H]2+$ | $b_3$ | | $b_3$ | |
| 4 | V | $b_4$ | $[y_{16}+2Ca-3H]^{2+}$ | $b_4$ | $[y_{16}+Ca-H]2+$ | $b_4$ | | $a_4$; $b_4$ | $[y_{16}+2Ca-3H]^{2+}$ |
| 5 | I | | $[y_{15}+2Ca-3H]^{2+}$ | | $[y_{15}+Ca-H]2+$ | | | | $[y_{15}+2Ca-3H]^{2+}$ |
| 6 | G | | $[y_{14}+2Ca-3H]^{2+}$ | | | | | | $[y_{14}+2Ca-2H]^{2+}$ $[y_{14}+2Ca-3H-H_2O]^{2+}$ $[y_{14}+2Ca-3H]^{2+}$ |
| 7 | S | | | | | | | $[a_7+Ca-3H]^{2+}$ $[a_7+Ca-H]^{2+}$ $[b_7+Ca-H]^{2+}$ | $[y_{13}+2Ca-3H]^{2+}$ |
| 8 | I | | | | | | | | $[y_{12}+Ca-H]^{2+}$ $[y_{12}+2Ca-3H]^{2+}$ |
| 9 | I | | | | | | | | |
| 10 | G | | | | | | | $[b_{10}-H+Ca]^{2+}$ | |
| 11 | P | | | | | | | | |
| 12 | G | | | | | | | | |
| 13 | G | | | | | $[a_{13}+Ca-H]^{2+}$ $[b_{13}+Ca-H]^{2+}$ $[c_{13}+Ca-H]^{2+}$ | | | |
| 14 | D | | | | | $[b_{14}+Ca-H]^{2+}$ $[b_{14}+Ca-H-H_2O]^{2+}$ | | $[b_{14}-H+Ca]^{2+}$ | |
| 15 | G | | | | | $[b_{15}+Ca-H]^{2+}$ | | | $[y_5+Ca-H]^{+}$ |
| 16 | P | | | | | | | | |
| 17 | G | | | | | | | | |
| 18 | G | | | | | $[b_{18}+Ca-H]^{2+}$ | | | |
| 19 | D | | | | | | | | |

Fig. 12

| Percentage of positive serum | | | | |
|---|---|---|---|---|
| Group/Date | D7 | D14 | D21 | D28 |
| Naïve pigs | 0/15 | 0/15 | 0/15 | 0/15 |
| MLV | 3/10 | 5/10 | 10/10 | 10/10 |
| MLV+ H9e | 4/10 | 9/10 | 10/10 | 10/10 |
| MLV+ A1/2 | 0/10 | 0/10 | 6/10 | 9/10 |
| MLV+ Gel01 | 2/10 | 4/10 | 10/10 | 10/10 |

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 1

Phe Leu Ile Val Ile
1               5

<210> SEQ ID NO 2
<211> LENGTH: 5
<212> TYPE: PRT
<213> ORGANISM: Artificial Sequence
<220> FEATURE:
```

-continued

```
<223> OTHER INFORMATION: Hydrophobic region of synthetic diblock peptide

<400> SEQUENCE: 2

Leu Leu Leu Leu Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Hydrophobic region derived from spider
      flagelliform silk protein
<220> FEATURE:
<221> NAME/KEY: MISC_FEATURE
<222> LOCATION: (3)..(3)
<223> OTHER INFORMATION: X is G, R, K, or Q
<220> FEATURE:
<221> NAME/KEY: MISC_FEATURE
<222> LOCATION: (8)..(8)
<223> OTHER INFORMATION: X is G, R, K, or Q

<400> SEQUENCE: 3

Gly Pro Xaa Gly Asp Gly Pro Xaa Gly Asp
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Hydophobic region derived from spider
      flagelliform silk protein
<220> FEATURE:
<221> NAME/KEY: MISC_FEATURE
<222> LOCATION: (8)..(8)
<223> OTHER INFORMATION: X is G, R, K, or Q

<400> SEQUENCE: 4

Lys Lys Lys Lys Lys Gly Pro Xaa Gly Asp
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Hydrophilic region derived from spider
      flagelliform silk protein

<400> SEQUENCE: 5

Gly Pro Gly Gly Asp Gly Pro Gly Gly Asp
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic hydrophilic region

<400> SEQUENCE: 6

Lys Lys Lys Lys Lys Lys Lys Lys Lys Lys
1               5                   10

<210> SEQ ID NO 7
<211> LENGTH: 10
<212> TYPE: PRT
<213> ORGANISM: Artificial Sequence
```

```
<220> FEATURE:
<223> OTHER INFORMATION: Hydrophilic region derived from spider
      flagelliform silk protein

<400> SEQUENCE: 7

Gly Pro Arg Gly Asp Gly Pro Arg Gly Asp
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Hydrophilic region derived from spider
      flagelliform silk protein

<400> SEQUENCE: 8

Gly Pro Gly Gly Asp Gly Pro Arg Gly Asp
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Hydrophilic region derived from spider
      flagelliform silk protein

<400> SEQUENCE: 9

Lys Lys Lys Lys Lys Gly Pro Arg Gly Asp
1               5                   10

<210> SEQ ID NO 10
<211> LENGTH: 4
<212> TYPE: PRT
<213> ORGANISM: Artificial Sequence
<220> FEATURE:
<223> OTHER INFORMATION: Peptide turning region derived from the third
      trans-membrane segment of subunit IV in the dihydropyridine
      sensitive human muscle L-type calcium channel

<400> SEQUENCE: 10

Gly Ser Ile Ile
1

<210> SEQ ID NO 11
<211> LENGTH: 19
<212> TYPE: PRT
<213> ORGANISM: Artificial Sequence
<220> FEATURE:
<223> OTHER INFORMATION: h9e peptide derivative of spider flagelliform
      silk protein and a trans-membrane segment of subunit IV in the
      dihydropyridine sensitive human muscle L-type calcium channel

<400> SEQUENCE: 11

Phe Leu Ile Val Ile Gly Ser Ile Ile Gly Pro Gly Gly Asp Gly Pro
1               5                   10                  15

Gly Gly Asp

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide adjuvant

<400> SEQUENCE: 12
```

Phe Leu Ile Val Ile Gly Ser Ile Ile Lys Lys Lys Lys Lys Lys
1               5                   10                  15

Lys Lys Lys

<210> SEQ ID NO 13
<211> LENGTH: 19
<212> TYPE: PRT
<213> ORGANISM: Artificial Sequence
<220> FEATURE:
<223> OTHER INFORMATION: Synthetic peptide adjuvant

<400> SEQUENCE: 13

Leu Leu Leu Leu Leu Gly Ser Ile Ile Lys Lys Lys Lys Lys Lys
1               5                   10                  15

Lys Lys Lys

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide adjuvant

<400> SEQUENCE: 14

Phe Leu Ile Val Ile Gly Ser Ile Ile Gly Pro Arg Gly Asp Gly Pro
1               5                   10                  15

Arg Gly Asp

<210> SEQ ID NO 15
<211> LENGTH: 19
<212> TYPE: PRT
<213> ORGANISM: Artificial Sequence
<220> FEATURE:
<223> OTHER INFORMATION: Synthetic peptide adjuvant

<400> SEQUENCE: 15

Phe Leu Ile Val Ile Gly Ser Ile Ile Gly Pro Gly Gly Asp Gly Pro
1               5                   10                  15

Arg Gly Asp

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide adjuvant

<400> SEQUENCE: 16

Leu Leu Leu Leu Leu Gly Ser Ile Ile Lys Lys Lys Lys Lys Gly Pro
1               5                   10                  15

Arg Gly Asp

<210> SEQ ID NO 17
<211> LENGTH: 15
<212> TYPE: PRT
<213> ORGANISM: Artificial Sequence
<220> FEATURE:
<223> OTHER INFORMATION: h5e peptide derivative of spider flagelliform
      silk protein and a trans-membrane segment of subunit IV in the
      dihydropyridine sensitive human muscle L-type calcium channel

<400> SEQUENCE: 17

Phe Leu Ile Val Ile Gly Pro Gly Gly Asp Gly Pro Gly Gly Asp
1               5                   10                  15

-continued

```
<210> SEQ ID NO 18
<211> LENGTH: 9
<212> TYPE: PRT
<213> ORGANISM: Artificial Sequence
<220> FEATURE:
<223> OTHER INFORMATION: Hydrophobic region and turning region
      derivative of the third trans-membrane segment of subunit IV in
      the dihydropyridine sensitive human muscle L-type calcium channel

<400> SEQUENCE: 18

Phe Leu Ile Val Ile Gly Ser Ile Ile
1               5

<210> SEQ ID NO 19
<211> LENGTH: 5
<212> TYPE: PRT
<213> ORGANISM: Artificial Sequence
<220> FEATURE:
<223> OTHER INFORMATION: Derivative of beta-spiral motif of spider
      flagelliform silk protein
<220> FEATURE:
<221> NAME/KEY: REPEAT
<222> LOCATION: (1)..(5)
<220> FEATURE:
<221> NAME/KEY: MISC_FEATURE
<222> LOCATION: (5)..(5)
<223> OTHER INFORMATION: X is any amino acid

<400> SEQUENCE: 19

Gly Pro Gly Gly Xaa
1               5

<210> SEQ ID NO 20
<211> LENGTH: 8
<212> TYPE: PRT
<213> ORGANISM: Artificial Sequence
<220> FEATURE:
<223> OTHER INFORMATION: Derivative of Ca2+ binding domain of lipase Lip
      A from Serratia marcescens
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (6)..(6)
<223> OTHER INFORMATION: X is any amino acid
<220> FEATURE:
<221> NAME/KEY: MISC_FEATURE
<222> LOCATION: (7)..(7)
<223> OTHER INFORMATION: X is a hydrophobic residue
<220> FEATURE:
<221> NAME/KEY: MISC_FEATURE
<222> LOCATION: (8)..(8)
<223> OTHER INFORMATION: X is any amino acid

<400> SEQUENCE: 20

Gly Xaa Gly Xaa Asp Xaa Xaa Xaa
1               5

<210> SEQ ID NO 21
<211> LENGTH: 15
<212> TYPE: PRT
<213> ORGANISM: Artificial Sequence
<220> FEATURE:
<223> OTHER INFORMATION: Synthetic diblock peptide
```

```
<400> SEQUENCE: 21

Leu Leu Leu Leu Leu Lys Lys Lys Lys Lys Lys Lys Lys Lys
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: D-amino acid

<400> SEQUENCE: 22

Leu Leu Leu Leu Leu Pro Pro Lys Lys Lys Lys Lys Lys Lys Lys
1               5                   10                  15

Lys

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide

<400> SEQUENCE: 23

Leu Leu Leu Leu Leu Gly Ser Ile Ile Lys Lys Lys Lys Lys Lys
1               5                   10                  15

Lys Lys Lys

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide

<400> SEQUENCE: 24

Phe Leu Ile Val Ile Ser Ile Ile Gly Pro Gly Gly Asp Gly Pro Gly
1               5                   10                  15

Gly Asp

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: D-amino acid

<400> SEQUENCE: 25

Phe Leu Ile Val Ile Pro Pro Gly Pro Gly Gly Asp Gly Pro Gly Gly
1               5                   10                  15

Asp

<210> SEQ ID NO 26
<211> LENGTH: 19
<212> TYPE: PRT
<213> ORGANISM: Artificial Sequence
<220> FEATURE:
```

```
<223> OTHER INFORMATION: Synthetic peptide

<400> SEQUENCE: 26

Phe Leu Ile Val Ile Ile Ile Val Ile Gly Pro Gly Gly Asp Gly Pro
1               5                   10                  15

Gly Gly Asp

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide

<400> SEQUENCE: 27

Leu Leu Leu Leu Leu Gly Ser Ile Ile Gly Pro Gly Gly Asp Gly Pro
1               5                   10                  15

Gly Gly Asp

<210> SEQ ID NO 28
<211> LENGTH: 20
<212> TYPE: PRT
<213> ORGANISM: Artificial Sequence
<220> FEATURE:
<223> OTHER INFORMATION: Derivative of N-terminal region of mineral
      directing gelator (MDG) 1

<400> SEQUENCE: 28

Val Lys Val Lys Val Lys Val Lys Val Pro Pro Thr Lys Val Glu Val
1               5                   10                  15

Lys Val Lys Val
            20
```

VACCINE ADJUVANTS FROM SELF-ASSEMBLING PEPTIDES

CROSS-REFERENCE TO RELATED APPLICATIONS

The present application is the National Stage of International Application No. PCT/US2012/039642, filed May 25, 2012, which claims the priority benefit of U.S. Provisional Patent Application Ser. No. 61/490,438, filed May 26, 2011, entitled RATIONAL DESIGN OF RESPONSIVE SELF-ASSEMBLING PEPTIDES DERIVED FROM NATIVE SEQUENCES AND APPLICATION FOR INFLUENZA H1N1 VACCINE ADJUVANT, incorporated by reference in its entirety herein.

SEQUENCE LISTING

The following application contains a sequence listing in computer readable format (CRF), submitted as a text file in ASCII format entitled "SequenceListing," created on May 24, 2012, as 9 KB. The content of the CRF is hereby incorporated by reference.

BACKGROUND

Field of the Invention

The present disclosure relates to peptide-based adjuvants, associated vaccines, and pharmaceutical or veterinary compositions containing the same.

Description of Related Art

Vaccines may be administered in conjunction with an adjuvant. An adjuvant is a substance that increases the immunological response to a vaccine when administered before, during, or after administration of the vaccine. Adjuvants potentiate the vaccine by stimulating antigen-presenting cells and other immune cells or by controlling the release of antigens from the injection site. An adjuvant may be administered with the vaccine or at a time, manner, or site that differs from the time, manner, or site at which the vaccine is administered. Vaccines containing dead organisms (inactivated vaccines) or pieces of the infectious organisms or their toxins (acellular or recombinant vaccines) generally need adjuvants to boost their effectiveness. Common adjuvants include aluminum hydroxide, aluminum potassium sulfate, other mineral salts, oil emulsions, particulate adjuvants, and microbial derivatives. Modified live vaccines (aka live attenuated vaccines), containing weakened forms of an infectious organism, are generally not administered with an adjuvant and there are few adjuvants available for use with live vaccines. In addition, many adjuvants for use with vaccines are known to cause unacceptable side effects in some patients, including adverse reactions and injection-site reactions, while some are toxic. There is also a large variety of new and future vaccine candidates against infectious, allergic and autoimmune diseases, and also for cancer and fertility treatment, which all require diverse new adjuvants with desirable functions and performance to successfully achieve new vaccine development and implementation. Thus, there is a need in the art for improved adjuvants, and particularly adjuvants that can be used with modified live vaccines.

SUMMARY

The present disclosure is broadly concerned with pharmaceutical or veterinary compositions comprising a peptide adjuvant and an active agent, optionally dispersed in a pharmaceutically-acceptable carrier. The peptide adjuvant comprises a peptide having a hydrophobic region, a turning region, and a hydrophilic region, with the turning region being between the hydrophobic and hydrophilic regions. The turning region comprises (in any order) amino acid residues GSII (SEQ ID NO: 10).

Methods of treating or preventing a condition in a subject are also disclosed. The methods comprise administering to the subject a therapeutically-effective amount of a peptide adjuvant and an active agent. The peptide adjuvant comprises a peptide having a hydrophobic region, a turning region, and a hydrophilic region, with the turning region being between the hydrophobic and hydrophilic regions. The turning region comprises (in any order) amino acid residues GSII (SEQ ID NO: 10).

Embodiments described herein are also concerned with vaccine systems. The systems comprise an active agent and a peptide adjuvant. The peptide adjuvant comprises a peptide having a hydrophobic region, a turning region, and a hydrophilic region, with the turning region being between the hydrophobic and hydrophilic regions. The turning region comprises (in any order) amino acid residues GSII (SEQ ID NO: 10).

The disclosed embodiments are also concerned with kits for vaccinating a subject to treat or prevent a condition. The kits comprise a vaccine system as described above and herein, and instructions for administering the vaccine system to the subject.

BRIEF DESCRIPTION OF THE DRAWINGS

FIG. 11 is a table of the fragmentation behavior of several precursor ions observed in the ESI spectra of the h5e peptide (M);

FIG. 12 is a table of the fragmentation behavior of several precursor ions observed in the ESI spectra of the h9e peptide (M);

DETAILED DESCRIPTION

Figures 1, 2:
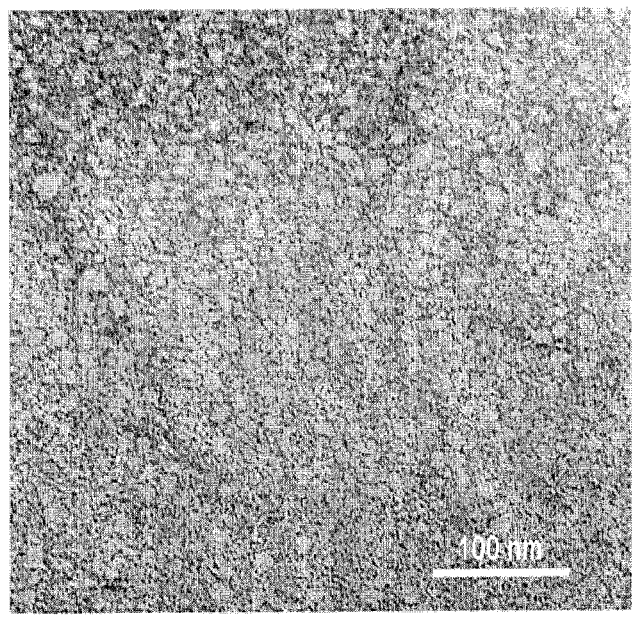
FIG. 1 is diagram showing how the elastic calcium-binding peptide $eD_2$ was derived from the calcium-binding domain and elastic region of spider silk.
FIG. 2 shows a TEM image of $eD_2$ in water.

The present disclosure is concerned with novel peptide-based adjuvants, associated vaccines, and pharmaceutical (or veterinary) compositions containing the same. The term "adjuvant" is used herein to refer to substances that have immunopotentiating effects and are added to or co-formulated with an active agent in order to enhance, elicit, and/or modulate the innate, humoral, and/or cell-mediated immune response against the active agent. In one or more embodiments, a composition suitable for pharmaceutical or veterinary use is provided. The composition comprises a peptide adjuvant and an active agent, optionally dispersed in a pharmaceutically-acceptable carrier.

Peptide Adjuvants

The peptide adjuvants are amphiphilic and self-assembling, and preferably comprise three segments or regions: a hydrophobic region, a turning region, and a hydrophilic region. The turning region is positioned between, and preferably directly connected to, the hydrophobic and hydrophilic regions. The hydrophobic region is preferably elastic and capable of binding Group I and Group II metals (and particularly calcium). Preferred hydrophobic regions comprise from about 2 to about 15 amino acid residues, preferably from about 4 to about 9 amino acid residues, and more preferably about 5 amino acid residues. The amino acid residues are preferably selected from the group consisting of F, L, I, and V. As used herein, it will be appreciated that when referring to amino acids that are present as part of a peptide, the amino acids are actually amino acid residues, regardless of whether "residues" is specifically stated. In some embodiments, the hydrophobic region comprises, and preferably consists of, in any order, amino acid residues of FLIVI (SEQ ID NO:1). In other embodiments, the hydrophobic region comprises, and preferably consists of, in order, amino acid residues of FLIVI (SEQ ID NO: 1). In one or more embodiments, the hydrophobic region comprises, and preferably consists of LLLLL (SEQ ID NO:2).

Preferred hydrophilic regions comprise from about 5 to about 20 amino acid residues, preferably from about 5 to about 10 amino acid residues, and more preferably about 10 amino acid residues. More preferably, the hydrophilic regions comprise amino acid residues selected from the group consisting of G, P, D, R, K, and Q. In one or more embodiments, the hydrophilic region comprises, and preferably consists of, in any order, amino acid residues of GPXGDGPXGD (SEQ ID NO:3), where each X is selected from the group consisting of G, R, K, and Q. In some embodiments, the hydrophilic region comprises, and preferably consists of, in any order, amino acid residues of KKKKKGPXGD (SEQ ID NO:4), where each X is selected from the group consisting of G, R, K, and Q. In other embodiments, the hydrophilic region comprises, and preferably consists of KKKKKKKKKK (SEQ ID NO:6). Particularly preferred hydrophilic regions comprise, and preferably consist of, in any order, amino acid residues selected from the group consisting of GPGGDGPGGD (SEQ ID NO:5), GPRGDGPRGD (SEQ ID NO:7), GPGGDGPRGD (SEQ ID NO:8), KKKKKKKKKK (SEQ ID NO:6), and KKKKKGPRGD (SEQ ID NO:9), or a fragment or variant having at least about 70% sequence identity to one of these sequences. More preferably, the % sequence identity is at least about 80% and even more preferably at least about 90%.

The turning region comprises, and preferably consists of, amino acid residues of GSII (SEQ ID NO: 10), in any order, and even more preferably in this order.

The inventive peptides are preferably short peptides. That is, it is preferred that the inventive peptides have less than about 30 amino acid residues, more preferably less than about 20 amino acid residues, and even more preferably about 19 amino acid residues. The most preferred peptide according to the embodiments disclosed herein comprises, and preferably consists of, the amino acid sequence FLIVIGSIIGPGGDGPGGD (SEQ ID NO: 11), or a fragment or variant thereof having at least about 70% sequence identity to this sequence, more preferably at least about 80% sequence identity to this sequence, and even more preferably at least about 90% sequence identity to this sequence. Additional preferred peptides according to the embodiments disclosed herein comprise, and preferably consists of, amino acid residues selected from the group consisting of FLIVIGSIIKKKKKKKKKK (SEQ ID NO:12), LLLLLGSIIKKKKKKKKK (SEQ ID NO:13), FLIVIGSIIGPRGDGPRGD (SEQ ID NO:14), FLIVIGSIIGPGGDGPRGD (SEQ ID NO:15), and LLLLLGSIIKKKKKGPRGD (SEQ ID NO: 16), or a fragment or variant there of having at least about 70% sequence identity, more preferably at least about 80% sequence identity, and even more preferably at least about 90% sequence identity to these sequences.

Finally, the inventive peptides will have a weight average molecular weight of from about 600 Da to about 4,500 Da, more preferably from about 1,000 Da to about 3,000 Da, and more preferably about 1,740 Da.

The inventive peptides can be prepared by microwave synthesizer, microbiosynthesis, fermentation, or genetic engineering technologies. A preferred method involves combining two native sequences from an elastic segment of spider silk and a trans-membrane segment of human muscle L-type calcium channel. More specifically, hydrophilic regions in one or more embodiments are designed from a spider flagelliform silk protein, while the hydrophobic and turning regions are derived from human muscle L-type calcium channel protein. In one or more embodiments, a peptide solution is then formed. The peptide is suspended, dispersed, or dissolved in a solvent (preferably water) at levels of at least about 0.1%, preferably from about 0.1% to about 5% by weight, more preferably from about 0.3% to about 3.5% by weight, and even more preferably from about 0.5% to about 2% by weight, based upon the total weight of the solution taken as 100% by weight. It is preferred that this peptide solution have a pH of from about 6 to about 12, and more preferably from about 8 to about 10. The peptides can also be desiccated or freeze-dried for storage until use.

The peptides can be used to form hydrogels. Advantageously, low levels of the peptides can be used to form these gels. The method involves providing a solution of the peptide or forming a peptide solution (described above). The peptide solution can then be converted to a gel by adjusting the pH or adding ions to the solution. In the pH adjustment method, the pH of the solution is adjusted to a level of from about 1 to about 6, preferably from about 2 to about 5, and more preferably from about 3 to about 4. This can be accomplished, for example, by adding an acid selected from the group consisting of HCl, formic acid (HCOOH), acetic acid ($CH_3COOH$), HBr, and nitric acid ($HNO_3$) until such pH is achieved. In the other method, a source of ions (described in more detail below) is introduced into the peptide solution. In either method, the gel is considered formed once G' (storage modulus) is greater than G" (storage loss).

The gels formed by the above methods have a uniform internetwork morphology with a porous structure and open cells. They typically comprise from about 0.1% to about 3% by weight of the peptide, preferably from about 0.25% to about 1.5% by weight of the peptide, and more preferably from about 0.5% to about 1% by weight of the peptide, based on the total weight of the gel taken as 100% by weight. The average cell size of the gel will be from about 10 μm to about 80 μm, preferably from about 20 μm to about 60 μm, and more preferably from about 30 μm to about 50 μm, as observed under a scanning electron microscope. Furthermore, the gel will comprise peptide nanofibers having an average diameter of from about 3 nm to about 30 nm, preferably from about 5 nm to about 20 nm, and more preferably from about 8 nm to about 15 nm, as measured under a transmission electron microscope. The gel will include peptide nanofibers having an average length of from about 0.3 μm to about 5 μm, preferably from about 0.8 μm to about 3 μm, and more preferably from about 1 μm to about 2 μm.

The inventive gels also possess a number of advantageous properties. The gels are shear thinning (i.e., the viscosity decreases with an increase in the rate of shear stress) when created by the ion trigger method. With either the ion trigger method or the pH adjustment method, the gels are very strong, having a storage modulus of at least about 500 Pa, preferably from about 800 Pa to about 3,000 Pa, and even more preferably from about 1,000 Pa to about 2,500 Pa at a peptide concentration of 0.85% and at room temperature (about 22° C.). The gels formed by the ion trigger method can achieve a storage modulus of at least about 800 Pa, preferably from about 900 Pa to about 1,500 Pa, and even more preferably from about 1,000 Pa to about 1,200 Pa at a peptide concentration of 0.85% and a temperature of 90° C. The gels formed by the pH adjustment method can achieve a storage modulus of at least about 800 Pa, preferably from about 900 Pa to about 1,500 Pa, and even more preferably from about 1,000 Pa to about 1,200 Pa at a peptide concentration of 0.85% and a temperature of 75° C.

After gel destruction, the gels have a % recovery of at least about 60%, preferably at least about 80%, more preferably at least about 90%, and even more preferably about 100% in less than about 10 minutes, preferably less than about 5 minutes, and more preferably less than about 2 minutes. A gel's % recovery is the % of the original (i.e., before gel destruction) storage modulus achieved by the gel after destruction.

The inventive gels are water soluble and temperature stable up to about 90° C. As used herein, "water soluble" means the gels can be diluted with water after formation, and "temperature stable" means that the hydrogel retains substantially all of its properties and is not denatured at temperatures ranging from about 1° C. to about 90° C.

Vaccines and Methods

The inventive peptide adjuvants and resulting hydrogels are useful for potentiating the immune effects of vaccines and other pharmaceutical or veterinary compositions. In one or more embodiments, the active agent useful in the inventive embodiments is an immunogenic active component (e.g., antigen) in that it resembles a disease-causing microorganism or infectious agent, and/or is made from weakened or killed forms of the same, its toxins, subunits, particles, and/or one of its surface proteins, such that it provokes an immune response to that microorganism or infectious agent. Some vaccines contain killed, but previously virulent, microorganisms that have been destroyed. Examples include influenza, cholera, polio, hepatitis A, and rabies vaccines. Some vaccines contain live, attenuated microorganisms (modified live virus). These vaccines use live viruses that have been cultivated under conditions that disable their virulent properties, or closely related but less dangerous organisms to produce a broad immune response. Some are also bacterial in nature. Live vaccines typically provoke more durable immunological responses and in humans are the preferred type for healthy adults. Examples include yellow fever, measles, mumps, rubella, whooping cough, porcine reproductive and respiratory syndrome (PRRS), distemper, canine adenovirus Type 2, parainfluenza, and kennel cough vaccines. Toxoid vaccines are made from inactivated toxic compounds that cause illness rather than the microorganism itself. Examples of toxoid-based vaccines include tetanus and diphtheria. Protein subunit vaccines can also be used. In these vaccines, a fragment of the microorganism is used to create an immune response. Examples include subunit vaccines against HPV, hepatitis B, and the hemagglutinin and neuraminidase subunits of the influenza virus. Vaccines can also be formulated using viral or bacterial DNA to provoke an immune response. Furthermore, although most current vaccines are created using inactivated or attenuated compounds from microorganisms, synthetic vaccines using synthetic peptides, carbohydrates, or antigens can also be used. Cancer vaccines using tumor antigens are also contemplated herein. Suitable vaccines can be monovalent or polyvalent.

As noted above, the active agent and adjuvant can be dispersed in a carrier. The term carrier is used herein to refer to diluents, excipients, vehicles, and the like, in which the adjuvant and active agent(s) may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause any undesirable biological effects or interact in a deleterious manner with any of the other components of the composition in which it is contained. A pharmaceutically-acceptable carrier or excipient would naturally be selected to minimize any degradation of the active agent or adjuvant and to minimize any adverse side effects in the subject, as would be well known to one of skill in the art. Pharmaceutically-acceptable ingredients include those acceptable for veterinary use as well as human pharmaceutical use. Compositions suitable for administration via injection are typically solutions in sterile isotonic aqueous buffer. Exemplary carriers and excipients include aqueous solutions such as normal (n.) saline (~0.9% NaCl), phosphate buffered saline (PBS), sterile water/distilled autoclaved water (DAW), as well as cell growth medium (e.g., MEM, with or without serum,), aqueous solutions of dimethyl sulfoxide (DMSO), polyethylene glycol (PEG), and/or dextran (less than 6% per by weight.), various oil-in-water or water-in-oil emulsions, and the like.

In one or more embodiments, the composition can further comprise ions or a source of ions, with preferred ions being selected from the group consisting of ions of Group I and Group II metals. The most preferred Group I and Group II metal ions are selected from the group consisting of Ca, Na, Mg, K, and Zn ions, with Ca and Na ions being particularly preferred. Exemplary sources of these ions include Group I and Group II metal chlorides, Group I and Group II metal bromides, Group I and Group II metal sulfides, Group I and Group II metal carbonates and bicarbonates. When present, the molar ratio of peptide to ion is from about 1:1 to about 1:100, preferably from about 1:5 to about 1:20, and more preferably about 1:10.

In related embodiments, the composition can further comprise proteins, such as albumin from serum, plants, or other sources. Where necessary, the composition may also include solubilizing agents, preservatives, stabilizers, emulsifiers, and the like. A local anesthetic (e.g., lidocaine) may also be included in the compositions, particularly for injectable forms, to ease pain at the site of the injection.

The compositions and vaccines according to the embodiments disclosed herein are useful in treating and preventing disease. Thus, embodiments described herein have therapeutic and prophylactic uses, depending upon the particular active agent utilized. The terms "therapeutic" or "treat," as used herein, refer to processes that are intended to produce a beneficial change in an existing condition (e.g., infection, disease, disorder, etc. including cancer) of a subject. The terms "prophylactic" or "prevent," as used herein, refer to processes that are intended to inhibit or ameliorate the effects of a future infection or disease to which a subject may be exposed to.

In use (e.g., for a vaccine system), the ingredients are generally supplied either separately or mixed together in a unit dosage form. In one or more embodiments, the peptide adjuvant can be provided separately from the active agent (e.g., in its own vial, ampule, sachet, or other suitable container). Likewise, the active agent can be provided separately from the peptide adjuvant (e.g., in its own container). In some embodiments, additional ingredients, such as ions, proteins, etc. can be present in the active agent container. In other embodiments, any additional ingredients can be provided in yet a separate container. In some embodiments, any additional ingredients can be mixed in the carrier with which the active agent and adjuvant are mixed prior to administration. Regardless, when the ingredients are separately provided, it will be appreciated that the ingredients can then be mixed onsite by a practitioner before being administered to the subject to treat or prevent a condition. In one or more embodiments, the composition is administered less than about 72 hours after mixing, preferably about 24 hours after mixing, more preferably less than about 4 hours, and even more preferably about 1 to about 2 hours after mixing.

It will be appreciated that the active agent and adjuvant may be provided in various forms, depending upon the particular vaccine. For example, the peptide adjuvant can be provided in solution, or it can be provided in hydrogel form. Both of these forms are described above, and can be provided with or separate from the active agent. In one or more embodiments, the active agent is separately provided dispersed in a carrier along with ions or a source of ions, and optionally proteins. The active agent solution is mixed with the peptide solution prior to administration. Upon mixing, the adjuvant forms a hydrogel, as described herein. The peptide adjuvant can also be concentrated, desiccated, or freeze-dried with or without the active agent, and then reconstituted with carrier before administration. For example, the active agent and/or adjuvant (optionally along with additional ingredients) can be provided as a dry, lyophilized powder or water-free concentrate. The vaccine components can then be rehydrated with the accompanying liquid diluent (carrier), which is added to the vaccine container (or vice versa). Optionally only one of the adjuvant or active agent is dried, while the other is provided in solution (e.g., dispersed in the carrier). Regardless, the carrier may contain additional ingredients, such as ions or protein, which trigger hydrogel formation in the composition. In alternative embodiments, the vaccine components are free of ions or proteins. Instead, hydrogel formation is triggered in situ once the composition is administered, relying on ions and proteins in the body of the subject to trigger hydrogel formation. In alternative embodiments, the active agent and adjuvant are not mixed prior to administration, but are co-administered to the subject. In such embodiments, the adjuvant and/or active agent may be dispersed in a carrier, optionally along with any additional ingredients. The term "co-administer," as used herein, refers to administering the adjuvant, as part of a distinct composition, substantially simultaneously, sequentially, or separately with the active agent. It will be appreciated that other vaccine forms or systems may be used, depending on the nature of the active agent and the route of administration.

Regardless, the composition to be administered will comprise a therapeutically effective amount of adjuvant and/or active agent. As used herein, a "therapeutically effective" amount refers to the amount that will elicit the biological or medical response of a tissue, system, or subject that is being sought by a researcher or clinician, and in particular elicit some desired therapeutic or prophylactic effect. One of skill in the art recognizes that an amount may be considered therapeutically effective even if the condition is not totally eradicated or prevented but improved or inhibited partially. In some embodiments, the weight ratio of adjuvant to active agent in the composition will be from about 1:100 to about 1:1, preferably from about 1:10 to about 1:50, and more preferably from about 1:10 to about 1:20.

Further embodiments described herein are concerned with methods of treating or preventing a condition in a subject. The methods comprise administering to a subject a therapeutically effective amount of an active agent and a peptide adjuvant, as described herein. In some embodiments, the active agent and peptide adjuvant are co-administered as described above. In one or more embodiments, the methods comprise administering to a subject a pharmaceutical or veterinary composition comprising a therapeutically effective amount of an active agent and a peptide adjuvant, optionally dispersed in a pharmaceutically acceptable carrier. In some embodiments, the subject is afflicted with a condition (e.g., infection, disease, or disorder), wherein methods described herein are useful for treating the condition and/or ameliorating the effects of the condition. In other embodiments, the subject is free of a given condition, wherein the methods described herein are useful for preventing the occurrence of the condition and/or preventing the effects of the condition.

The disclosed embodiments are suitable for various routes of administration. The pharmaceutical or veterinary compositions can be injected intramuscularly, subcutaneously, or intradermally. They can also be administered via mucosa such as intranasally, orally, or intravaginally. The composition can also be administered through the skin via a transdermal patch.

A kit comprising a peptide adjuvant and an active agent is also disclosed herein. The kit further comprises instructions for administering the peptide adjuvant and active agent to a subject. As noted above, the peptide adjuvant and active agent can be provided in a single container or in separate containers in the kit. In one or more embodiments, the kit comprises an active agent held in a first container and a peptide adjuvant held in a second container. In one or more embodiments, the kit further comprises a carrier and instructions for preparing a pharmaceutical or veterinary composition as described herein. The carrier may be present in the same container as the adjuvant and/or active agent, or may be provided in a separate (e.g., third) container. In one or more embodiments, the kit comprises a first container comprising peptide adjuvant and active agent and a second container comprising a carrier, along with instructions for dispersing the adjuvant and active agent in the carrier. In an alternative embodiment, the kit comprises a first container comprising peptide adjuvant and a second container comprising an active agent dispersed in a carrier along with any additional ingredients. The kit further comprises instructions for mixing the peptide adjuvant with the active agent to form a pharmaceutical or veterinary composition as described herein.

It will be appreciated that therapeutic and prophylactic methods described herein are applicable to humans as well as any suitable animal, including, without limitation, dogs, cats, and other pets, as well as, rodents, primates, horses, cattle, etc. The methods can be also applied for clinical research. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The term "sequence identity" is used herein to describe the sequence relationships between two or more nucleic acid or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain % of sequence identity to a reference sequence does not necessarily have to have the same total number of nucleotides or amino acids. Thus, a sequence having a certain level of "identity" includes sequences that correspond to only a portion (i.e., 5' non-coding regions, 3' non-coding regions, coding regions, etc.) of the reference sequence.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Peptide Synthesis and Analysis

1. Peptide Synthesis

Peptides were synthesized on a CEM Liberty microwave peptide synthesizer (CEM Corporation, Matthews, N.C.) according to the automated base-labile 9-fluorenylmethoxycarbonyl (Fmoc) strategy with Fmoc-protected amino acids (EMD Biosciences, San Diego, Calif.). Peptides were cleaved using 95% trifluoroacetic acid (Sigma-Aldrich, Milwaukee, Wis.), 2.5% triisopropylsilane (Sigma), and 2.5% deionized water. After synthesis, peptides were washed three times with anhydrous ether (Fisher Biotech, Fair Lawn, N.J.), dissolved in acetonitrile and distilled deionized (DI) water (50/50 v/v), and then freeze-dried. Molecular weight and purity of the synthesized peptides were confirmed by matrix-assisted laser desorption/ionization time-of-flight mass spectroscopy (Ultraflex II instrument, Bruker Daltronics, Billerica, Mass.) and high performance liquid chromatography (HPLC, Beckman Coulter, Inc., Fullerton, Calif.).

2. Hydrogel Preparation

The synthesized peptide was dissolved in DI water to a concentration of 5 mM by adjusting the pH to 8.0-10.0 with 1 M NaOH (Sigma). The h5e acidic solution and acidic h9e hydrogel were made by adjusting the pH to 4.0 with 1 M HCl (Sigma). The h9e $Ca^{2+}$ hydrogel was prepared by adding $CaCl_2$ to a basic h9e peptide solution (molar ratio of peptide and $Ca^{2+}$ was 1:10, final pH was 7.0 to 9.0). The same method was used to prepare the h5e $Ca^{2+}$ solution.

3. Transmission Electron Microscopy (TEM)

Peptide solutions were prepared on Formvar/carbon-coated 200-mesh copper grids (Electron Microscopy Sciences, Fort Washington, Pa.) and stained with 2% (w/v) uranyl acetate (Ladd Research Industries, Inc., Burlington, Vt.) for 60 seconds at ambient conditions before being imaged. The samples were imaged with a CM 100 TEM (FEI Company, Hillsboro, Oreg.) at 100 kv.

4. Mass Spectrometry (MS)

MS experiments were performed using LTQ-Orbitrap (Thermo Electron Bremen, Germany) equipped with an electrospray ionization source. Samples were injected through a pulled fused silica capillary (50 μm ID) at a flow rate of 0.3 to 0.5 μL/min. using a spray voltage of 4 kV. The system was operated in the positive ion mode with a resolving power of 60,000 at m/z 400. MS/MS experiments were performed using a 2 to 3 amu isolation window. The collision energy was adjusted for each species to obtain about 70-90% fragmentation of the precursor ion. High-resolution mass analysis enabled unambiguous identification of the resulting fragments.

Stock solutions of peptides were prepared by dissolving 0.85 mg and 0.94 mg of h5e (SEQ ID NO:17; MW 1370.6951) and h9e (SEQ ID NO:11; MW 1740.9167), respectively, in 500 μL HPLC grade water and adding 60 to 80 μL of 0.25 M NaOH to obtain solutions with a pH of 8. Solutions for MS experiments were prepared by mixing 10 μL of the stock solution with 10 μC of 0.1 M $CaCl_2$ and adding 200 μL of 50:50 (v:v) $H_2O$/acetonitrile.

5. Circular Dichroism (CD) Experiments

The CD spectra of h9e basic solution, acidic hydrogel, and $Ca^{2+}$ hydrogel were recorded at ambient conditions using a Jasco J-815 Spectrometer (Jasco Corporation, Tokyo, Japan). The concentrations of the samples were 1 mM (0.17 wt %). CD spectra were recorded from 190 to 260 nm with 1 nm bandwidth and 20 nm $min^{-1}$ scanning speed, and then averaged over two accumulations. Baselines were recorded using basic, acidic, and $Ca^{2+}$ solutions without peptide.

6. Rheology

The storage, G', and loss, G", moduli of h9e acidic and $Ca^{2+}$ hydrogels were determined on a rheometer system C-VOR 150 (Malvern instruments, Malvern, Worcestershire WR141XZ, United Kingdom) with a 20-mm diameter parallel plate geometry through frequency sweep (strain 1%, frequency 0.01 to 10 Hz, temperature 25° C.), amplitude sweep (strain 1 to 500%, frequency 1 Hz, temperature 25° C.), and temperature profile (strain 1%, frequency 1 Hz, Temperature 5° C., 20° C., 37° C., 50° C., 75° C., and 90° C.) measurements. The multiple amplitude sweep experiments were conducted to test the moduli recovery of peptide hydrogels. The time gap between every two tests was 10, 30, and 60 seconds for h9e $Ca^{2+}$ hydrogel.

Example 2

H1N1 Killed Vaccine Adjuvant Study

1. Vaccine Preparation

Vaccines were prepared using FluSure XP® (H1N1 and H3N2 killed virus) from Pfizer as antigen. A 50-dose vial of vaccine was rehydrated to 100 ml with a 100 ml vial of sterile diluents from the manufacturer. The antigen was mixed with either h9e peptide adjuvant or a commercially-available adjuvant. The commercially-available adjuvant was an oil-in-water emulsion designated Amphigen® (4.5% oil; Pfizer). The antigens were mixed with PBS to make 2× vaccine and then mixed with an equal volume of h9e, or mixed with Amphigen® according to manufacturer recommendations. Dosages for vaccination were 200 μl/mouse.

2. Animals and Vaccination Study

In this study, C57/BL6 mice (female, 8-week old, 4 mice per group) were immunized twice in a 3-week interval with killed H1N1 swine influenza virus antigen (Pfizer) with h9e adjuvant or commercial oil-based adjuvant (Pfizer). Sera were collected from each mouse 2 weeks after the second immunization.

3. Antibody Response Analysis

Anti-swine H1N1 influenza virus-specific IgG1 were determined by enzyme-linked immunosorbent assay following the methods described by Skountzou et al. (J. Virology 81, 1083-1094 (2007)) and Koutsonanos et al. (PLoS ONE 4, e4773 (2009)) with some modifications. Optical density (OD) was read at 450 nm. The results were expressed as an S/P ratio calculated as the mean OD of duplicate wells of each unknown serum divided by the mean OD of a positive control.

The mean hemagglutination inhibition (HAI) titers followed the WHO protocol. After proper treatments, heat-inactivated sera were serially diluted and preincubated at room temperature with 4 HA units/50 ml of H1N1 virus for 30 min. An equal volume of 0.5% chicken red blood cells was then added to each well and incubated at room temperature for 30 min. The HAI titer was read as the reciprocal of the highest dilution of serum that conferred inhibition of hemagglutination. The values were expressed as the geometric mean of each treatment group.

Discussion

In this study, we report a self-assembling peptide designed by rationally combining two native functional sequences, the subsequent synthesis of responsive peptide hydrogels, and evaluation of these hydrogels for use as vaccine adjuvants. A novel peptide-based adjuvant (h9e) was designed that was biologically safe and improved H1N1 immune response by about 70% compared with an oil-based commercial adjuvant. The ability to induce H1N1-specific IgG1 antibody response of h9e was similar as that of the commercial adjuvant. No injection site reaction (redness or swelling) was observed in vaccinated mice, showing that the h9e is biocompatible in mice system testing.

The h9e peptide contains 19 amino acid residues with molecular weight of about 1740 Da containing anionic residues (i.e., aspartic acid), and formed β-structure at neutral pH. The peptide can form a hydrogel at low concentration (i.e., 0.05% in the presence of antigen) at neutral pH ranging from 5.0 to 11. The hydrogel is shear thinning, and becomes micro gels with Newtonian flow after shaking, and then becomes a hydrogel again after a short time. This hydrogel is water soluble and also temperature stable up to 90° C. The hydrogel has uniform internetwork morphology with a porous structure with open cell size from 20 m to 60 m. Under microscope, nanowire-like fibers were observed with diameter from 5 to 20 nm and length at μm scale, which is the main morphology of the hydrogel open cell wall.

Hydrogel formation has been achieved by designing model peptides with alternating charged and non-charged amino acids or blocks of hydrophobic and hydrophilic copolymers. The identified functional domains of native proteins also are potential models for peptide design. Here, we report a self-assembling peptide, $eD_2$, designed by rationally combining two native sequences from spider silk and calcium-binding motifs, which formed ordered fibrous aggregates triggered by $Ca^{2+}$. A 3-spiral motif of spider flagelliform silk protein, $[GPGGX]_n$ (X=any amino acid) (SEQ ID NO: 19), was selected as one of our model sequences. $[GPGGX]_n$ (SEQ ID NO: 19) proves the elasticity of the extremely high tensile strength of spider silk. The $Ca^{2+}$ binding domain of lipase Lip A from Serratia marcescens, $GXGXDXX^1X$ (X=any amino acid; $X^1$=hydrophobic residue) (SEQ ID NO:20), has a sequence structure similar to that of $[GPGGX]_n$ (SEQ ID NO:19) (FIG. 1, where X=any amino acid, and $U=X^1$=large hydrophobic residue). We combined these two motifs by replacing the X residues of $[GPGGX]_n$ (SEQ ID NO:19) with D and defined the newly designed peptide as GPGGDGPGGD ($eD_2$) (SEQ ID NO:5). The $Ca^{2+}$ binding sequence was hidden in the first eight residues of $eD_2$. This peptide was expected to assemble into fibres triggered by $Ca^{2+}$ ions.

Figure 3:
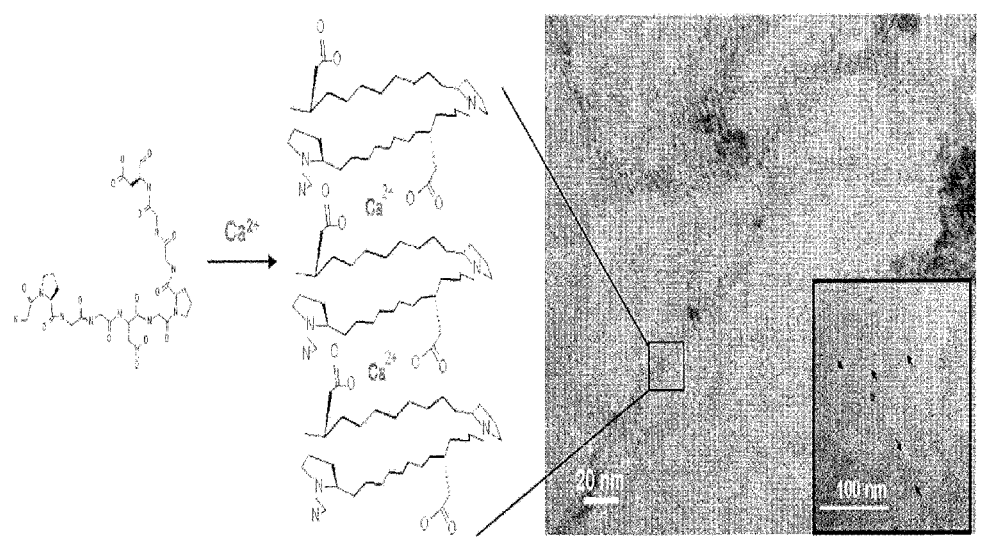
FIG. 3 shows a TEM image of $eD_2$ in 10 mM $Ca^{2+}$ solution, and the molecules binding with $Ca^{2+}$ assembled as nanofibres.
Figure 4:
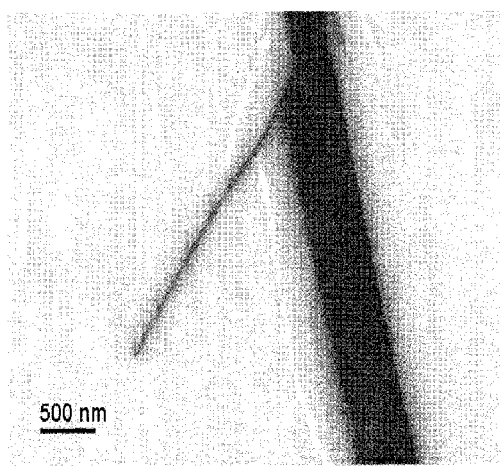
FIG. 4 shows a TEM image of $eD_2$ in 100 mM $Ca^{2+}$ solution, and nanofibres packed as sheet or rod shapes.

In water, $eD_2$ molecules formed uniform spherical agglomerates with diameter of 10 to 20 nm (FIG. 2). When $Ca^{2+}$ solution (20 mM) was added to the peptide solution (volume ratio: 50/50), peptide molecules bound to $Ca^{2+}$ at Asp residues assembled as a nanofiber with 10 nm width (FIG. 3). Some individual filaments stacked together by surface attraction as shown in the inserted window of FIG. 3 with a 100 nm scale bar. As $Ca^{2+}$ solution concentration increased to 200 mM, the $eD_2$ nanofibres compacted into high-density sheet and rod shapes tens of hundreds of nanometers in width and several micrometers in length (FIG. 4). This designed peptide bonded with $Ca^{2+}$ and orderly aggregated into nanofibre shape, presenting both fibre- and calcium-binding properties. The packing of peptide molecules could be tightened by increasing the link between peptides and ions.

We initially used $eD_2$ to design a responsive hydrogel for medical applications. Two native hydrophobic sequences, FLIVI (h5) (SEQ ID NO:1) and FLIVIGSII (h9) (SEQ ID NO:18), from the third transmembrane segment of subunit IV in the dihydropyridine-sensitive human muscle L-type calcium channel were tailored to $eD_2$. These two segments are sensitive to metal ions, possess adhesion when flanked with Lysine residues, and form nanofibers, which indicates that they are good hydrophobic segment candidates for hydrogel peptide design. We combined these two segments with $eD_2$ to design two new sequences: FLIVIGPGGDG-PGGD (h5e) (SEQ ID NO:17) and FLIVIGSIGPGGDG-PGGD (h9e) (SEQ ID NO: 11).

Figure 5:
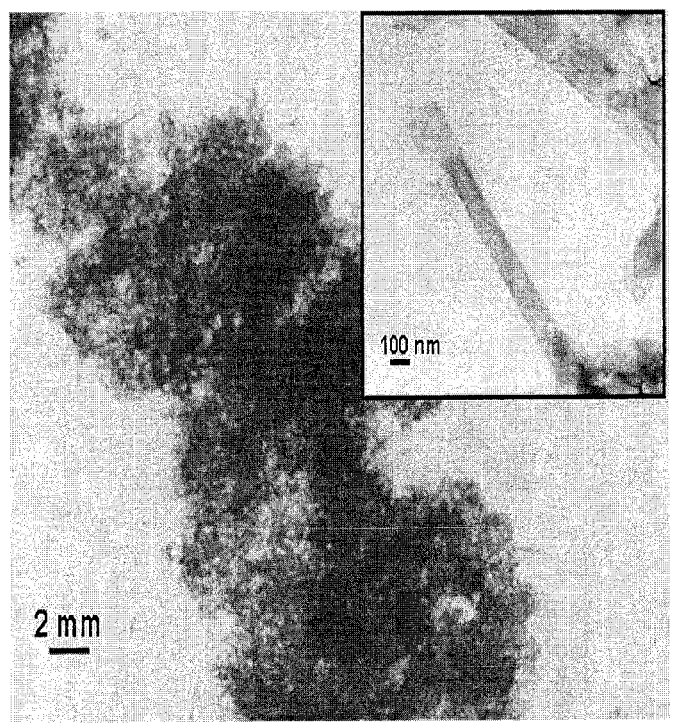
FIG. 5 shows a TEM image of aggregation of h5e in $Ca^{2+}$ solution.
Figure 6:
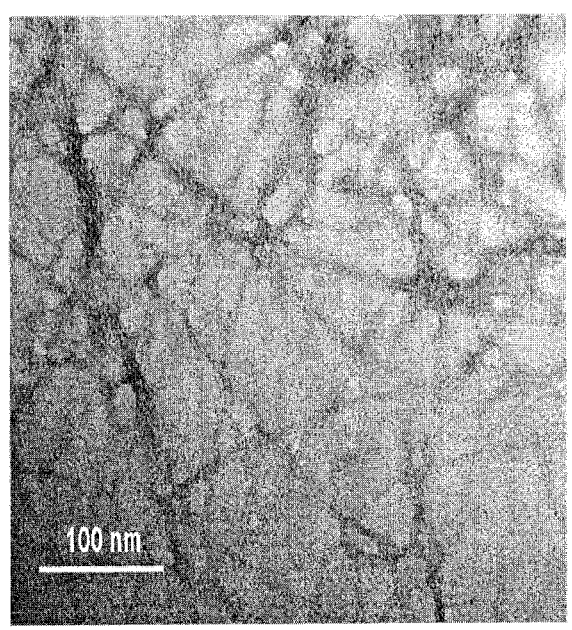
FIG. 6 shows a TEM image of hydrogel fibre network of h9e in $Ca^{2+}$ solution.
Figure 7:
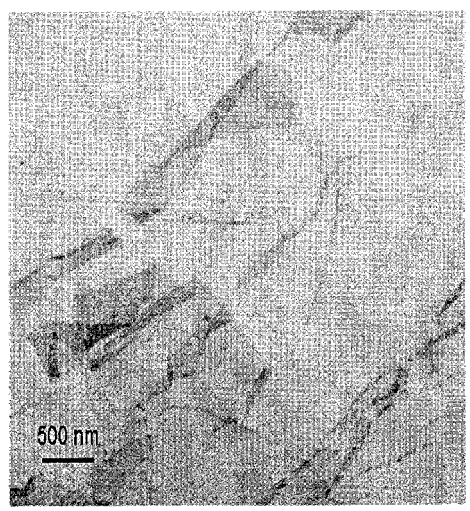
FIG. 7 shows a TEM image of a flat film of $L_5GSIIK_{10}$ (SEQ ID NO:23)
Figure 8:
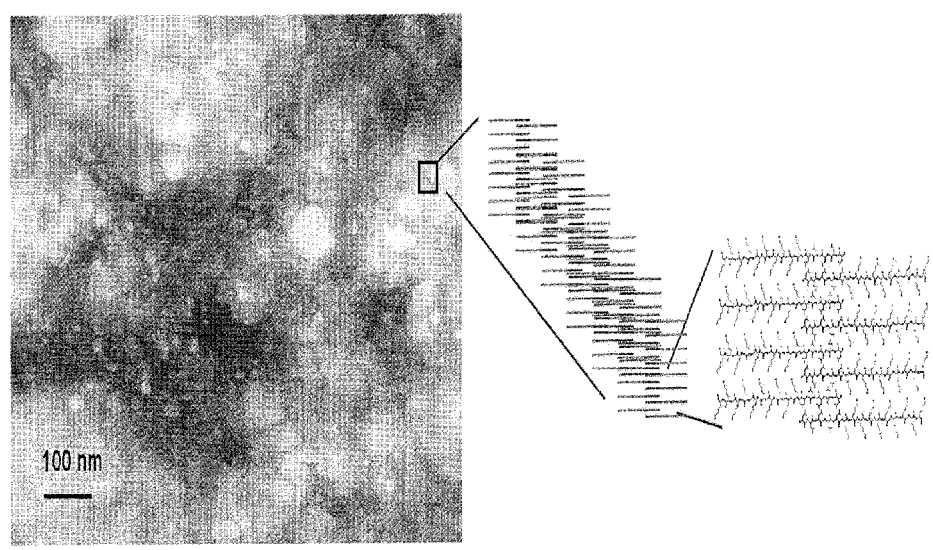
FIG. 8 shows a TEM image of a fibre network of $L_5K_{10}$, (SEQ ID NO:21), with the peptides stacked at the hydrophobic region and layered as nanofibres based on hydrogen bond.
Figure 9:
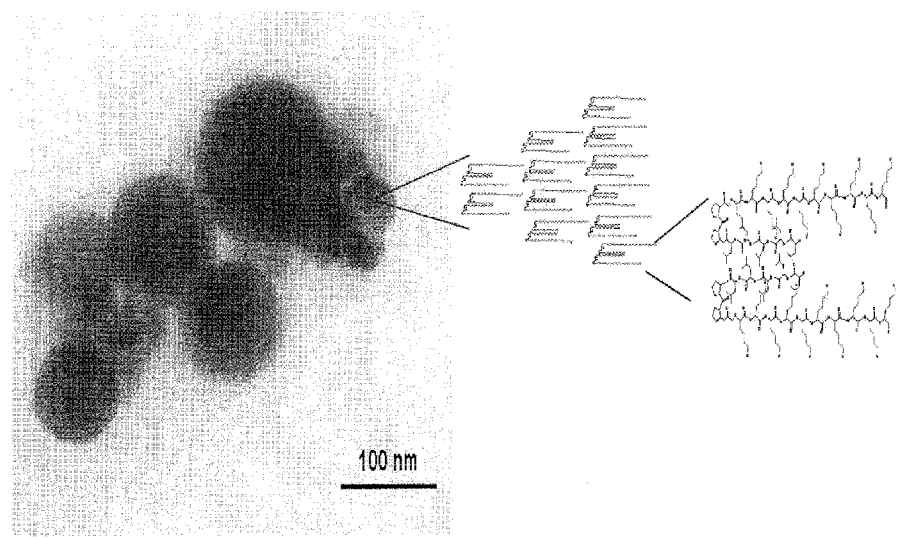
FIG. 9 shows circles of $L_5PP^DK_{10}$ (SEQ ID NO:22) peptides packed as a dilayer, folding the hydrophilic regions out.

Both peptides were expected to form hydrogels in $Ca^{2+}$ solution; however, h5e precipitated with $Ca^{2+}$, while h9e formed a hydrogel. The h5e molecules packed into twisted fibrillar tapes more than 100 nm in width (FIG. 5), whereas h9e molecules assembled into nanofibres (8 nm in width) and crossed as a hydrogel fibre network (FIG. 6). We hypothesized that the turning function of the GSII (SEQ ID NO: 10) segment dominated the assembly pathway of h9e. To demonstrate this hypothesis, we selected a simple diblock peptide, LLLLLKKKKKKKKKK ($L_5K_{10}$) (SEQ ID NO:21), consisting of both hydrophobic and hydrophilic segments. A segment with sharp turning function, $PP^D$, was inserted into the $L_5K_{10}$ (SEQ ID NO:21) and defined as $L_5PP^DK_{10}$ (SEQ ID NO:22). For comparison, GSII (SEQ ID NO:10) was also inserted into the diblock and defined as $L_5GSIIK_{10}$ (SEQ ID NO:23). In water, $L_5GSIIK_{10}$ (SEQ ID NO:23) formed a flat film (FIG. 7), $L_5K_{10}$ (SEQ ID NO:21) formed a fibre network (FIG. 8), while $L_5PP^DK_{10}$ (SEQ ID NO:22) formed nonuniform micelle structures (FIG. 9). The sharp-turning $PP^D$ segment made the hydrophobic block, $L_5$ (SEQ ID NO:2), parallel with the hydrophilic block $K_{10}$ (SEQ ID NO:6) in $L_5PP^DK_{10}$ (SEQ ID NO:22). Unlike the antiparallel assemble of $L_5K_{10}$ (SEQ ID NO:21) (FIG. 8), two $L_5PP^DK_{10}$ (SEQ ID NO:22) molecules packed the $L_5$ (SEQ ID NO:2) inside and folded $K_{10}$ (SEQ ID NO:6) outside as dilayer assemblies (FIG. 9), mirroring the association of peptides of alternating hydrophilic and hydrophobic residues. The association of $L_5GSIIK_{10}$ (SEQ ID NO:23) was between these two extreme (linear and sharp turning) situations. $Ca^{2+}$ ions (at 0.005M peptide concentration) were also added into peptides $L_5K_{10}$ (SEQ ID NO:21), $L_5PP^DK_{10}$ (SEQ ID NO:22) and L$_5$GSIIK$_{10}$ (SEQ ID NO:23) solutions, but no hydrogel formation was observed.

Figure 10:
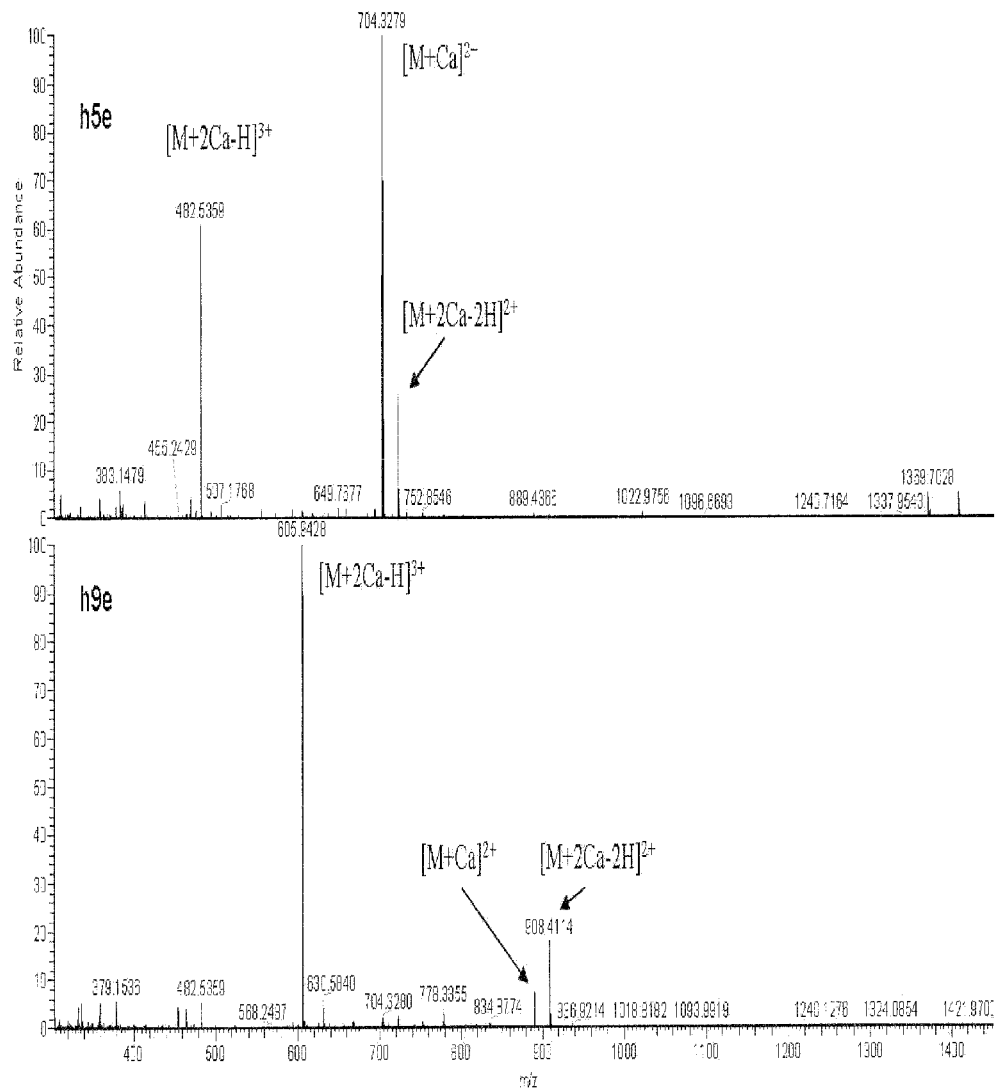
FIG. 10 shows mass spectrometry (MS) fragments of h5e and h9e.

Mass spectrometry (MS) experiments were conducted to identify possible precursors of the peptide assembly and nanofibre crossing in a Ca$^{2+}$ solution of h5e and h9e peptides (FIG. 10). Mass spectra obtained for both peptides were dominated by Ca$^{2+}$ adducts indicating high affinity of h5e and h9e to calcium. MS/MS experiments were conducted to gain insight on the mode of binding of calcium to h5e and h9e peptides. In agreement with earlier work, fragmentation of peptide molecules cationized on calcium produces a number of backbone fragments including y-, b-, a-, z- and c-ions. It has been demonstrated that the a-ion formation is promoted by calcium binding and occurs C-terminal to the Ca$^{2+}$ binding site. Examination of MS/MS spectra obtained for different calcium adducts of the h5e and h9e peptides (FIGS. 11-12) shows that in [M+Ca]$^{2+}$ ion calcium is most likely coordinated by the carboxyl group of the internal D residue is and solvated by the C-terminal D. Fragmentation behavior changed in an interesting way for [h9e+Ca]$^{2+}$ (FIG. 11). Cleavages indicative of Ca$^{2+}$ binding were observed in the SII and GDGPG (residues 13-17 of SEQ ID NO:11) regions, suggesting that although the first Ca$^{2+}$ is bound to the internal D residue, the second one is coordinated by serine. Differences in Ca$^{2+}$ binding capacity of the two peptides may explain why hydrogel formed in h9e but not h5e. Both h9 and eD$_2$ regions of h9e reacted with Ca$^{2+}$ for hydrogel formation, indicating that these two selected regions from the native sequence are particularly useful for this rational peptide design.

To experimentally confirm the specificity of the GSII (SEQ ID NO: 10) function and h9e, we synthesized other peptides by modifying the h9e sequence. When GSII (SEQ ID NO:10) was replaced with SII, PP$^D$, or IIVI (residues 6-9 of SEQ ID NO:26), these alternating peptides did not form a hydrogel with Ca$^{2+}$ at the same peptide concentration used for h9e (0.005M). However, the PP$^D$ segment changed the solubilities of these peptides in water, which may be due to the different assemblies of these peptides. Retaining the GSII (SEQ ID NO:10) region but substituting the FLIVI (SEQ ID NO: 1) segment of h9e with LLLLL (SEQ ID NO:2) resulted in the peptide forming a weak hydrogel (G': 21.6±0.3 Pa) in Ca$^{2+}$ solution. A similar hydrogel was observed in basic pH (G': 55.0+0.9 Pa) when the eD$_2$ of h9e was replaced with KKKKKKKKKK (SEQ ID NO:6).

Figure 13:
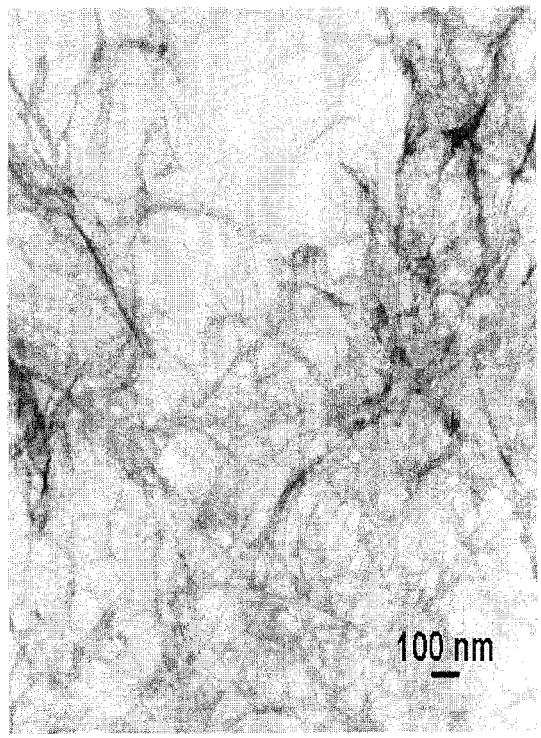
FIG. 13 shows a TEM image of h9e acidic hydrogel.
Figure 14:
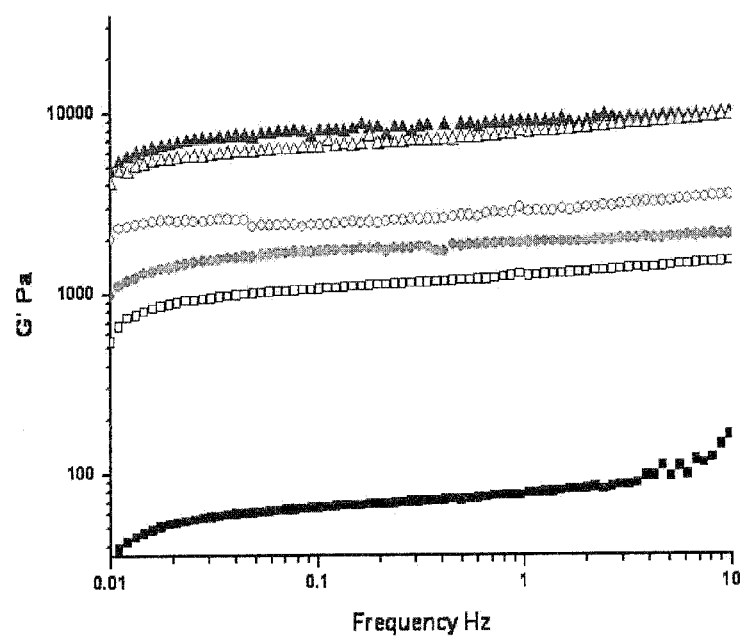
FIG. 14 shows the G' of h9e $Ca^{2+}$ and h9e acidic hydrogels. (solid: h9e $Ca^{2+}$ gel, open: h9e acidic gel. Peptide concentration: square: 0.0025M; circle: 0.005M; triangle: 0.01M)
Figure 15:
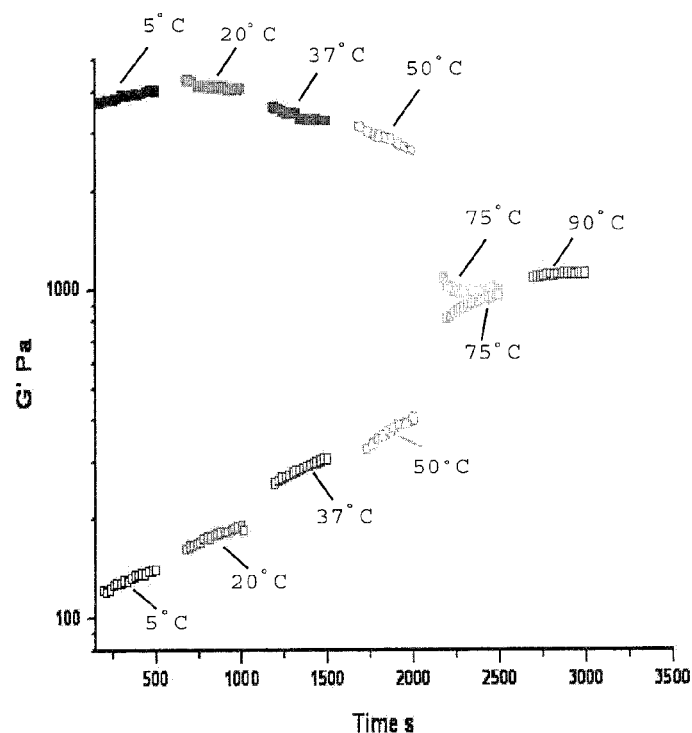
FIG. 15 shows the temperature profile test of h9e Ca²⁻ and h9e acidic hydrogels. (solid: h9e acidic hydrogel, open: h9e Ca²⁺ hydrogel)
Figure 16:
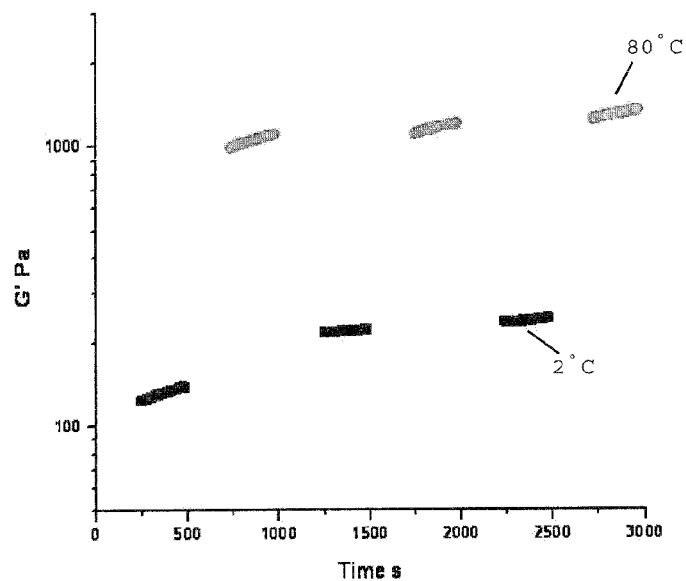
FIG. 16 shows the thermal reversible of G' of h9e Ca²⁺ hydrogel (black: 2° C., red: 80° C.)
Figure 17:
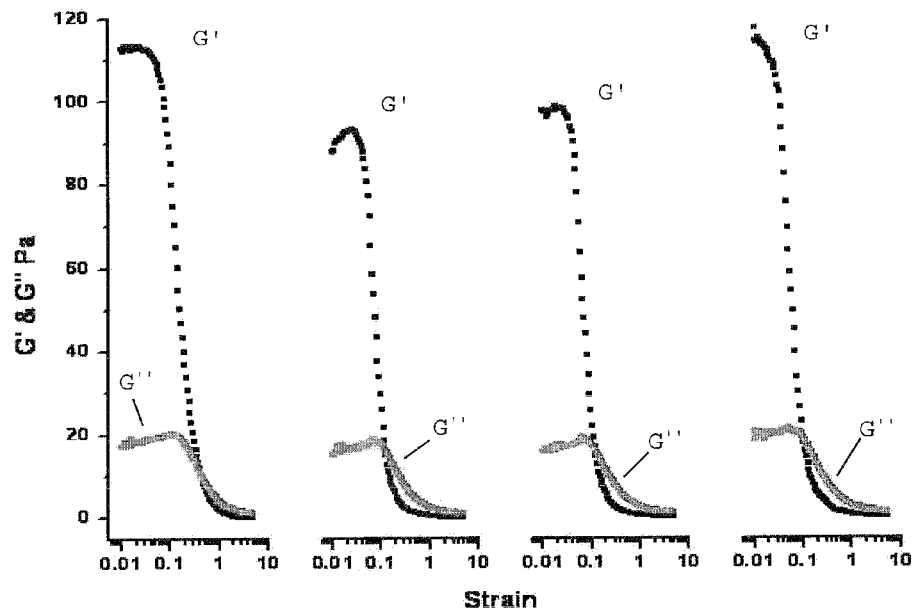
FIG. 17 shows the G' and G" values of h9e Ca²⁺ hydrogel under four amplitude sweep shear circles; time interval between each cycle was 10, 30 and 60 s, respectively (black: G'; red: G")

The h9e also formed a hydrogel in acidic pH. Originally, h5e and h9e were insoluble in water until the solution pH was adjusted to neutral or basic. When the pH was adjusted back to acidic, h5e precipitated but h9e became entangled and formed a hard hydrogel (FIG. 13) because of the flexibility of sequence due to GSII. A storage moduli (G') of the h9e acidic gel was about 10 times higher than that of the h9e Ca$^{2+}$ gel at 0.0025M peptide concentration (FIG. 14). The difference in G' between these two hydrogels became smaller as peptide concentration increased. For example, at 0.01 M, G' of the h9e Ca$^{2+}$ gel was about 9,000 Pa, which was even slightly higher than that of the h9e acidic gel. In a temperature profile test, G' of the h9e Ca$^{2+}$ hydrogel increased 10 fold as temperature increased from 5 to 90° C. and was thermal reversible within 2 to 80° C. (FIG. 15, FIG. 16). However, G' of the h9e acidic hydrogel decreased as temperature increased and reduced to 1,000 Pa at 75° C. The shear thinning and rapid recovery of mechanical strength was found only in the h9e Ca$^{2+}$ hydrogel (FIG. 17). Hydrogels underwent a serial amplitude sweep test. There was a short pause between every two test cycles. Gel became like pure liquid (G">G'≈0) under 500% strain oscillation. After 10 s of the first cycle, 75 to 80% of the hydrogel strength was recovered. Percentage of strength recovery increased as pause time increased and reached 100% recovery by 60 seconds. The multiple recovery properties and short recovery time demonstrate that the h9e Ca$^{2+}$ hydrogel would perform similarly to other reported recovering hydrogels.

Figure 18:
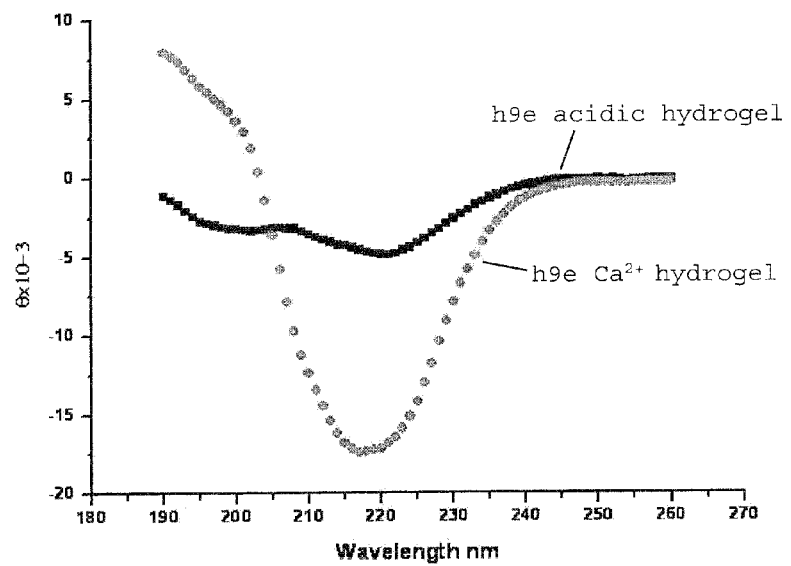
FIG. 18 shows the CD spectra of h9e Ca²⁺ and h9e acidic hydrogels (black: h9e acidic hydrogel, red: h9e Ca²⁺ hydrogel)

The turning segment, GSII, of h9e promoted hydrogel formation in both Ca$^{2+}$ solution and acidic pH conditions at water content more than 99.5%. Although h9e Ca$^{2+}$ hydrogel and h9e acidic hydrogel had the same sequence, they had distinct physical properties. The shear-thinning, rapid-strength-recovering h9e Ca$^{2+}$ hydrogel was used as an H1N1 influenza vaccine adjuvant. The results demonstrate two types of hydrogels with distinct mechanical properties created from a peptide with same primary structure. According to published studies, changing an amino acid in certain positions could result in peptide hydrogels with different mechanical strength, thermal responses and recovery properties because these changes in primary structures facilitated molecular folding and cross-linking of peptide fibres. The distinct properties of these two h9e hydrogels suggest that h9e molecules could undergo different molecular assembly and nanofiber cross-linking controlled by different external parameters despite having the same primary structure. The circular dichroism (CD) spectrum (FIG. 18) suggests that h9e adopted a significant β-structure in Ca$^{2+}$ solution, whereas a more random structure was detected in acidic condition.

Figure 19:
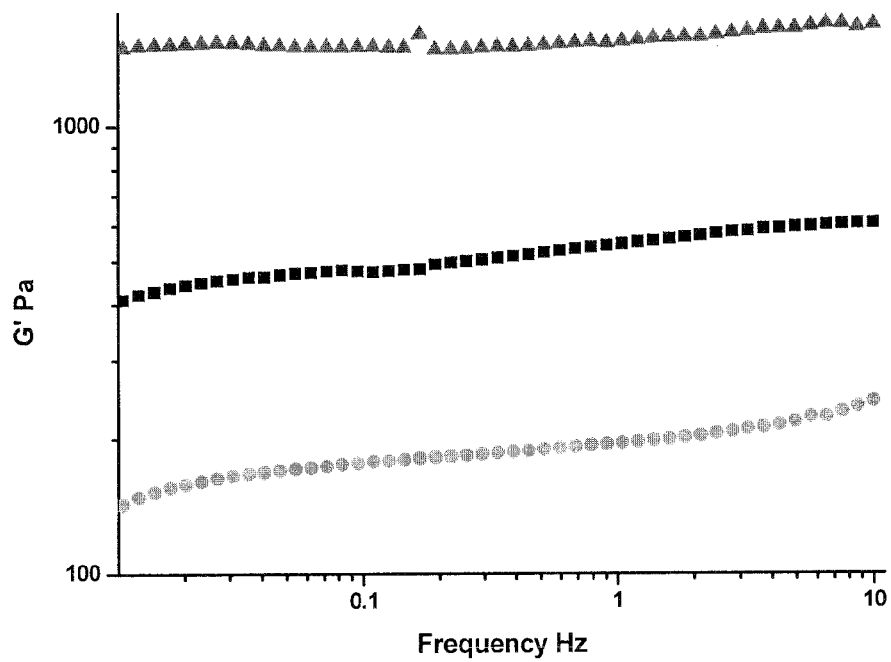
FIG. 19 is a graph of G' of h9e Zn²⁺ (triangle, top), Na⁺ (square, middle) and Mg²⁺ (circle, bottom) hydrogels. (peptide concentration 0.005M)
Figure 20:
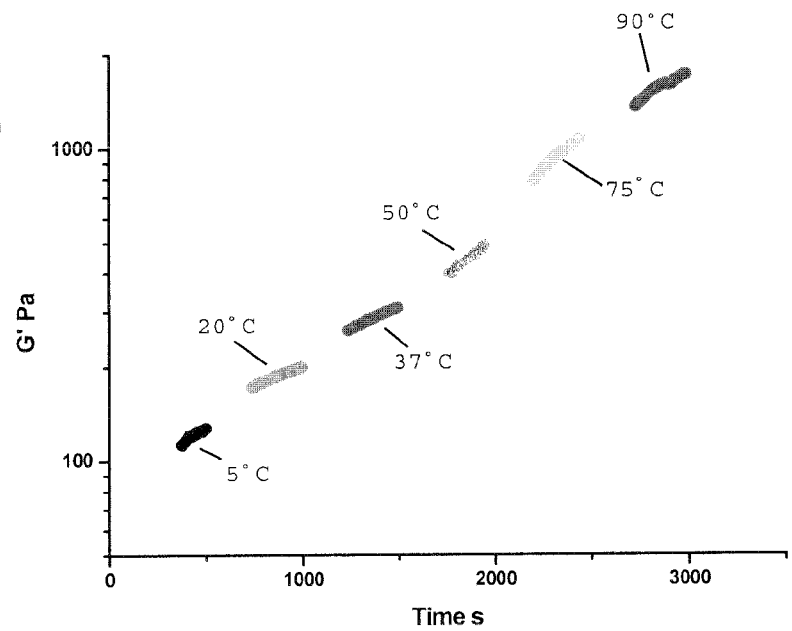
FIG. 20 is a graph of the temperature profile test of h9e Na⁺ hydrogel.
Figure 21:
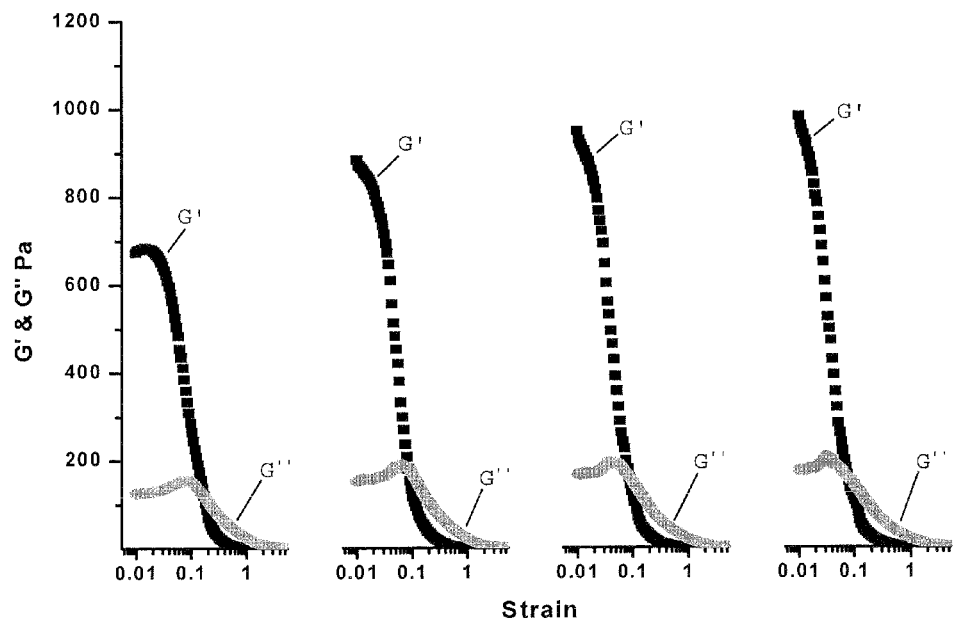
FIG. 21 is a graph of G' and G" values of h9e Na⁻ hydrogel under 4 amplitude sweep shear circles, time interval between each cycle was 10, 20 and 30 s, respectively (black: G'; red: G")
Figure 22:
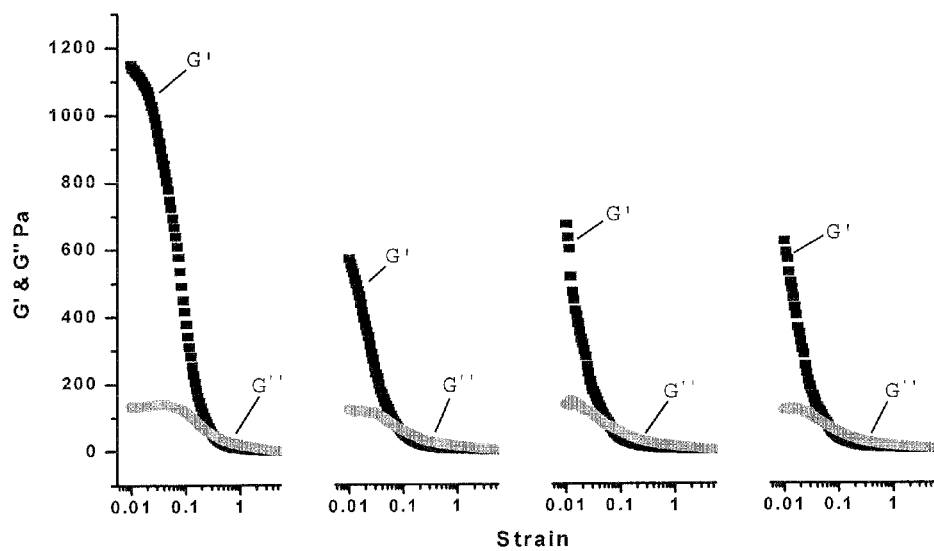
FIG. 22 is a graph of G' and G" values of h9e Mg²⁺ hydrogel under 4 amplitude sweep shear circles, time interval between each cycle was 10 s, 1 min and 5 min, respectively (black: G'; red: G")
Figure 23:
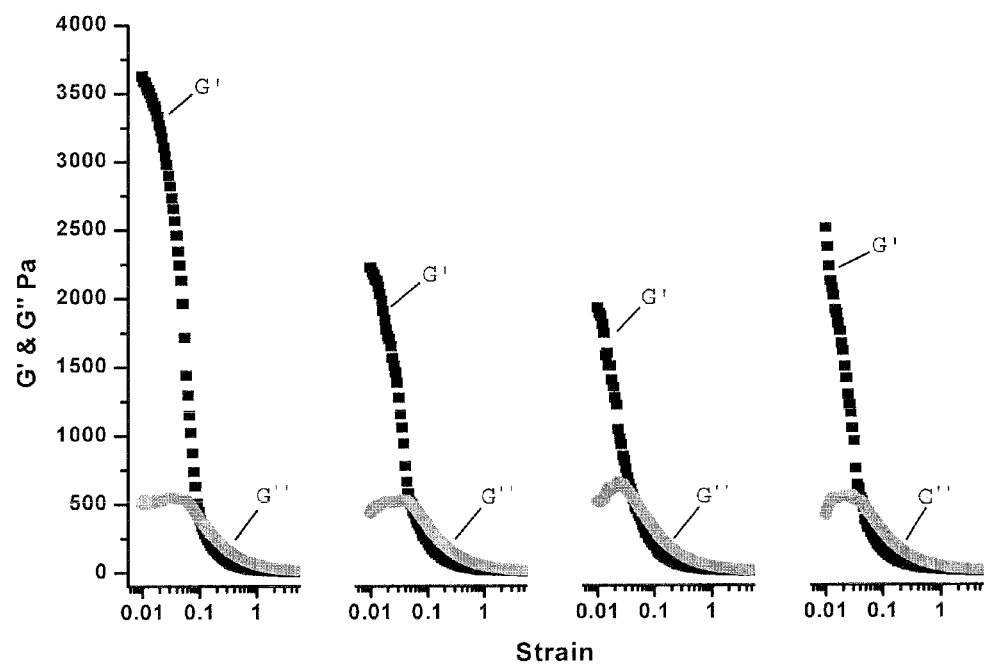
FIG. 23 is a graph of G' and G" values of h9e Zn²⁺ hydrogel under 4 amplitude sweep shear circles, time interval between each cycle was 10 s, 1 min and 5 min, respectively (black: G'; red: G")

Ions Na$^+$, Mg$^{2+}$, and Zn$^{2+}$ were also studied with h9e. In these three ion solutions, h9e formed hydrogels with different G' (FIG. 19). The h9e Na$^+$ hydrogel had physical properties similar to those of the h9e Ca$^{2+}$ hydrogel (FIGS. 20-21). However, h9e formed a soft hydrogel in Mg$^{2+}$ solution. In Zn$^{2+}$ solution, h9e formed a hard hydrogel as it did in h9e acidic gel. The rapid shear strength recovery property was not found in h9e Mg$^{2+}$ or h9e Zn$^{2+}$ hydrogels (FIGS. 22-23). The phenomenon of hydrogel formation of h9e in these ions requires further study.

Figure 24:
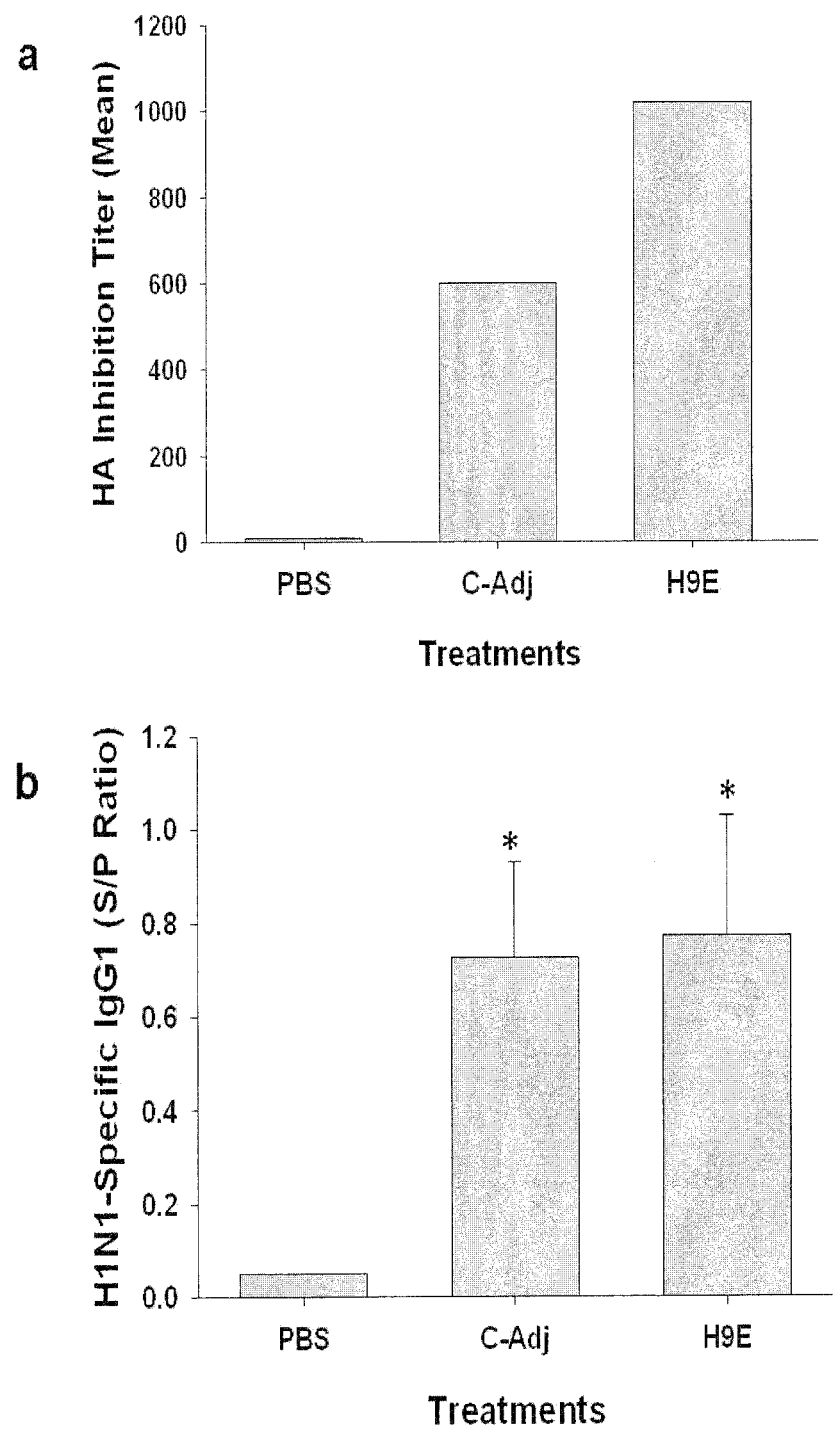
FIG. 24 is a) a graph of the application of h9e Ca²⁺ hydrogel as an adjuvant for H1N1 swine influenza virus killed vaccine in the mice in Example 1; b) a graph of the antibody response analysis (*p<0.03)

The h9e Ca$^{2+}$ hydrogel was applied as an adjuvant for vaccine antigen delivery and showed significantly higher efficiency than a commercial adjuvant. Mice immunized with h9e-adjuvanted vaccine or commercial vaccine did not show any abnormality and remained healthy before they were euthanized for sera collection. No injection site reaction (redness and swelling) was observed in vaccinated mice. Adjuvanticity of h9e Ca$^{2+}$ hydrogel was determined by immunizing mice with killed H1N1 swine influenza virus in the presence or absence of h9e Ca$^{2+}$ hydrogel and a commercial adjuvant, which was used as a positive control. As shown in FIG. 24a, the mean hemagglutination inhibition (HAI) titer in the sera from mice immunized with h9e Ca$^{2+}$ hydrogel and killed H1N1 virus antigen was 1020, which was about 70% higher the HAI titer of 600 observed in mice immunized with commercial vaccine. HAI activity was not detected in sera from mice treated with antigen in the absence of an adjuvant.

We also measured the effect of h9e Ca$^{2+}$ hydrogel on production of antigen-specific IgG1 antibody response. As shown in FIG. 24b, a positive antigen-specific antibody response (S/P ratio>0.4) was observed in mice immunized with antigen plus h9e Ca$^{2+}$ hydrogel or a commercial adjuvant. Mice immunized with killed antigen alone did not produce any detectable H1N1-specific IgG1 antibody (data not shown). There was no significant difference between h9e Ca$^{2+}$ hydrogel and commercial adjuvant in ability to induce an H1N1-specific IgG1 antibody response.

Figure 25:
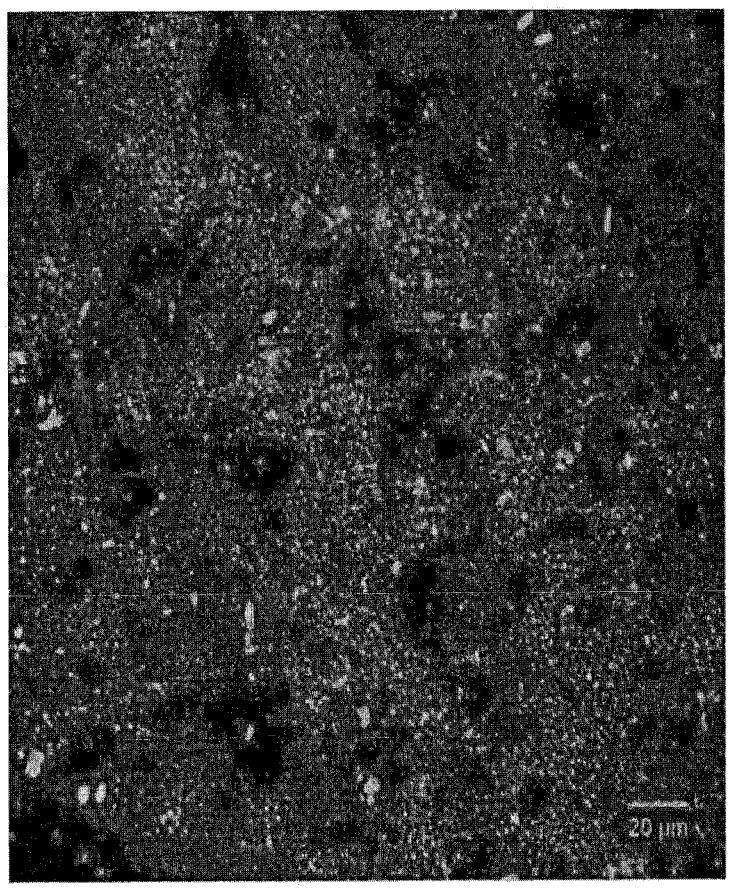
FIG. 25 is an LSCM image of h9e Ca²⁺ hydrogel.

Our studies provide the first evidence that h9e $Ca^{2+}$ hydrogel can be a safe, efficacious adjuvant for H1N1 swine influenza virus killed vaccine. Known adjuvants usually render adjuvanticity by directly stimulating antigen-presenting cells and other immune cells or by controlling the release of antigens from the injection site. The mechanism of h9e-mediated adjuvanticity remains to be determined. It is possible the hydrogel network controlled the antigen release, or the major segments of h9e, which were selected from native functional protein, might activate immune cells directly through a specific cell surface receptor, although the receptor for h9e has yet to be identified. It is equally possible that h9e and killed H1N1 viruses form nanoparticles. The laser scanning confocal microscope (LSCM) image of h9e $Ca^{2+}$ hydrogel (FIG. 25) shows microporous morphology (i.e., the nanofibres crossed each other and aggregated like nanoparticles at the crossing points). It is well established that microparticles can function as adjuvants to promote immune responses. For example, anionic microparticles coated with recombinant p55 gag protein from HIV-1 elicited strong cell-mediated immunity as well as antibody response in mice.

In summary, we used two native functional sequences from spider silk and calcium-binding motifs to design and synthesize novel peptides that formed nanofibers triggered by $Ca^{2+}$. However, $eD_2$ alone or tailored with hydrophobic segments (i.e., h5) was not able to form hydrogels. The turning function of GSII (SEQ ID NO:10) played a key role, altering the molecular assembly pathways of $h5GSII\ eD_2$ (h9e) for hydrogel formation. In acidic condition, h9e formed hard hydrogels that had a storage modulus (G') 10 times stronger than that of the hydrogel formed in $Ca^{2+}$ solution (at 0.0025 M peptide concentration). The G' of h9e acidic hydrogel was weakened upon heating, whereas the G' of h9e $Ca^{2+}$ hydrogel increased as temperature increased and was reversible in the temperature range of at 2 to 80° C. The h9e $Ca^{2+}$ hydrogel was shear thinning and had 100% recovery within 1 min. These distinct physical properties between h9e acidic hydrogel and h9e $Ca^{2+}$ hydrogel suggest that a peptide's molecular assembly pathways and degree of nanofibre cross-linking could be induced by external parameters such as pH and metal ions.

The adjuvant prepared using the h9e $Ca^{2+}$ hydrogel was biologically safe, improved immune response on killed H1N1 virus antigen by ~70% and had a similar ability to induce an H1N1-specific IgG1 antibody response compared with an oil-based commercial adjuvant. Our studies provide the first evidence that h9e can be a safe and efficacious adjuvant for H1N1 swine influenza virus vaccine. Application potentials include, but are not limited to, adjuvants that can be formulated with killed and attenuated microbes (i.e., H1N1, other Influenza, H3N1, H5N1) in the forms of injections or microgel encapsulations, or other delivery approaches.

Example 3

PRRS Live Vaccine Adjuvant Study

1. Vaccine Preparation

A stock solution of h9e peptide (concentration 1.75% by weight in water) was prepared. For the active agent, 2X Ingelvac PRRS MLV (Boehringer Ingelheim Vetmedica, St. Joseph, Mo.) was used. The vaccine was rehydrated by adding half of the contents of the accompanying liquid diluent to the vial containing the virus. Medium was then prepared by adding 0.3 ml bovine serum to 7.2 ml MEM medium (ion source). Next, 5 ml of the peptide stock solution was added to the medium and mixed well. This was then mixed with the vaccine solution. The final concentration of h9e as adjuvant was 0.35% by weight, and the final concentration of serum was 0.012% by weight.

Vaccines were also prepared using a commercially-available adjuvant, Montanide™ Gel 01 (aqueous polymeric gel veterinary adjuvant, Seppic Inc., Fairfield, N.J.), or a published peptide hydrogel, designated herein as A1/2 (SEQ ID NO:28, corresponding to the N-terminal region of mineral directing gelator (MDG) 1; Gungormus, et al., *Biomaterials* 31 (2010) 7266-7274).

2. Animals and Vaccination Study

55 PRRSV serum negative pigs were initially divided into 5 vaccination groups and vaccinated on Day 0. The pigs were then challenged on day 28 with a control (no challenge) or one of two PRRSV strains: PRRSV VR-2332, the parental strain of the Ingelvac PRRS MLV vaccine, or PRRSV MN 184a, a highly pathogenic isolate able to induce severe clinical signs that is heterologous to both PRRSV VR-2332 and the vaccine virus. The challenge dose of VR-2332 was 2-fold that of MN184a. The test groups are outlined in the Table below.

| Experimental Outline | | | |
|---|---|---|---|
| | | Challenge Group | |
| Vaccine Group | None | VR2332 | MN184a |
| None/naive pigs | Group 1 | Group 2 | Group 3 |
| MLV PRRSV | — | Group 8 | Group 4 |
| MLV + h9e | — | Group 9 | Group 5 |
| MLV + A1/2 | — | Group 10 | Group 6 |
| MVL + Gel01 | — | Group 11 | Group 7 |

At Day 0, all pigs were weighed, and weight was monitored weekly and recorded on Days 7, 14, 21, and 28. Prior to vaccination a blood sample was taken from each pig for serum isolation. Body temperature and clinical signs were monitored daily and recorded. Blood was collected on Days 7, 14, 21, and 28 after vaccination for serum. Blood was collected weekly after challenge. On Day 42, the pigs were euthanized and necropsy was performed on all pigs to collect blood, lung, tonsil and lymph node samples for PBMC, serum and histopathology analysis.

3. Data Analysis

A. Body Weight Gain Performance

Figure 26:
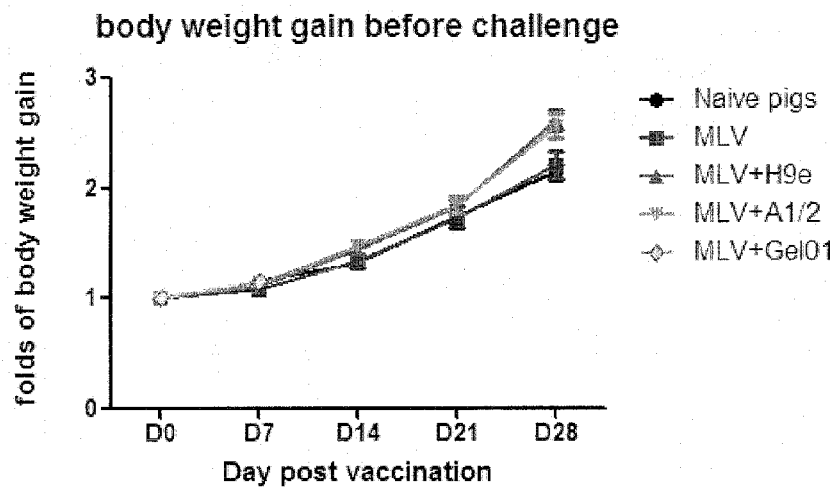
FIG. 26 is a graph of body weight gain in pigs from Example 3 before viral challenge.
Figure 27:
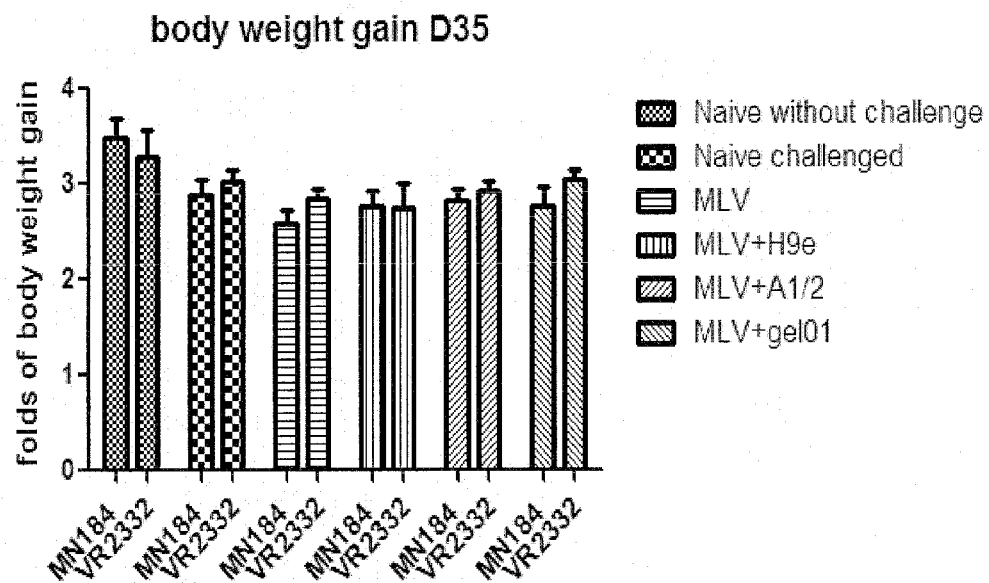
FIG. 27 is a graph of body weight gain in pigs from Example 3 on Day 35.
Figure 28:
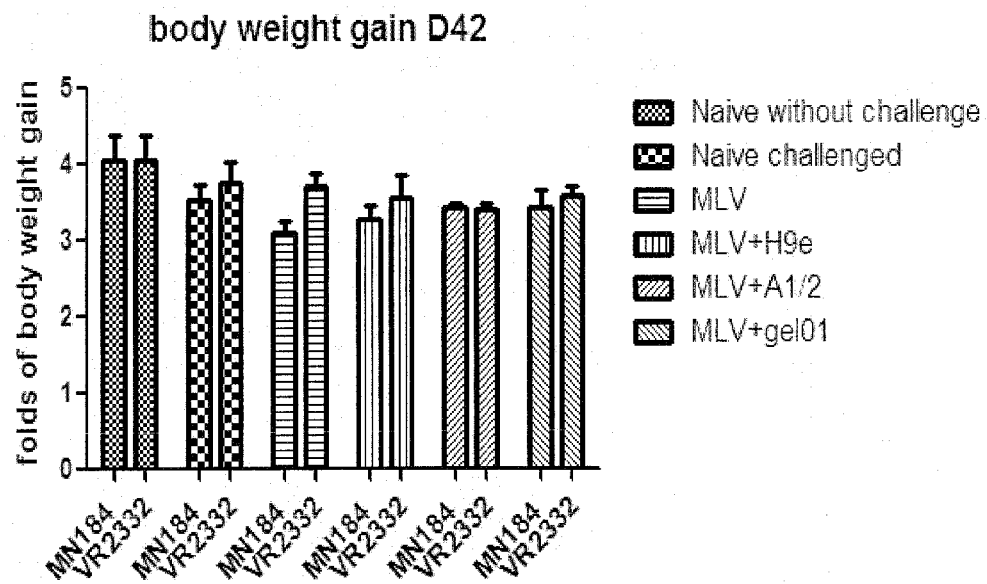
FIG. 28 is a graph of body weight gain in pigs from Example 3 on Day 42.

Vaccination with adjuvant did not influence pig body weight gain performance before the viral challenged. The virus challenged pigs showed slightly lower body weight gain performance compared to the unchallenged pigs. There was no difference among challenged groups. The results are shown in FIGS. 26-28.

B. Body Temperature Change

Figure 29:
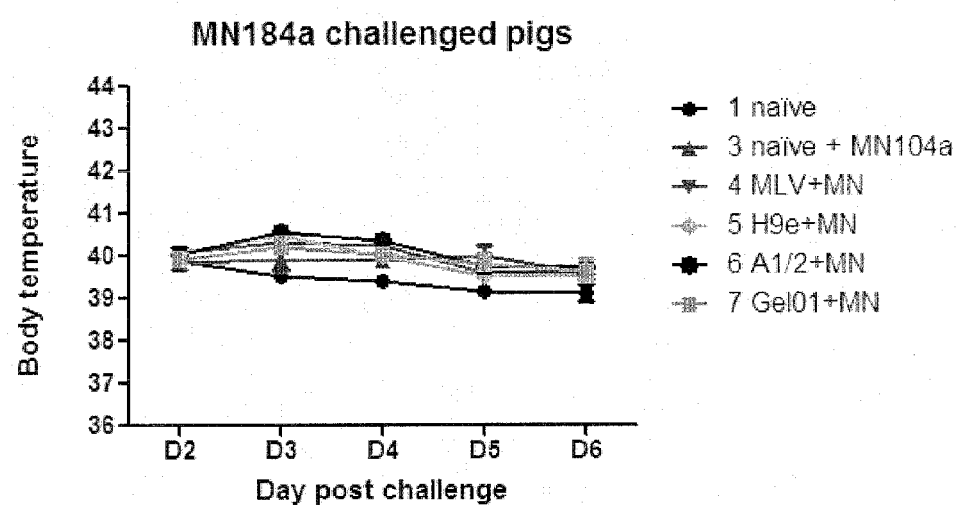
FIG. 29 is a graph of body temperature in MN184a challenged pigs from Example 3.
Figure 30:
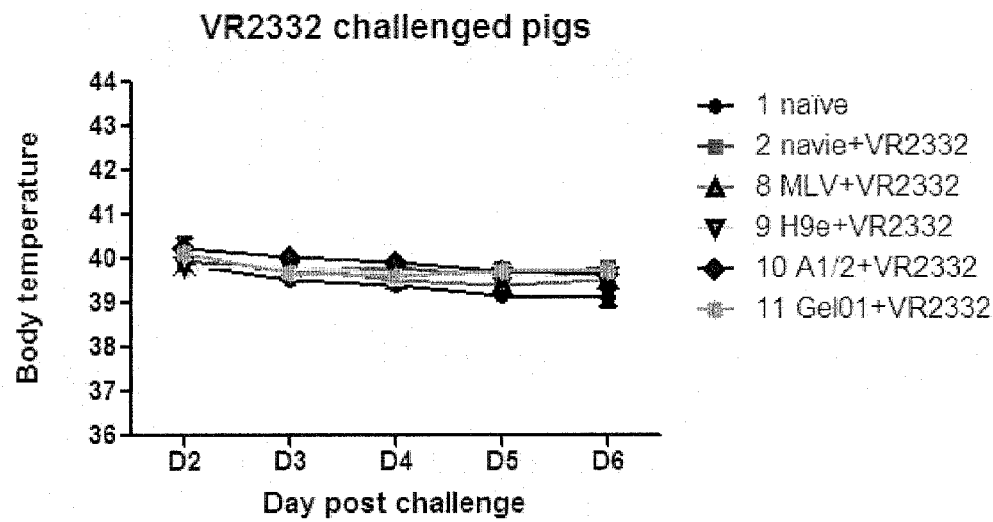
FIG. 30 is a graph of body temperature in VR-2332 challenged pigs from Example 3.

The average body temperature of pigs challenged with MN184a was 1° C. higher than with VR2332. There was no difference among each challenged group. The results are shown in FIGS. 29-30.

C. Dynamic Viremia after Vaccination

Figure 31:
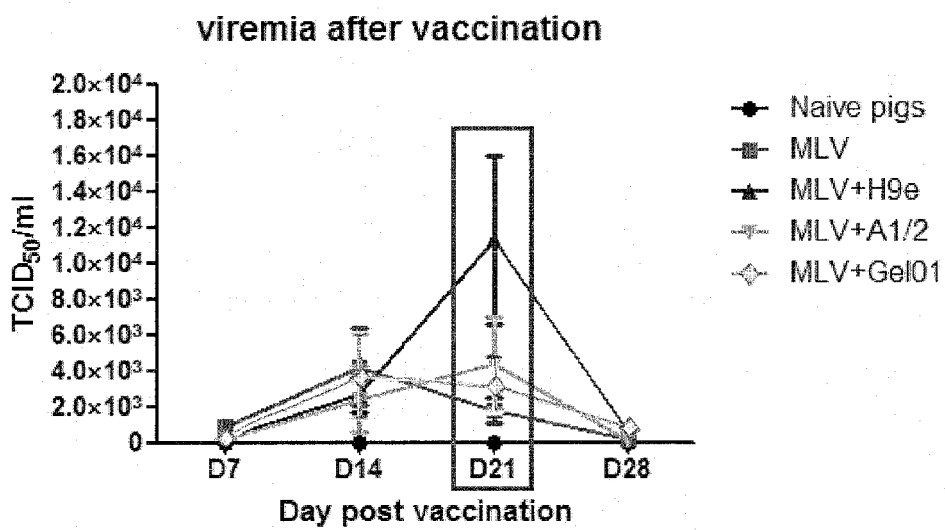
FIG. 31 is a graph of the dynamic viremia after vaccination in pigs from Example 3.

After vaccination, viremia started to increase to the maximum of $5×10^3$ $TCID_{50}$/mL, and then began to drop to the neglected level at Day 28. Compared to the MLV groups, viremia in the h9e-adjuvanted group started to increase and reached the maximum of $1×10^4$ $TCID_{50}$/mL (2 folds of MLV group on Day 28), and then begun to drop to the neglected level at Day 28. As for the other groups adjuvanted with A1/2 or Gel01, there was no difference compared to the MLV group. The results are shown in FIG. 31.

D. Dynamic Viremia after Challenge

Figure 32:
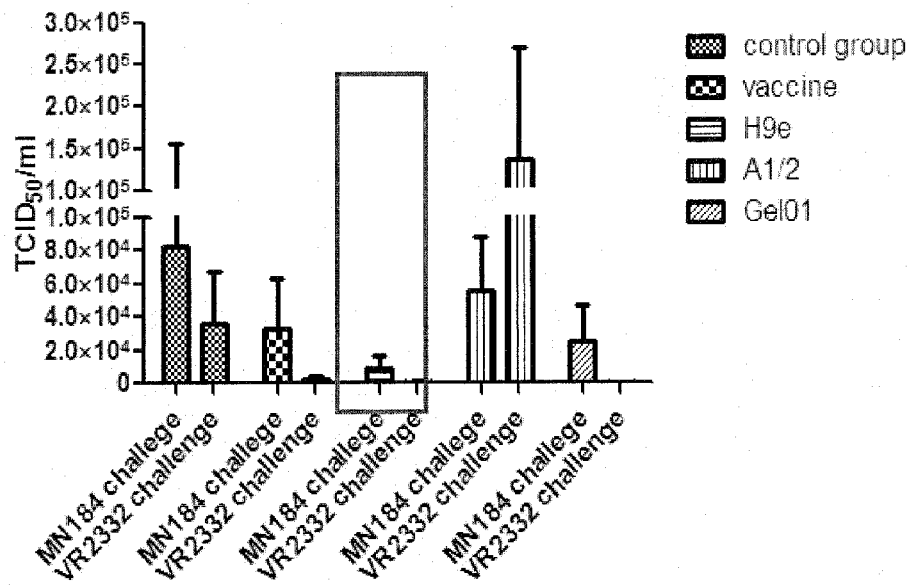
FIG. 32 is a graph comparing the dynamic viremia on Day 35 in pigs challenged with MN184a and VR-2332 from Example 3.
Figure 33:
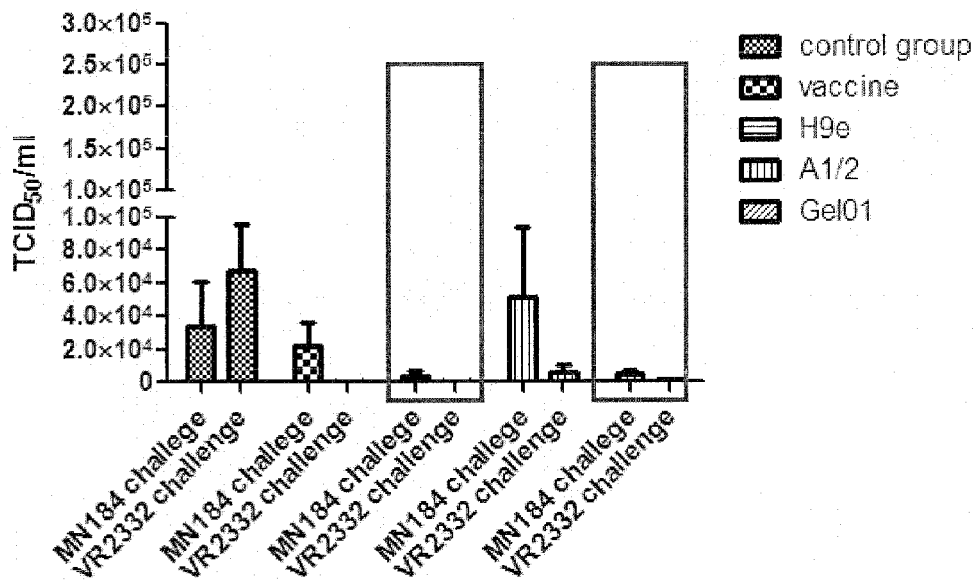
FIG. 33 is a graph comparing the dynamic viremia on Day 42 in pigs challenged with MN184a and VR-2332 from Example 3.

After challenge, the viremia was lower in the h9e-adjuvanted groups and the Gel01 groups, but not in the A1/2 groups. Two weeks after challenge, viral titers began to drop in all groups. Pigs challenged with MN184a heterologous PRRS virus showed higher viremia compared to the homologous VR2332 challenge. The results are shown in FIGS. 32-33.

E. Dynamic of IDEXX ELISA Ab Titer after Vaccination

Figures 34, 35:
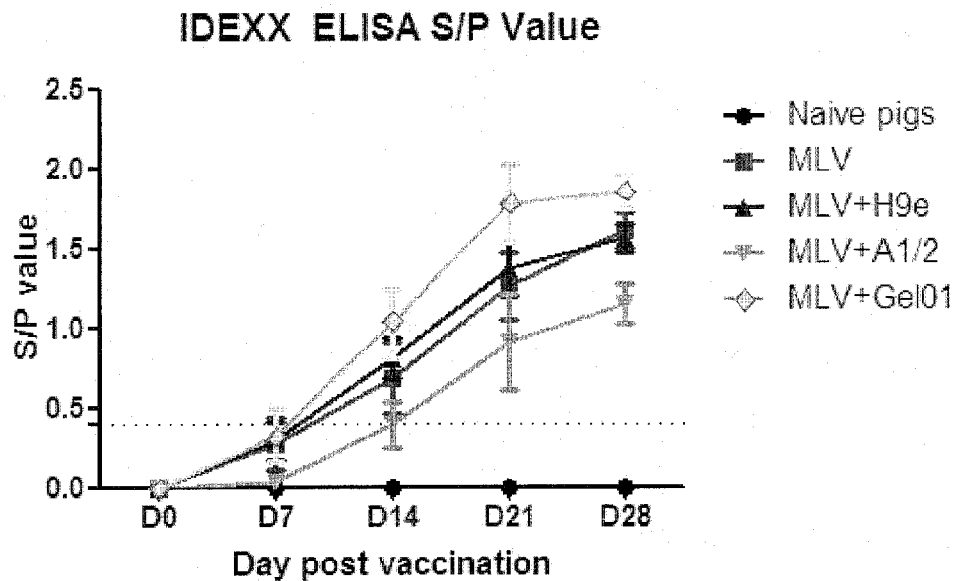
FIG. 34 is a graph of the IDEXX ELISA S/P value after vaccination in Example 3.
FIG. 35 is a table showing the number of pigs with positive serum in each group from Example 3.

After vaccination, more pigs converted PRRSV Ab positive in the h9e group on Day 14 (9 out of 10), as compared to the MLV only group (5 out of 10). The Gel01 group had the highest ELISA Ab titer. The A1/2 group had the lowest Ab titer compared to the other three groups. The results are shown in FIG. 34 and the table in FIG. 35.

F. Dynamic IDEXX ELISA Ab Titer after Virus Challenge

Figure 36:
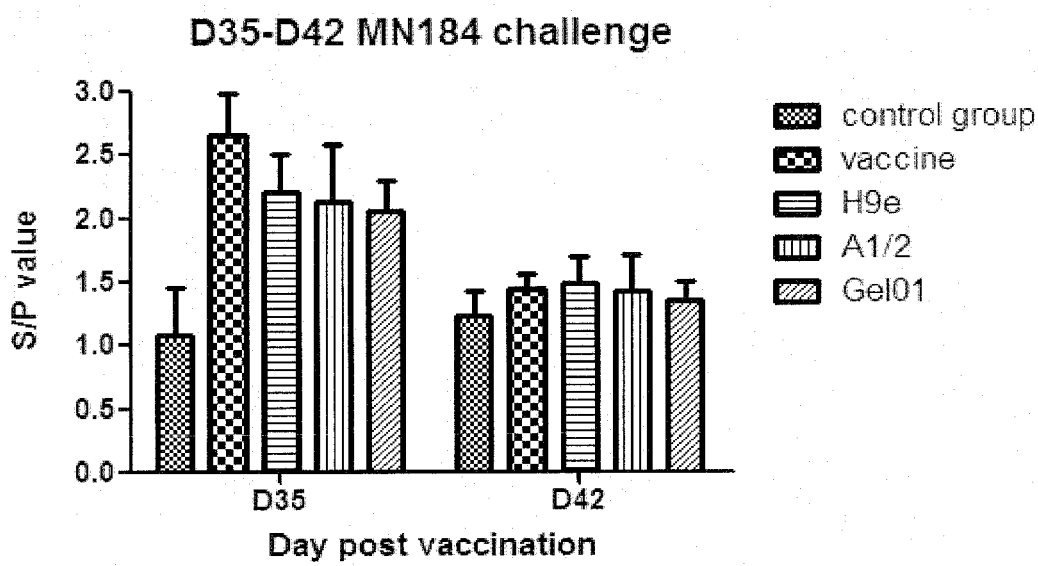
FIG. 36 is a graph of the dynamic of INDEXX ELISA Ab titer after challenge with MN184a in Example 3.
Figure 37:
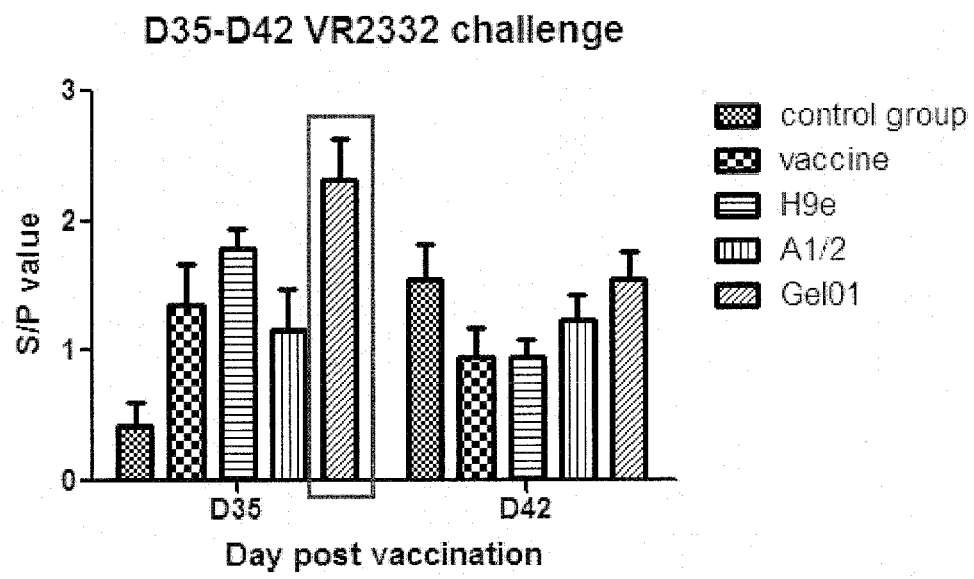
FIG. 37 is a graph of the dynamic of INDEXX ELISA Ab titer after challenge with VR-2332 in Example 3.

After MN184a challenge, the Ab titer was not significantly different among each group. After VR2332 challenge, the Gel01 group still had the highest titer. However, the h9e-adjuvanted group had a slightly higher Ab titer than the MLV-only group after one week and became the same after 2 weeks post-challenge. Interestingly, five out of five pigs converted to serum positive when challenged, with MN184a compared to only two out of five pigs in the VR2332-challenged group. The results are shown in FIGS. 36-37.

G. Virus Neutralizing Ab Titer to VR2332 and MN184a Challenge

Figure 38:
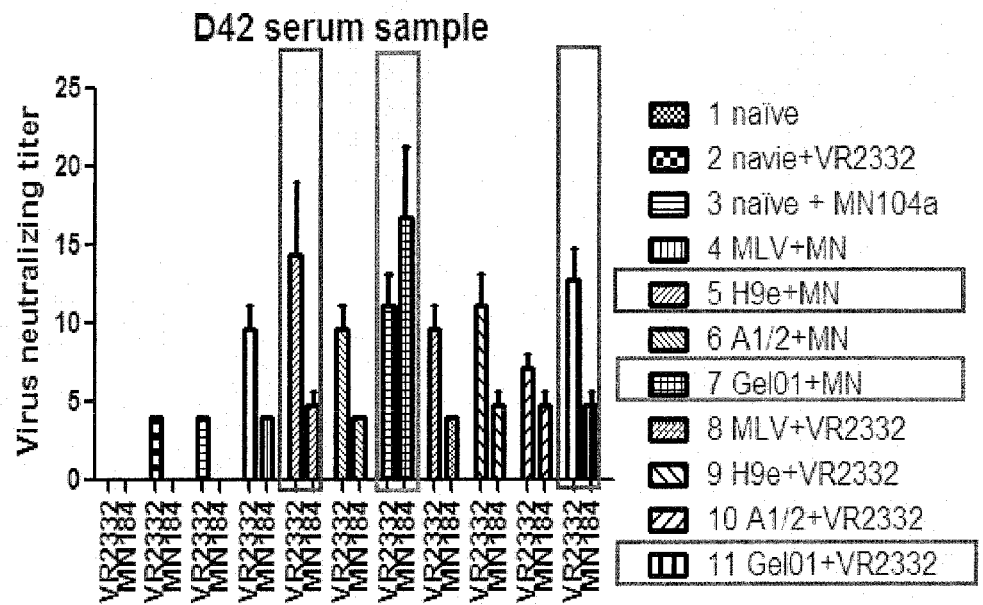
FIG. 38 is a graph of the VNT after challenge with VR-2332 and MN184a in Example 3.

Pigs in the h9e-adjuvanted groups and Gel01-adjuvanted groups developed the highest virus neutralizing titer (VNT) to VR2332 and MN184a virus. Pigs in the Gel01-adjuvanted group then challenged with MN184a had even higher VNT to MN184a (middle box) than VR2332 (right box). In contrast, pigs in the h9e-adjuvanted group challenged with MN184a and VR2332 developed higher titer to homologous VR2332 challenge than MN184a virus challenge (left box). The results are shown in FIG. 38.

H. Frequency of IFNr-Secreting Cells in PBMCs

Figure 39:
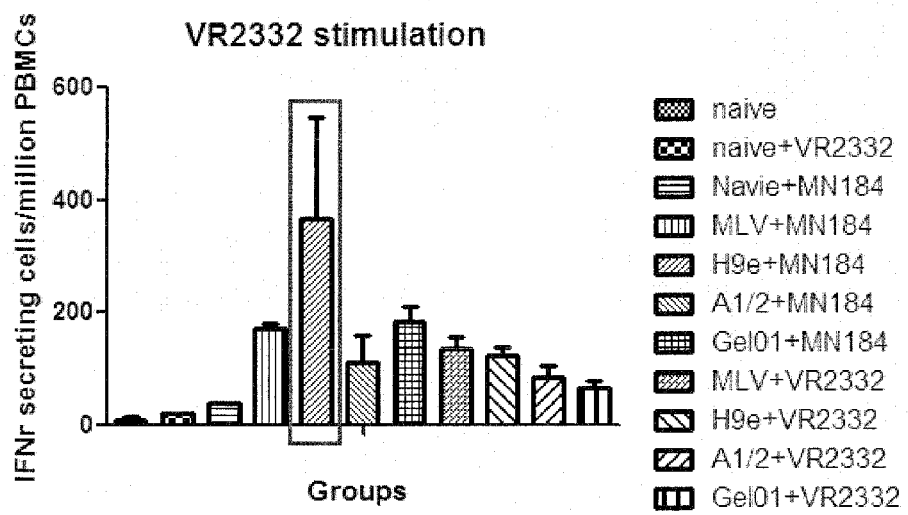
FIG. 39 is a graph of the frequency of IFNr-secreting cells in PBMCs after VR-2332 stimulation.
Figure 40:
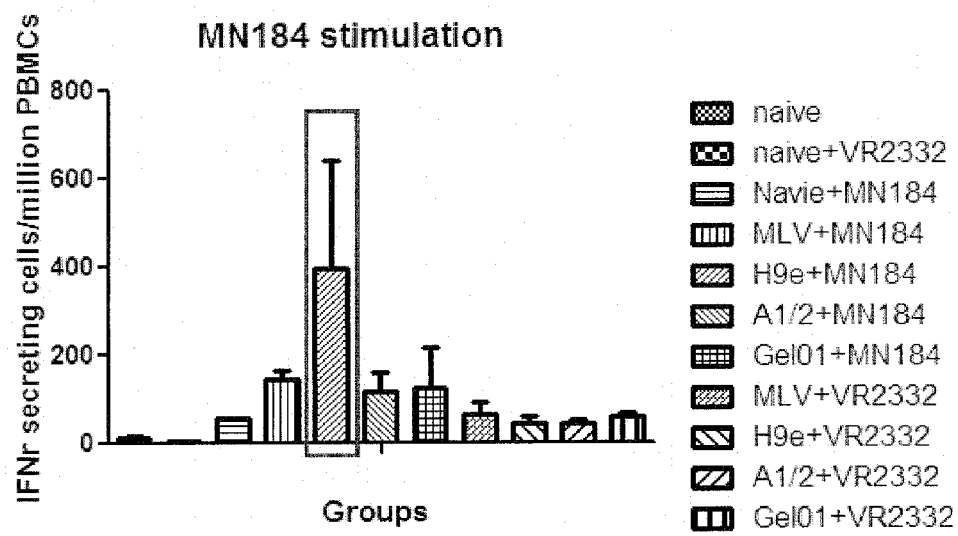
FIG. 40 is a graph of the frequency of IFNr-secreting cells in PBMCs after MN184a stimulation.
Figure 41:
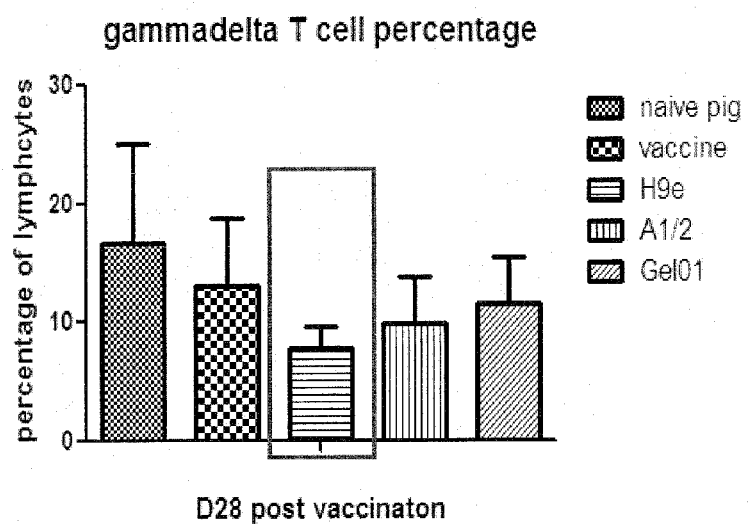
FIGS. 41-48 are graphs of different lymphocyte populations in blood at Day 28 from Example 3.
Figure 42:
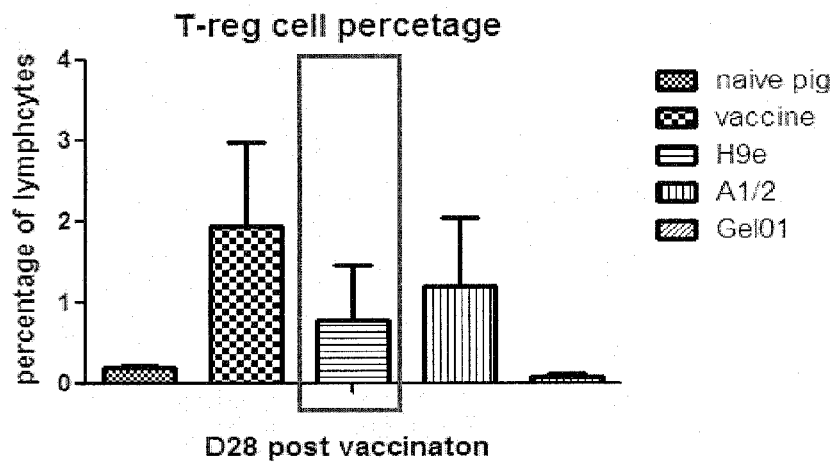
Figure 43:
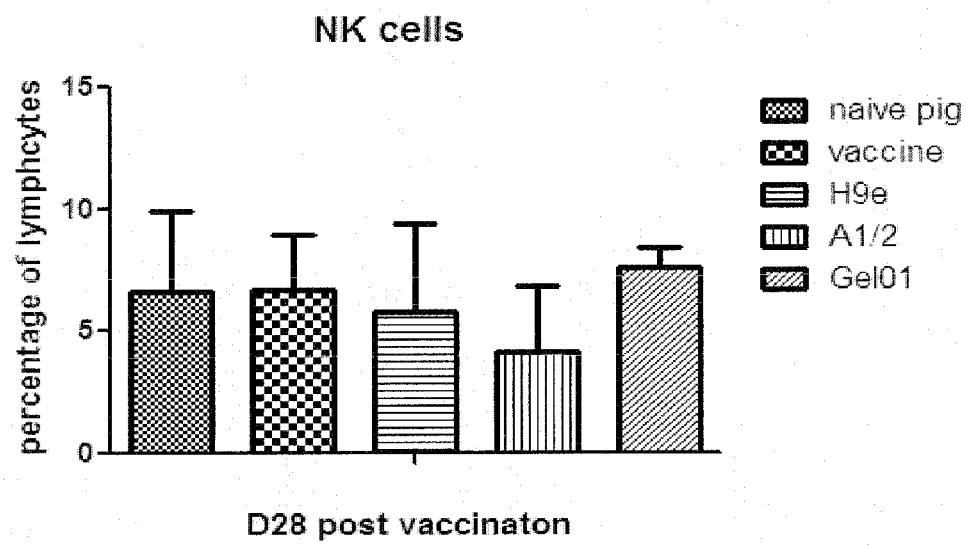
Figure 44:
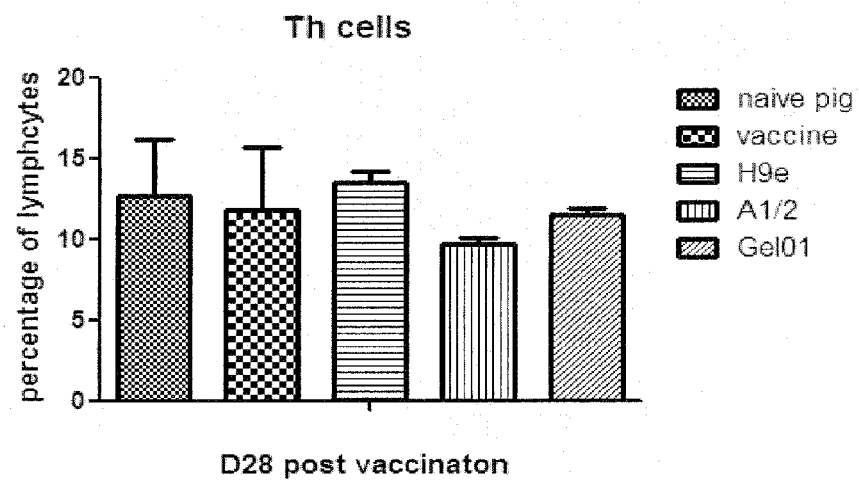
Figure 45:
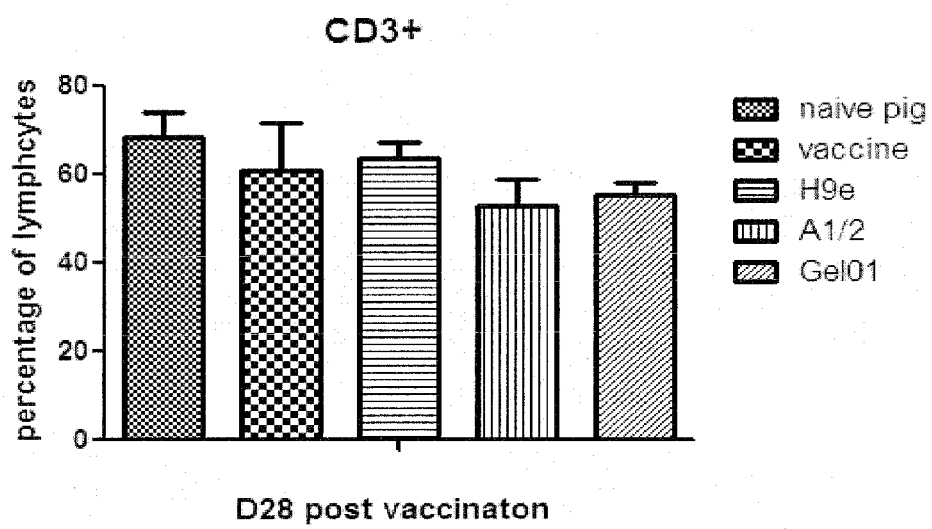
Figure 46:
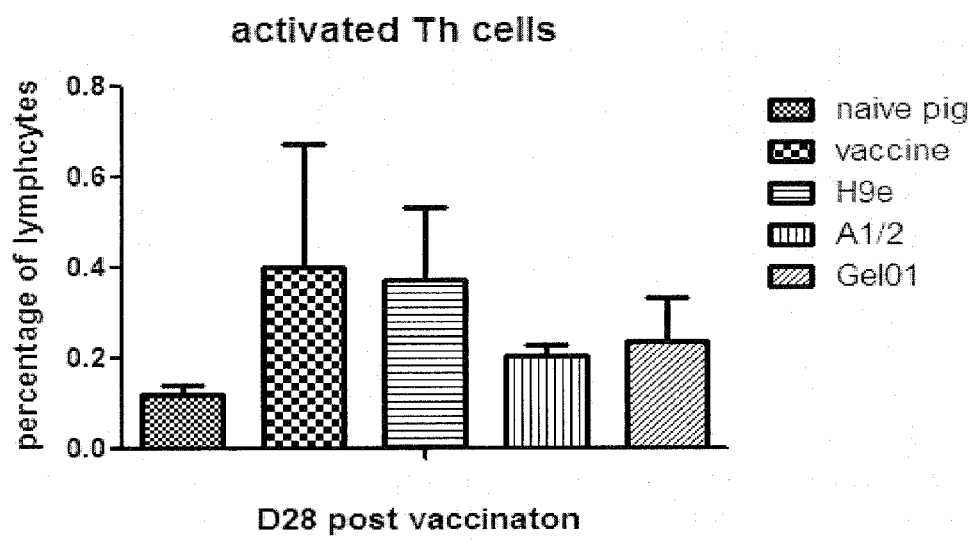
Figure 47:
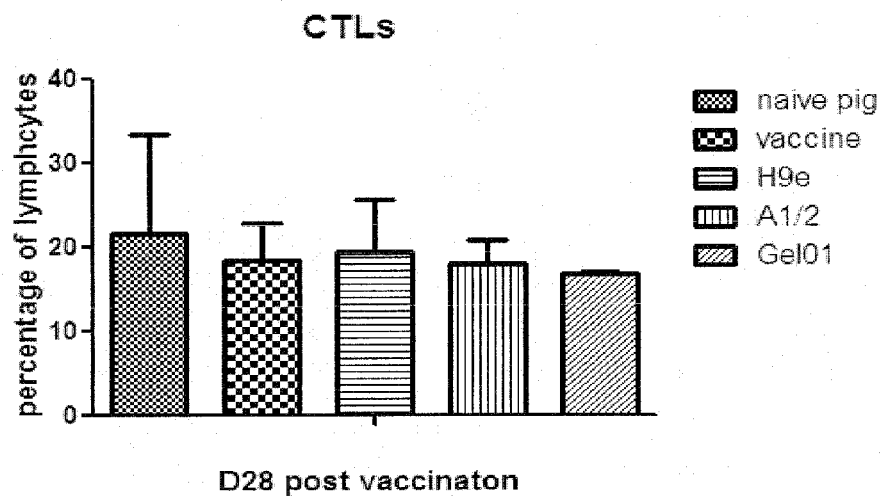
Figure 48:
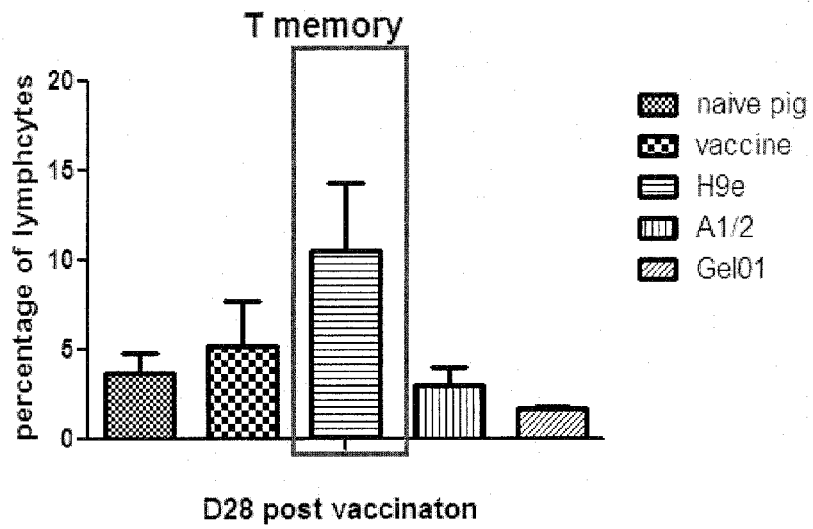
Figure 49:
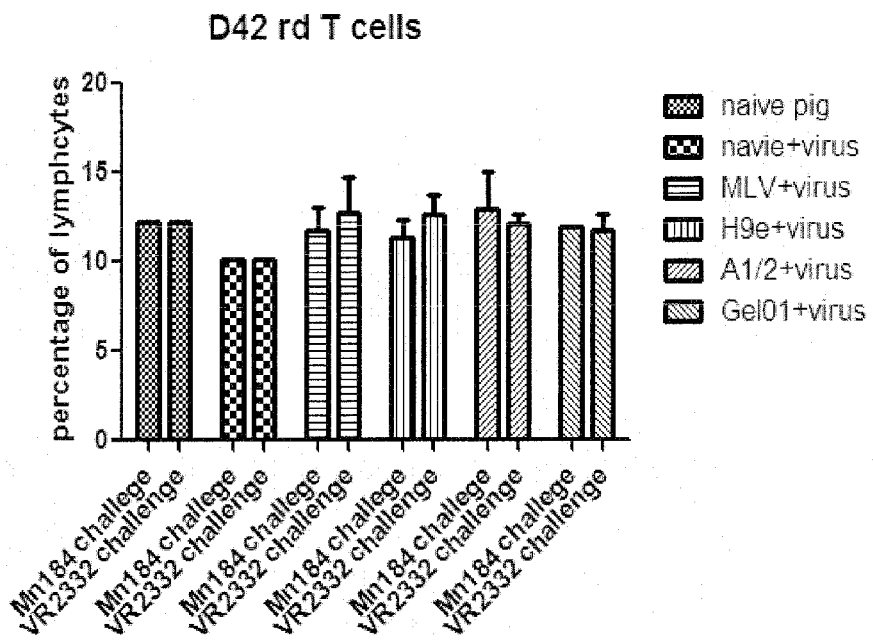
FIGS. 49-56 are graphs of different lymphocyte populations in blood at Day 42 from Example 3.
Figure 50:
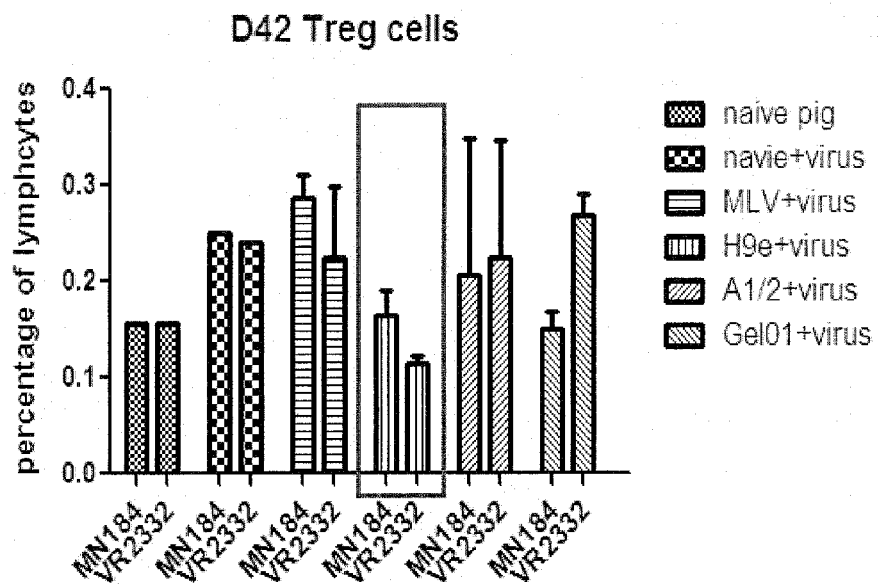
Figure 51:
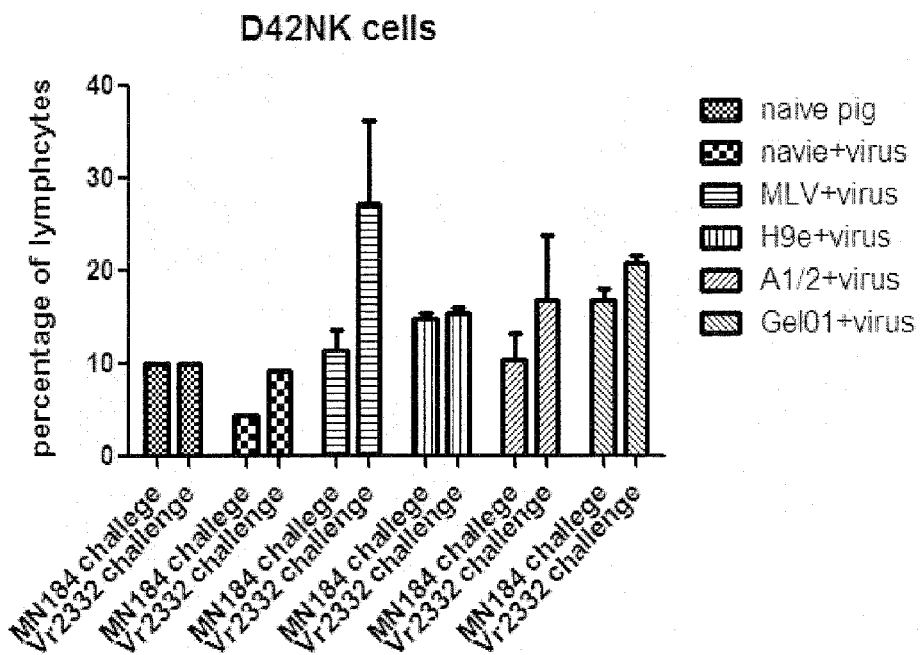
Figure 52:
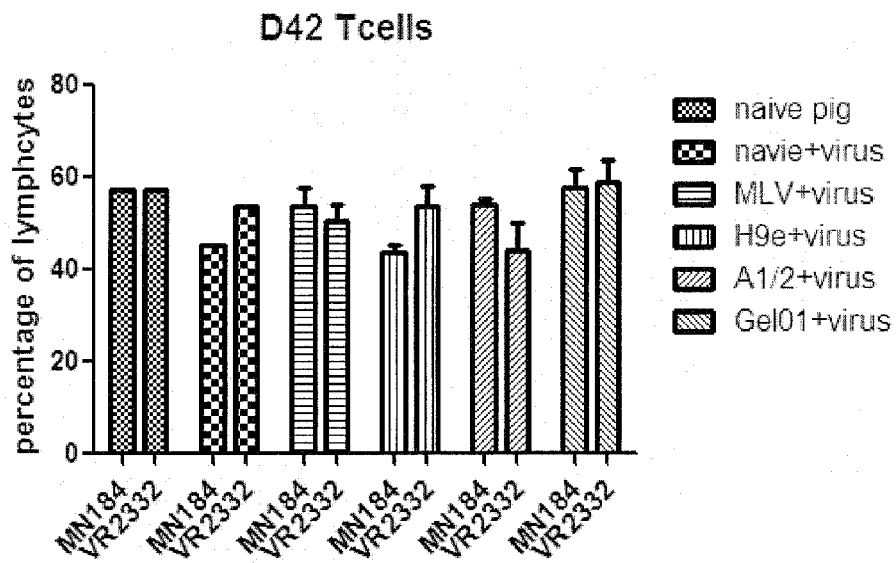
Figure 53:
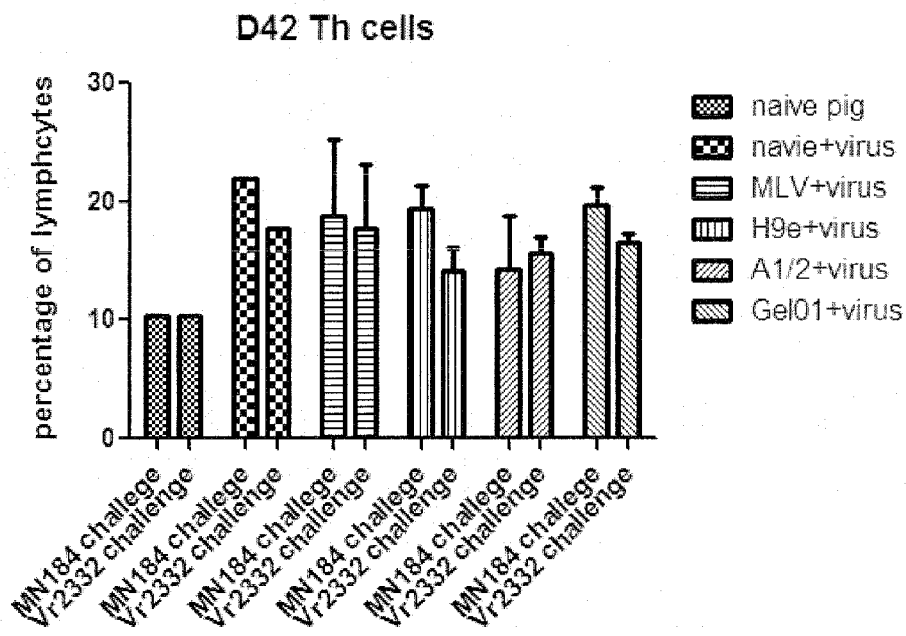
Figure 54:
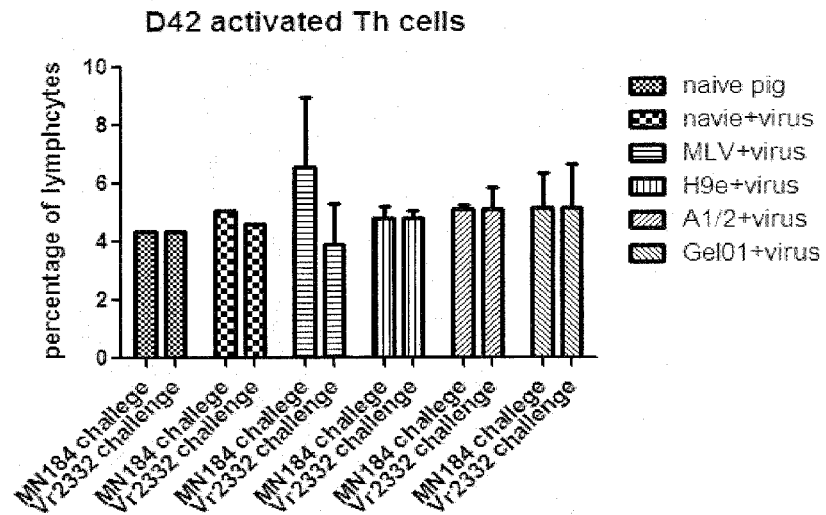
Figure 55:
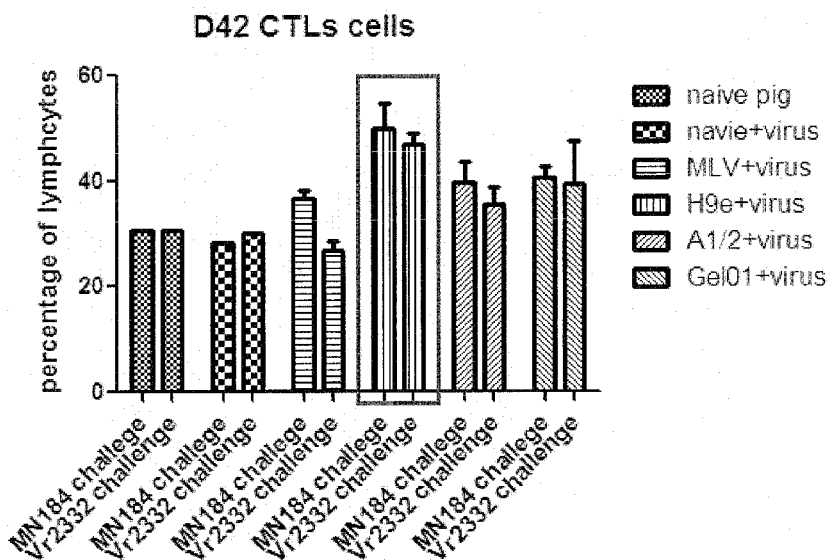
Figure 56:
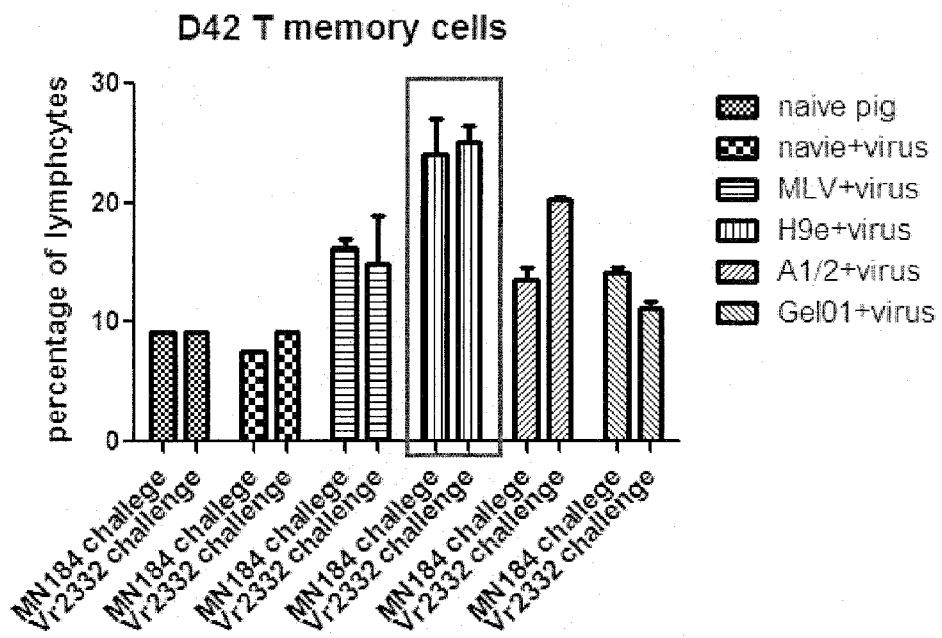
Figure 57:
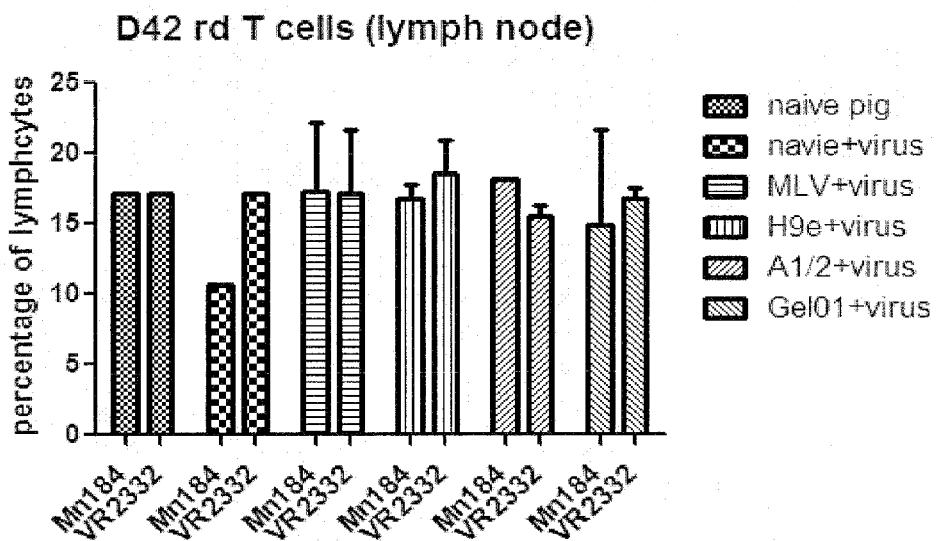
FIGS. 57-64 are graphs of different lymphocyte populations in lymph nodes at Day 42 from Example 3.
Figure 58:
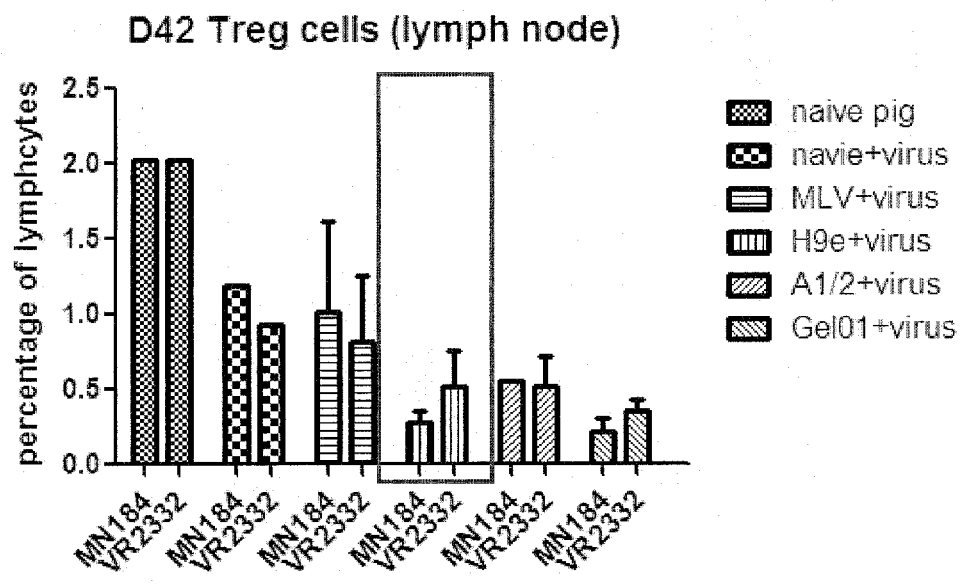
Figure 59:
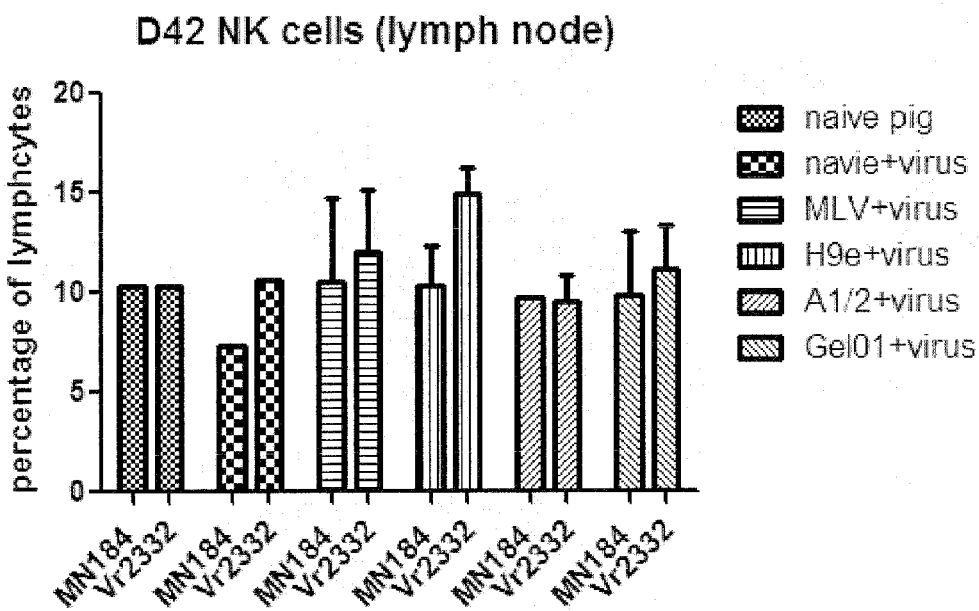
Figure 60:
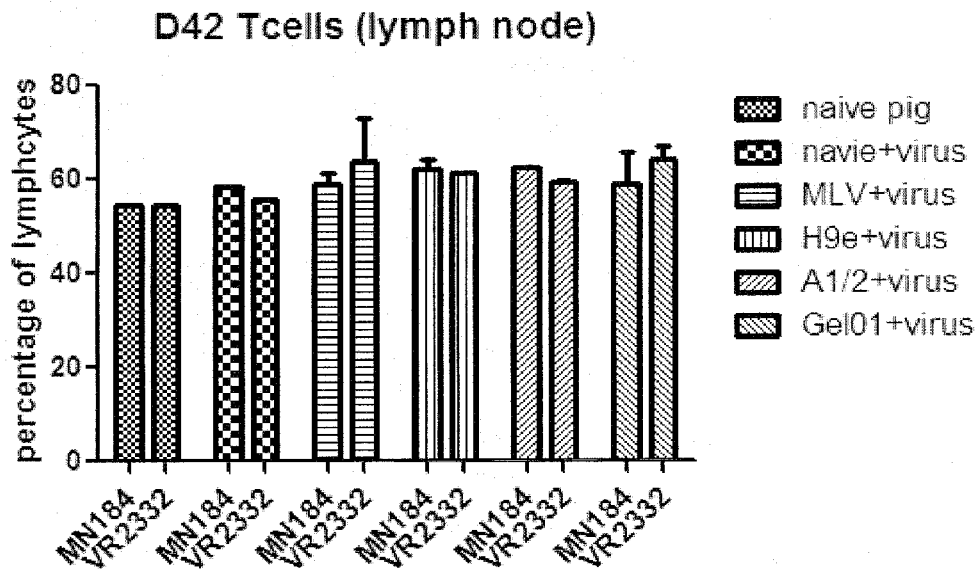
Figure 61:
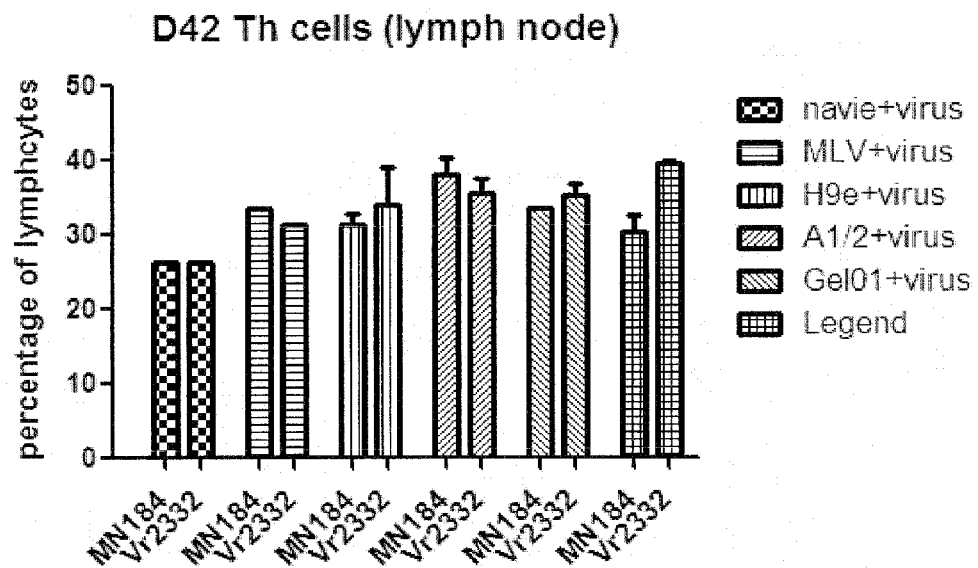
Figure 62:
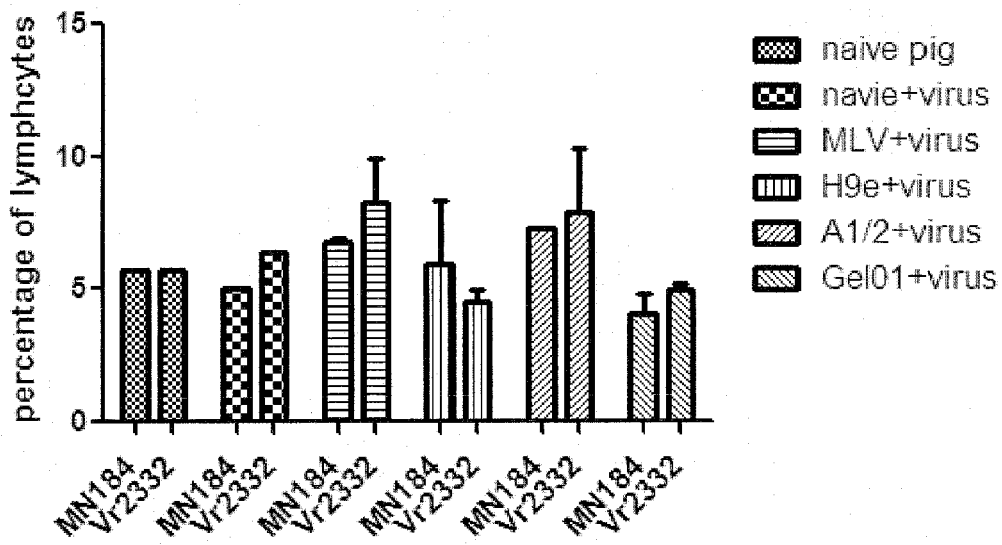
Figure 63:
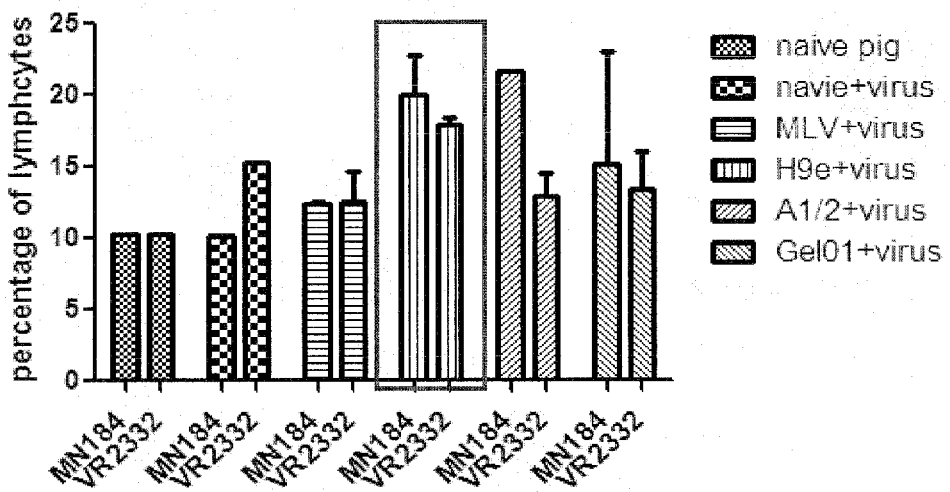
Figure 64:
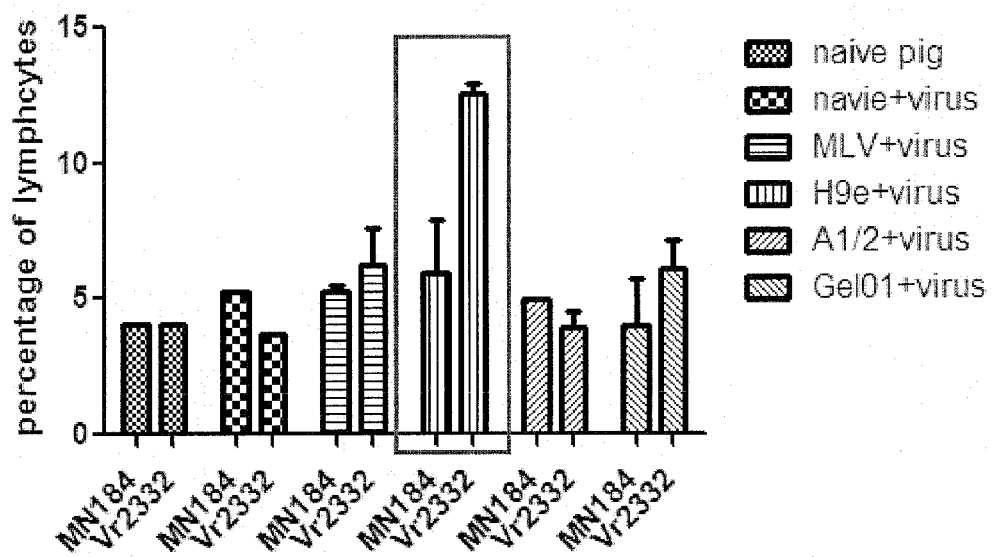
Figure 65:
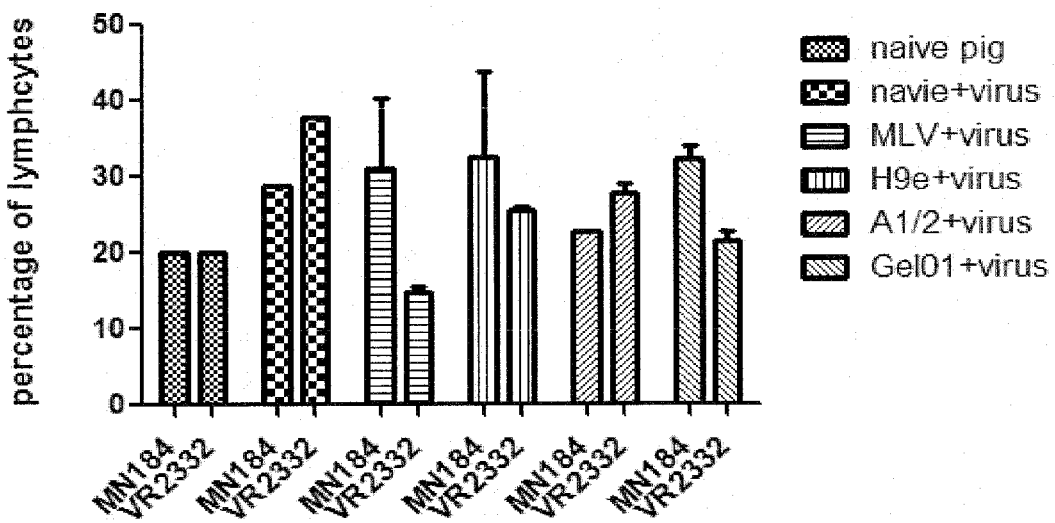
FIGS. 65-72 are graphs of different lymphocyte populations in lung samples at Day 42 from Example 3.
Figure 66:
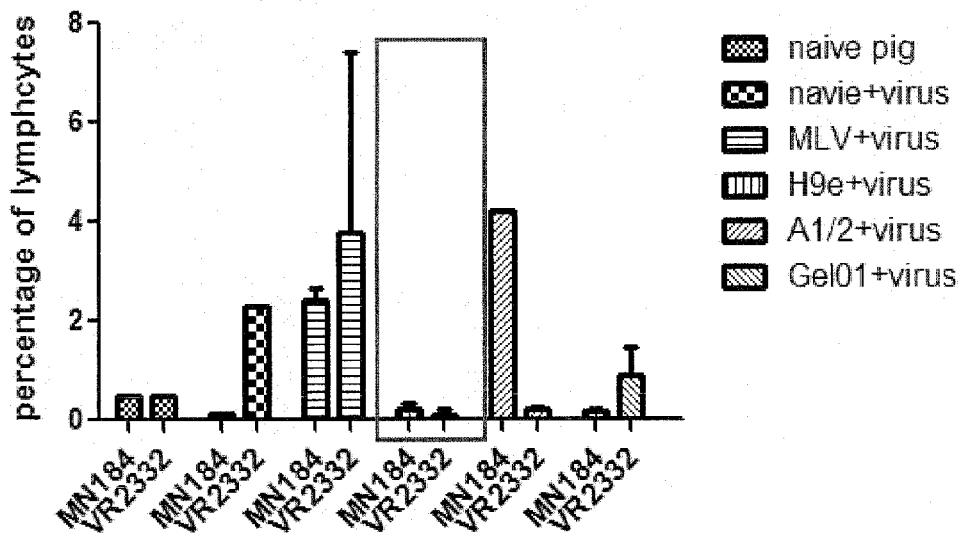
Figure 67:
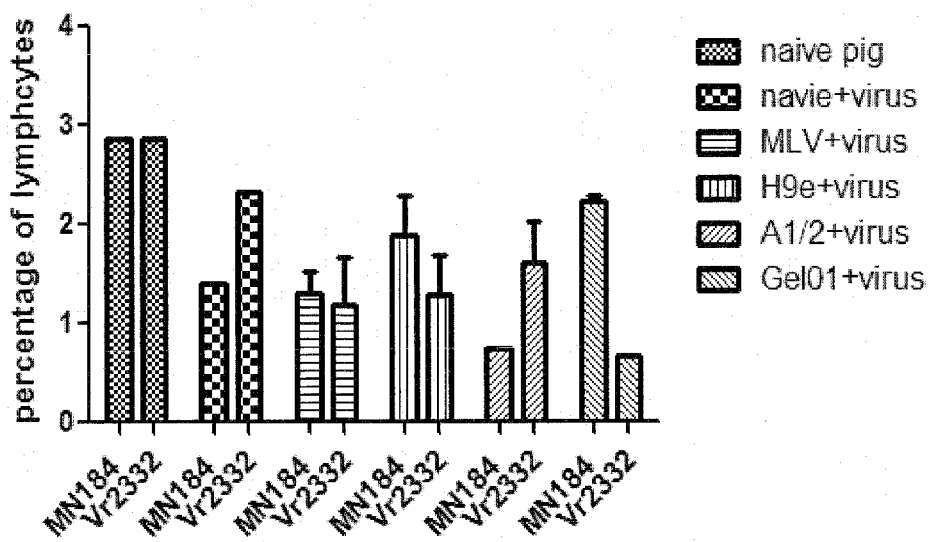
Figure 68:
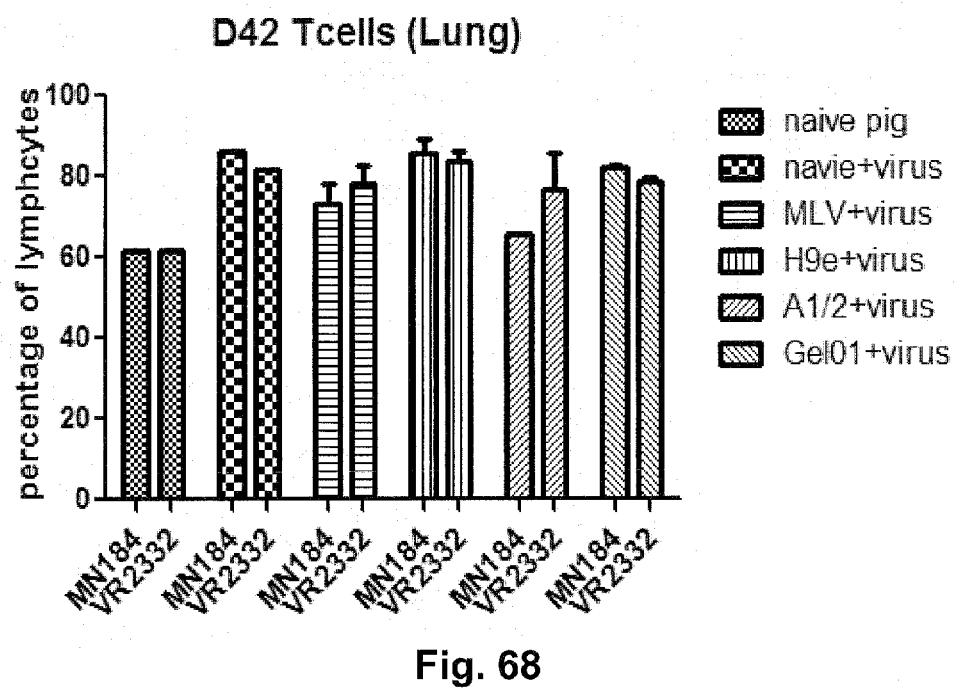
Figure 69:
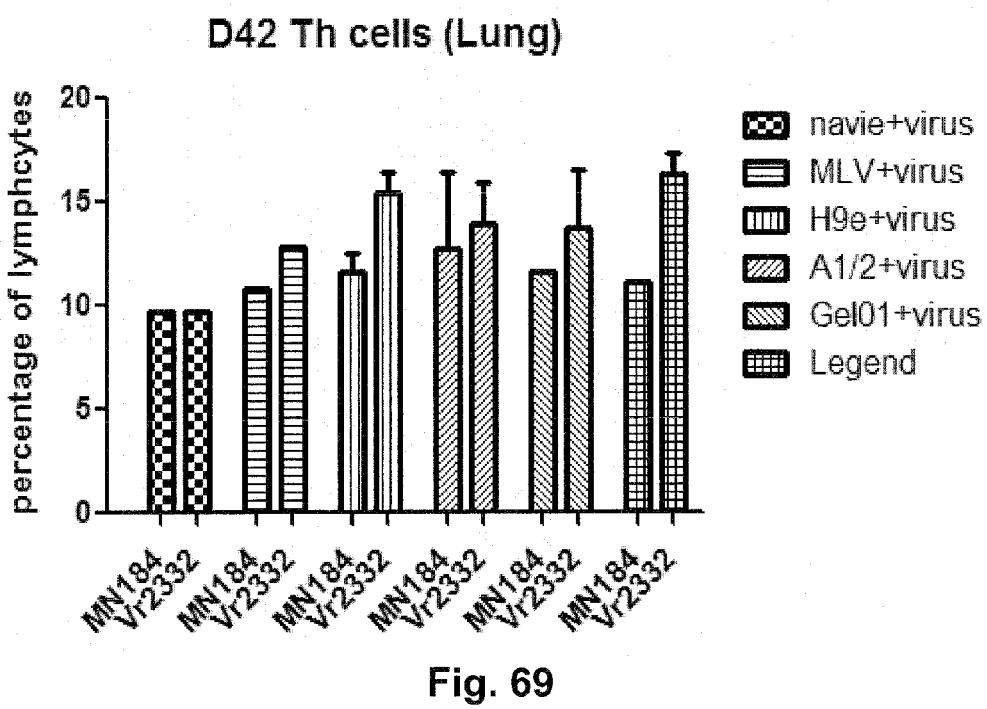
Figure 70:
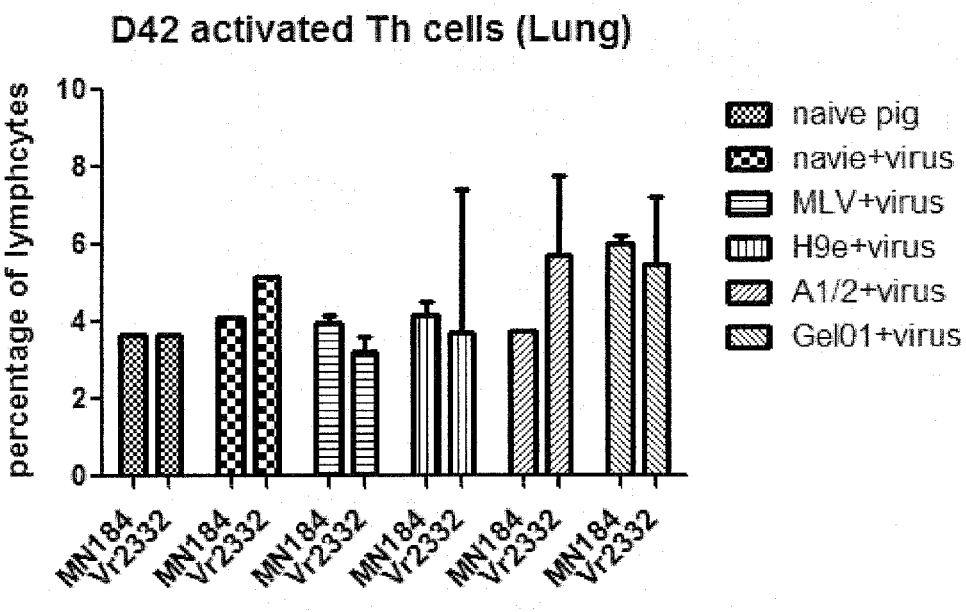
Figure 71:
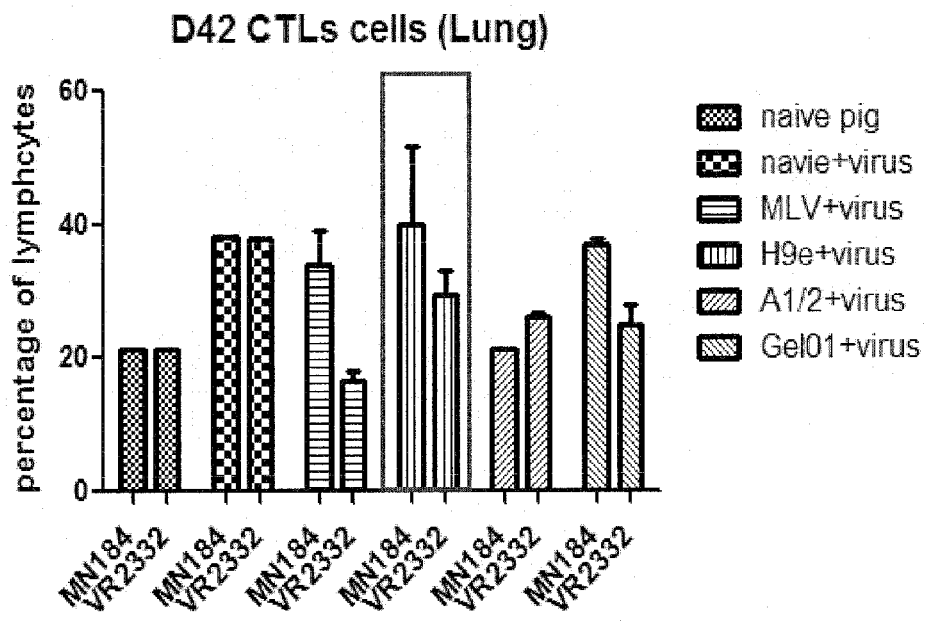
Figure 72:
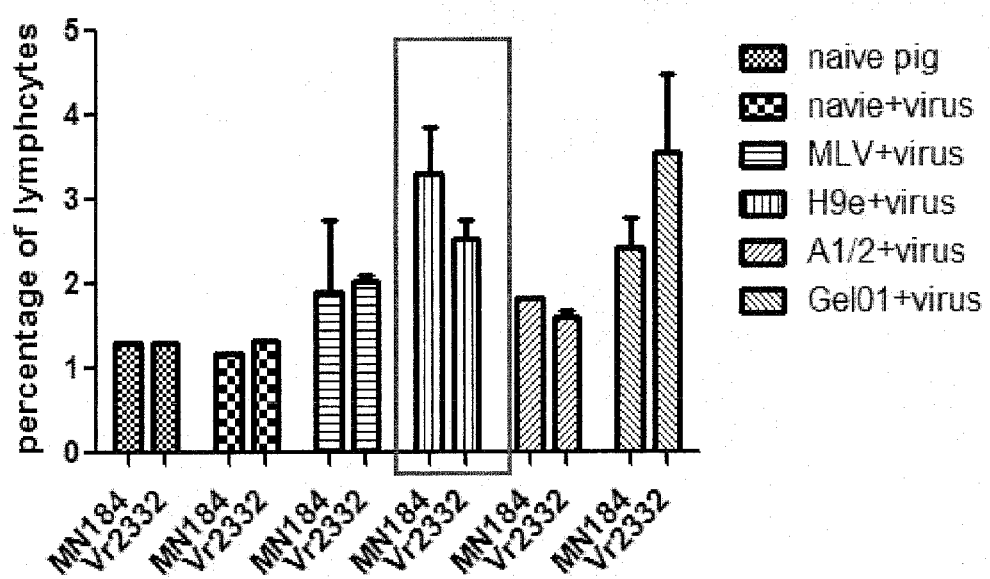
Figure 73:
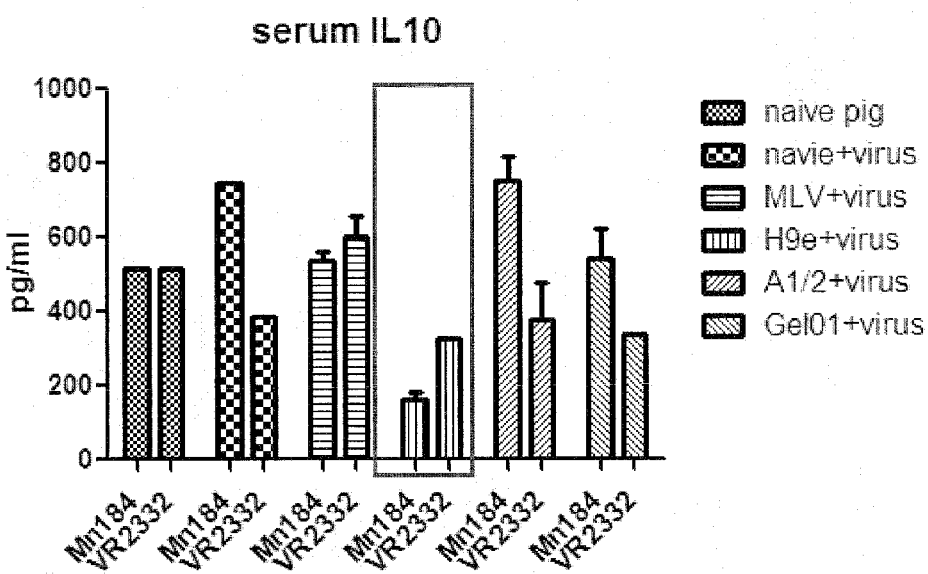
FIGS. 73-76 are graphs of interleukin levels (IL-10 or IL-4) on Day 42 from Example 3.
Figure 74:
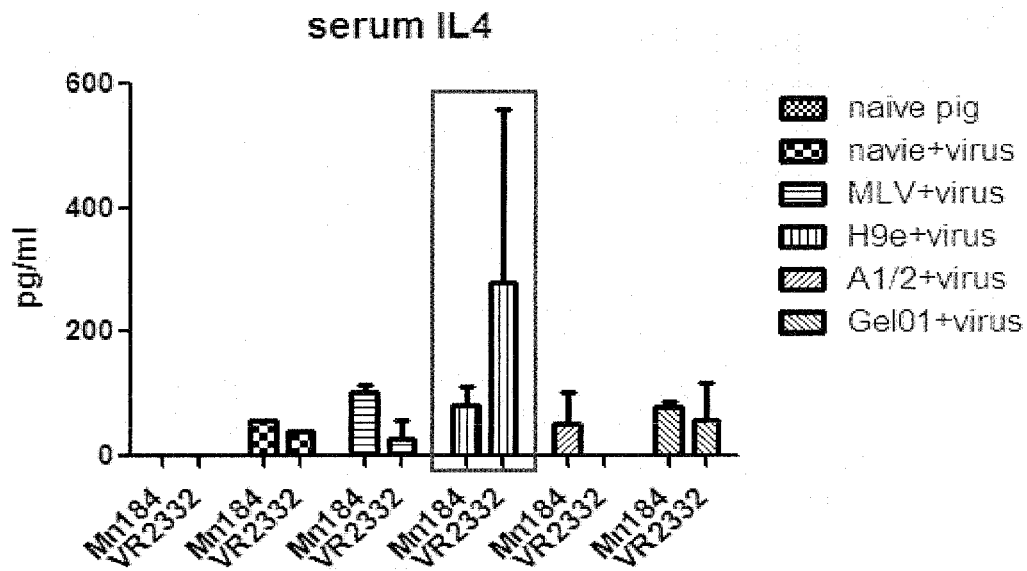
Figure 75:
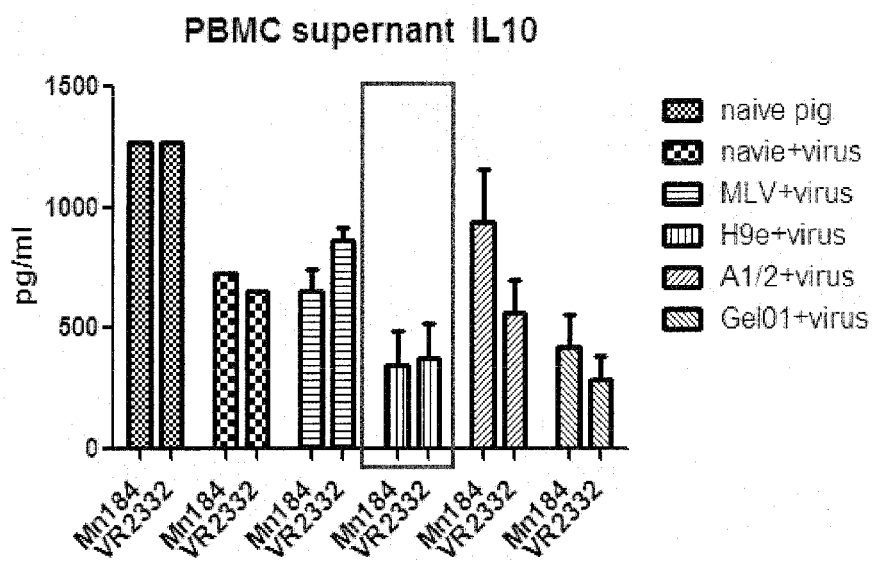
Figure 76:
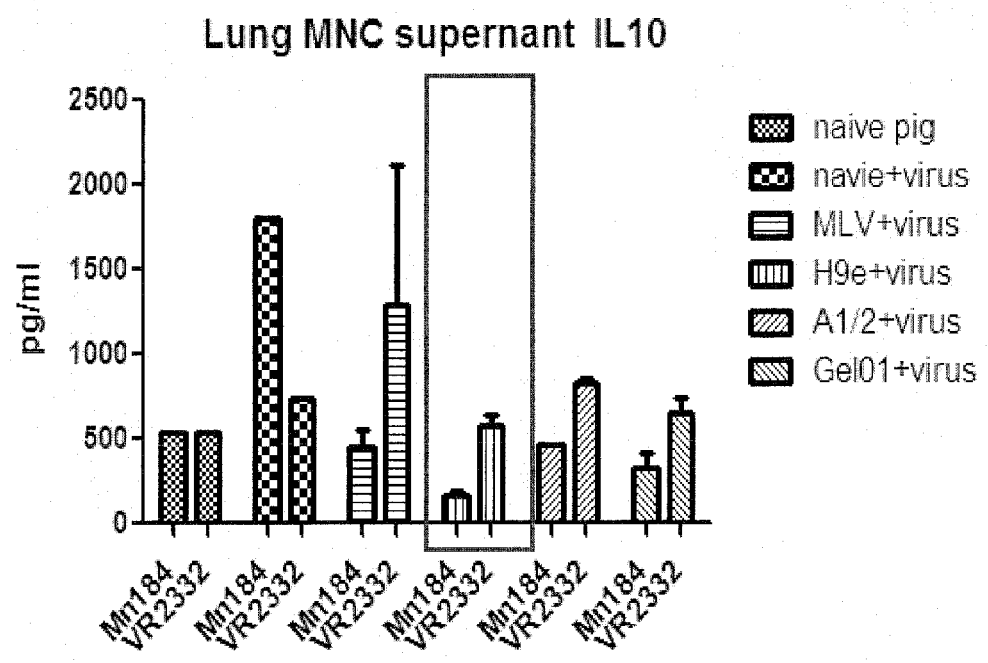

PBMCs (peripheral blood mononuclear cells) from the h9e-adjuvanted group got the highest IFNr-secreting population when re-stimulated with homologous VR2332 or heterologous MN184a after 2 weeks of challenge. It was statistically significant different from the other groups. The results are shown in FIGS. 39-40.

I. Frequency of Different Lymphocyte Populations in Blood on Day 28

The lymphocyte populations on Day 28 were analyzed. MLV vaccination alone reduced the γδ T cells frequency on Day 28 compared to naïve pigs. MLV vaccination alone increase the frequency of T-regulatory cell. All 3 adjuvants helped to reduce the frequency of T-regulatory cells, although h9e and Gel01 worked better. The h9e adjuvant did increase the $CD4^+CD8^+$ T cells (T memory cells) population, which enlarged the pool of memory T cells to PRRSV. The results are shown in FIGS. 41-48.

J. Frequency of Different Lymphocyte Populations in Blood on Day 42

The lymphocyte populations on Day 42 (or 14 days post-challenge) were analyzed. The h9e adjuvant further reduced T-regulatory cell and increased CTL and T memory cell percentages in the blood circulating system two weeks after homologous or heterologous challenge. The results are shown in FIGS. 49-56.

K. Frequency of Different Lymphocyte Populations in TBLN on Day 42

The lymphocyte populations in the tracheobronchial lymph nodes (TBLN), which directly drain to the lungs was analyzed. The h9e adjuvant reduced T-regulatory cell and increased CTL and T memory cell percentages in the lymph nodes two weeks after homologous or heterologous challenge. The results are shown in FIGS. 57-64.

L. Frequency of Different Lymphocyte Populations in Lung on Day 42

The lymphocyte populations in the lung was analyzed. The h9e adjuvant reduced T-regulatory cell and increased CTL and T memory cell percentages in the lungs two weeks after homologous or heterologous challenge. The results are shown in FIGS. 65-72.

M. IL10/IL4 Protein Level on Day 42

ELISA was used to analyze interleukin (IL) levels in serum, PBMC supernatant, and lung mononuclear cells supernatant. The h9e and Gel01 adjuvants helped to reduce IL-10 protein levels in the serum as well as supernatant of cultured PBMCs or Lung MNCs which were re-stimulated with PRRSV. The h9e adjuvant did increase serum IL-4 level when challenged with homologous VR2332 virus but not MN184a virus. The results are shown in FIGS. 73-76.

We claim:

1. A pharmaceutical or veterinary composition comprising a therapeutically effective amount of an amphiphilic peptide adjuvant and an active agent, dispersed in a pharmaceutically acceptable carrier, said peptide adjuvant comprising a peptide having a hydrophobic region, a turning region, and a hydrophilic region, said turning region being between and directly connected to said hydrophobic and hydrophilic regions, said hydrophilic region comprising GPXGDGPXGD (SEQ ID NO:3), KKKKKGPXGD (SEQ ID NO:4), or KKKKKKKKKK (SEQ ID NO:6), where each X is selected from the group consisting of G, R, K, and Q, and said turning region comprising amino acid residues GSII (SEQ ID NO: 10), wherein said peptide is less than 30 amino acid residues in length, and wherein said active agent is selected from the group consisting of killed virus, modified live virus, viral or bacterial proteins, viral or bacterial DNA, toxoids, viral or bacterial protein subunits, and tumor antigens.

2. The composition of claim 1, wherein said hydrophobic regions comprise from about 2 to about 15 amino acid residues, said amino acid residues being selected from the group consisting of F, L, I, V, and combinations thereof.

3. The composition of claim 1, wherein said peptide comprises amino acid residues selected from the group consisting of FLIVIGSIIGPGGDGPGGD (SEQ ID NO:11), FLIVIGSIIKKKKKKKKKK (SEQ ID NO:12), LLLLLGSIIKKKKKKKKKK (SEQ ID NO:13), FLIVIGSIIGPRGDGPRGD (SEQ ID NO:14), FLIVIGSIIGPGGDGPRGD (SEQ ID NO:15), LLLLLGSIIKKKKKGPRGD (SEQ ID NO:16), and fragments or variants thereof having at least about 70% sequence identity thereto.

4. The composition of claim 1, wherein said carrier is selected from the group consisting of normal saline, phosphate buffered saline, sterile water, cell growth medium, aqueous solutions of dimethyl sulfoxide, aqueous solutions of polyethylene glycol, aqueous solutions of dextran, oil-in-water emulsions, and water-in-oil emulsions.

5. The composition of claim 1, said composition further comprising ions or a source of ions, wherein said ions are selected from the group consisting of Ca, Na, Mg, K, and Zn ions.

6. A vaccine system comprising:
an active agent selected from the group consisting of killed virus, modified live virus, viral or bacterial proteins, viral or bacterial DNA, toxoids, viral or bacterial protein subunits, and tumor antigens; and
a therapeutically effective amount of an amphiphilic peptide adjuvant dispersed in a pharmaceutically acceptable carrier, said peptide adjuvant comprising a peptide having a hydrophobic region, a turning region, and a hydrophilic region, said turning region being between and directly connected to said hydrophobic and hydrophilic regions, said hydrophilic region comprising GPXGDGPXGD (SEQ ID NO:3), KKKKKGPXGD (SEQ ID NO:4), or KKKKKKKKKK (SEQ ID NO:6), where each X is selected from the group consisting of G, R, K, and Q, and said turning region comprising amino acid residues GSII (SEQ ID NO: 10), wherein said peptide is less than 30 amino acid residues in length.

7. The system of claim 6, wherein said active agent and said peptide are mixed together in unit dosage form.

8. The system of claim 6, wherein said active agent is in a first container and said peptide adjuvant is in a second container separate from said active agent.

9. The system of claim 6, further comprising ions or a source of ions dispersed in a carrier with said active agent.

10. A kit for vaccinating a subject comprising:
a vaccine system according to claim 6; and
instructions for administering said vaccine system to said subject.

11. The composition of claim 1, wherein said hydrophilic region is derived from spider flagelliform silk protein and wherein said hydrophobic and turning regions are derived from human muscle L-type calcium channel protein.

12. The system of claim 6, wherein said hydrophilic region is derived from spider flagelliform silk protein and wherein said hydrophobic and turning regions are derived from human muscle L-type calcium channel protein.

13. The system of claim 6, wherein said carrier is selected from the group consisting of normal saline, phosphate buffered saline, sterile water, cell growth medium, aqueous solutions of dimethyl sulfoxide, aqueous solutions of polyethylene glycol, aqueous solutions of dextran, oil-in-water emulsions, and water-in-oil emulsions.

14. The composition of claim 1, wherein said amphiphilic peptide adjuvant forms a hydrogel in said carrier.

15. The system of claim 6, wherein said amphiphilic peptide adjuvant forms a hydrogel in said carrier.

16. A pharmaceutical or veterinary composition comprising a therapeutically effective amount of an amphiphilic peptide adjuvant and an active agent, dispersed in a pharmaceutically acceptable carrier, said peptide adjuvant comprising a peptide having a hydrophobic region, a turning region, and a hydrophilic region, said turning region being between and directly connected to said hydrophobic and hydrophilic regions, wherein said peptide comprises amino acid residues selected from the group consisting of FLIVIGSIIGPGGDGPGGD (SEQ ID NO:11), FLIVIGSIIKKKK-KKKKKK (SEQ ID NO:12), LLLLLGSIIKKKKKKKKKK (SEQ ID NO:13), FLIVIGSIIGPRGDGPRGD (SEQ ID NO:14), FLIVIGSIIGPGGDGPRGD (SEQ ID NO:15), LLLLLGSIIKKKKKGPRGD (SEQ ID NO:16), and fragments or variants thereof having at least about 70% sequence identity thereto, and wherein said active agent is selected from the group consisting of killed virus, modified live virus, viral or bacterial proteins, viral or bacterial DNA, toxoids, viral or bacterial protein subunits, and tumor antigens.

17. A pharmaceutical or veterinary composition comprising a therapeutically effective amount of an amphiphilic peptide adjuvant and an active agent, dispersed in a pharmaceutically acceptable carrier, wherein said amphiphilic peptide adjuvant forms a hydrogel in said carrier, said peptide adjuvant comprising a peptide having a hydrophobic region, a turning region, and a hydrophilic region, said turning region being between and directly connected to said hydrophobic and hydrophilic regions, said turning region comprising amino acid residues GSII (SEQ ID NO: 10), wherein said peptide is less than 30 amino acid residues in length, and wherein said active agent is selected from the group consisting of killed virus, modified live virus, viral or bacterial proteins, viral or bacterial DNA, toxoids, viral or bacterial protein subunits, and tumor antigens.

18. The composition of claim 17, wherein said carrier is selected from the group consisting of normal saline, phosphate buffered saline, sterile water, cell growth medium, aqueous solutions of dimethyl sulfoxide, aqueous solutions of polyethylene glycol, aqueous solutions of dextran, oil-in-water emulsions, and water-in-oil emulsions.

19. The composition of claim 17, said composition further comprising ions or a source of ions, wherein said ions are selected from the group consisting of Ca, Na, Mg, K, and Zn ions.

20. A vaccine system comprising:
an active agent selected from the group consisting of killed virus, modified live virus, viral or bacterial proteins, viral or bacterial DNA, toxoids, viral or bacterial protein subunits, and tumor antigens; and
a therapeutically effective amount of an amphiphilic peptide adjuvant dispersed in a pharmaceutically acceptable carrier, said peptide adjuvant comprising a peptide having a hydrophobic region, a turning region, and a hydrophilic region, said turning region being between and directly connected to said hydrophobic and hydrophilic regions, said turning region comprising amino acid residues GSII (SEQ ID NO: 10), wherein said peptide is less than 30 amino acid residues in length, wherein said amphiphilic peptide adjuvant forms a hydrogel in said carrier.

* * * * *